(12) United States Patent
Liu et al.

(10) Patent No.: US 7,297,714 B2
(45) Date of Patent: Nov. 20, 2007

(54) INHIBITORS OF CATHEPSIN S

(75) Inventors: Hong Liu, San Diego, CA (US); Phillip Alper, Poway, CA (US); Daniel Mutnick, San Diego, CA (US); Donald Karanewsky, Escondido, CA (US)

(73) Assignee: IRM LLC, Hamilton (BM)

( * ) Notice: Subject to any disclaimer, the term of this patent is extended or adjusted under 35 U.S.C. 154(b) by 209 days.

(21) Appl. No.: 10/970,344

(22) Filed: Oct. 20, 2004

(65) Prior Publication Data

US 2005/0130959 A1    Jun. 16, 2005

Related U.S. Application Data

(60) Provisional application No. 60/513,735, filed on Oct. 21, 2003.

(51) Int. Cl.
| | |
|---|---|
| *A61K 31/4025* | (2006.01) |
| *A61K 31/341* | (2006.01) |
| *A61K 31/35* | (2006.01) |
| *A61K 31/365* | (2006.01) |
| *C07D 413/06* | (2006.01) |
| *C07D 307/32* | (2006.01) |

(52) U.S. Cl. .................... 514/451; 514/231.5; 514/461; 544/147; 549/295; 548/273; 548/295

(58) Field of Classification Search ............... 548/273, 548/295; 514/451, 461
See application file for complete search history.

(56) References Cited

U.S. PATENT DOCUMENTS 6,103,711 A * 8/2000 Bemis et al. ............... 514/183
6,716,818 B2   4/2004 Cai et al.

FOREIGN PATENT DOCUMENTS

WO    WO 02/42278 A2    5/2002

* cited by examiner

*Primary Examiner*—Rebecca Anderson
*Assistant Examiner*—Michael P. Barker
(74) *Attorney, Agent, or Firm*—Emily Tongco Wu; The Genomics Institute of the Novartis Research Foundation

(57) ABSTRACT

The present invention provides compounds, compositions and methods for the selective inhibition of cathepsin S. In a preferred aspect, cathepsin S is selectively inhibited in the presence of at least one other cathepsin isozyme. The present invention also provides methods for treating a disease state in a subject by selectively inhibiting cathepsin S.

19 Claims, 1 Drawing Sheet

INHIBITORS OF CATHEPSIN S

CROSS-REFERENCE TO RELATED APPLICATIONS

This application claims priority to U.S. Provisional Patent Application No. 60/513,735, filed on Oct. 21, 2003, the teaching of which is hereby incorporated by reference in its entirety for all purposes.

BACKGROUND OF THE INVENTION

Cysteine proteases represent an enzymatic class of proteins that catalyze the hydrolysis of peptide bonds by a nucleophilic sulfhydryl group of a cysteine residue in the active site of the enzyme. Several normal and disease processes in mammals have been associated with cysteine protease activity and include, but are not limited to: osteoporosis, osteoarthritis (Inui, T., O. Ishibashi, *J Biol Chem* 1997, 272(13), 8109-12; Saftig, P., E. Hunziker, et al., *Adv Exp Med Biol* 200030 ADs 2000, 477, 293-303; Saftig, P., E. Hunziker, et al., *Proc Natl Acad Sci USA* 1998, 95(23), 13453-8), periodontal diseases, Paget's disease, atherosclerosis (Jormsjo, S., D. M. Wuttge, et al., *Am J Pathol* 2002 161(3), 939-45), multiple sclerosis (Beck, H., G. Schwarz, et al., *Eur J Immunol* 2001, 31(12), 3726-36), rheumatoid arthritis (Nakagawa, T. Y., W. H. Brissette, et al., *Immunity* 1999, 10(2), 207-17; Hou, W. S., Z. Li, et al., *Am J Pathol* 2001, 159(6), 2167-77), juvenile onset diabetes, lupus, asthma (Cimerman, N., P. M. Brguljan, et al., *Pflugers Arch* 2001, 442(6 Suppl 1), R204-6), tissue rejection, Alzheimer's disease (Lemere, C. A., J. S. Munger, et al., *Am J Pathol* 1995, 146(4), 848-60), Parkinson's disease (Liu, Y., L. Fallon, et al., *Cell* 2002, 111(2), 209-18), neuronal degeneration, shock (Jaeschke, H., M. A. Fisher, et al., *J Immunol* 1998, 160(7), 3480-6), cancer (Fernandez, P. L., X. Farre, et al., *Int J Cancer* 2001, 95(1), 51-5), malaria (Malhotra, P., P. V. Dasaradhi, et al., *Mol Microbiol* 2002, 45(5), 1245-54), Chagas (Eakin, A. E., A. A. Mills, et al., *J Biol Chem* 1992, 267(11), 7411-20), leishmaniasis, shistosomiasis, and African trypanosomiasis (Caffrey, C. R., S. Scory, et al., *Curr Drug Targets* 2000, 1(2), 155-62; Lalmanach, G., A. Boulange, et al., *Biol Chem* 2002, 383(5), 739-49).

Cathepsins are a subclass of cysteine protease that belong to the enzyme classification EC 3.4.22 (Barrett, A. J., N. D. Rawlings, et al., *Handbook of proteolytic enzymes*. London, Academic Press). Cathepsins play a major role in lysosomal, endosomal, and extracellular protein degradation and have thus been implicated in many disease processes. For example, Cathepsin B [EC 3.4.22.1] has been postulated to play a role in tumor metastasis (Berquin, I. M. and B. F. Sloane *Adv Exp Med Biol* 1996, 389, 281-94).

Cathepsin S [EC 3.4.22.27] is largely expressed in professional antigen presenting cells such as macrophages and dendritic cells. Cathepsin S has been shown to be required for proper MHC class II antigen presentation (Shi, G. P., J. A. Villadangos, et al., *Immunity* 1999, 10(2) 197-206). As a result of its non-redundant role in MHC class II antigen presentation, cathepsin S has been associated with inflammation, arthritis, and atherosclerosis. The selective expression of cathepsin K [EC 3.4.22.38] in osteoclasts coupled with the ability of cathepsin K to degrade type I collagen suggests that it plays a role in normal and pathogenic bone remodeling (Bromme, D., K. Okamoto, et al., *J Biol Chem* 1996, 271(4), 2126-32). There is a need in the art for compounds and methods that selectively inhibit specific cysteine proteases for treating several pathogenic disorders in mammals. The present invention satisfies these and other needs.

SUMMARY OF THE INVENTION

The present invention provides compounds, compositions and methods for the selective inhibition of cathepsin S. The compounds of the present invention are selective for cathepsin S in the presence of other cathepsin isozymes. In a preferred embodiment, the compounds of the present invention are selective for cathepsin S in the presence of cathepsin K, L, B, or combinations thereof. The present invention also provides methods for treating a disease state in a subject by selectively inhibiting cathepsin S in the presence of other cathepsin isozymes. In a preferred aspect, cathepsin S is selectively inhibited in the presence of cathepsin K, L, B, or combinations thereof. In another preferred embodiment, the compounds of the present invention do not inhibit a caspase, such as a caspase-1, -3-8 or a combination thereof.

In a first aspect, the present invention provides a compound of Formula I:

or a pharmaceutically acceptable salt or prodrug thereof, wherein:

Y is a member selected from the group consisting of

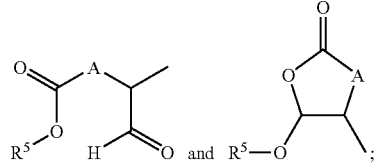

A is a member selected from the group consisting of —$CH_2$—, and —$CH_2CH_2$—;

$R^5$ is independently a member selected from the group consisting of H, $C_1$-$C_6$ alkyl, $C_3$-$C_8$ cycloalkyl, $C_1$-$C_4$ alkyl substituted $C_3$-$C_8$ cycloalkyl, with and benzyl;

X is a member selected from the group consisting of —O—$CR^1R^2$—C(=O)—Q, —$CR^3H$—O—C(=O)—W, —$CH_2$—$CHR^3$—C(=O)—W, —$CR^3H$—$CH_2$—C(=O)—W, —$CR^4H$—NH—C(=O)—W, —O—$CR^1R^2$—B—$R^6$, —$CR^3H$—NH—C(=O)—O—Z, —$CHR_4$—NH—C(=O)—$R^7$, and —$CHR^4$—NH—S(=O)$_2$—$R^8$;

Q is a heterocycle selected from the group consisting of pyrrolidinyl, piperidyl, morpholinyl, thiomorpholinyl, piperazinyl and indolinyl substituted with 0-2 $R^Q$, wherein Q is connected to —C(=O)— via a ring nitrogen atom;

each $R^Q$ is independently a member selected from the group consisting of OH, —S(=O)$_2$$CH_3$, acetyl, =O, $C_1$-$C_6$ alkyl, $C_1$-$C_6$ alkoxy, $CF_3$, $OCF_3$ and $NR^{10}R^{11}$;

W is morpholinyl, wherein W is connected to —C(=O)— via the ring nitrogen atom;

Z is a heterocycle selected from the group consisting of tetrahydrofuranyl, tetrahydropyranyl, thiotetrahydropyranyl, thiotetrahydrofuranyl, pyrrolidinyl, piperidyl, morpholinyl, thiomorpholinyl, piperazinyl and indolinyl each substituted with 0-2 $R^Z$, wherein Z is connected to —O—C(=O)— via a ring carbon atom;

each $R^Z$ is independently a member selected from the group consisting of OH, —S(=O)$_2$CH$_3$, acetyl, =O, $C_1$-$C_6$ alkyl, $C_1$-$C_6$ alkoxy, $CF_3$, $OCF_3$ and $NR^{10}R^{11}$;

B is a member selected form the group consisting of —CH$_2$—, —OCH$_2$—, —NR$^{11}$CH$_2$—, —CH$_2$CH$_2$— and a bond;

each $R^1$ is independently a member selected from the group consisting of H, a $C_1$-$C_6$ alkyl substituted with 0-2 $R^{1a}$, wherein said $C_1$-$C_6$ alkyl is optionally substituted with a heteroatom selected from the group consisting of —O—, —S—, —S(=O)—, and —S(=O)$_2$—; a $C_2$-$C_6$ alkenyl, a $C_3$-$C_6$ alkynyl, a $C_3$-$C_7$ cycloalkyl each substituted with 0-2 $R^{1b}$, and a $C_7$-$C_{11}$ bicycloalkyl substituted with 0-2 $R^{1b}$; phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;

each $R^{1a}$ is independently a member selected from the group consisting of a $C_6$-$C_{10}$ aryl substituted with 0-3 $R^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1c}$, a $C_3$-$C_8$ cycloalkyl substituted with 0-2 $R^{1b}$, a $C_7$-$C_{11}$ bicycloalkyl substituted with 0-2 $R^{1b}$, and a $C_1$-$C_3$ perfluoroalkyl;

each $R^{1b}$ is independently a member selected from the group consisting of a H, $C_1$-$C_6$ alkyl, $C_1$-$C_6$ alkoxy, $CF_3$, $OCF_3$, —S(=O)$_2$CH$_3$, and acetyl;

each $R^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, $C_1$-$C_6$ alkoxy, $C_1$-$C_3$ perfluoroalkyl, $C_1$-$C_3$ perfluoroalkoxy and a $C_1$-$C_6$ alkyl;

each $R^2$ is independently a member selected from the group consisting of H and $C_1$-$C_6$ alkyl;

each $R^3$ is a $C_1$-$C_2$ alkyl substituted with 1 $R^{3a}$;

each $R^{3a}$ is independently a member selected from the group consisting of a $C_3$-$C_7$ cycloalkyl substituted with 0-2 $R^{1b}$, and a $C_7$-$C_{11}$ bicycloalkyl substituted with 0-2 $R^{1b}$;

each $R^4$ is a $C_1$-$C_2$ alkyl substituted with 1 $R^{4a}$;

each $R^{4a}$ is independently a member selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;

$R^6$ is independently a member selected from group consisting of a 5- to 6-membered monocyclic heteroaryl containing 1 to 4 heteroatoms each independently a member selected from the group consisting of N, O and S, wherein said heteroaryl is substituted with 1 $R^{6a}$ and 0-2 $R^{1c}$; and a 8- to 10-membered bicyclic heteroaryl containing 1 to 4 heteroatoms each independently a member selected from the group consisting of N, O and S, wherein said heteroaryl is substituted with 0-3 $R^{1c}$;

each $R^{6a}$ is independently a member selected from the group consisting of phenyl substituted with 0-3 $R^{1c}$; a 5- to 6-membered heteroaryl containing 1 to 4 heteroatoms each independently a member selected from the group consisting of N, O and S, wherein said heteroaryl is substituted with 0-3 $R^{1c}$;

$R^7$ is a member selected from the group consisting of a 5-membered heteroaryl containing 1 to 4 heteroatoms each independently a member selected from the group consisting of N, O and S, wherein said heteroaryl is substituted with 1 $R^{6a}$ and 0-2 $R^{1c}$; a phenyl substituted with 0-3 $R^{1c}$, OCH$_2$Ph, O-tert-Bu, and $C_3$-$C_6$ cycloalkyl;

$R^8$ is a member selected from the group consisting of a phenyl substituted with 0-3 $R^{1c}$, and a 5- to 6-membered heteroaryl containing 1 to 4 heteroatoms each independently a member selected from the group consisting of N, O and S, wherein said heteroaryl is substituted with 0-3 $R^{1c}$;

each $R^{10}$ is independently a member selected from the group consisting of H, $C_1$-$C_4$ alkyl, ($C_1$-$C_4$ alkyl)-C(=O)— and ($C_1$-$C_4$ alkyl)—S(=O)$_2$—;

each $R^{11}$ is independently a member selected from the group consisting of H and $C_1$-$C_4$ alkyl; and each $R^{12}$ is independently a member selected from the group consisting of H and $C_1$-$C_4$ alkyl.

In a second aspect, the present invention provides a pharmaceutical composition. Comprising a compound of Formula I, as described above, and a pharmaceutically acceptable excipient.

In a third aspect, the present invention provides a method of selectively inhibiting the cathepsin S activity in a mammal in need thereof, comprising administering to the mammal a therapeutically effective amount of a compound of Formula I, as described above, or a pharmaceutically acceptable salt or prodrug thereof.

These and other aspects, objects and embodiments will become more apparent when read with the accompanying figure and detailed description which follows.

DETAILED DESCRIPTION OF THE INVENTION

I. Definitions

Figure 1:
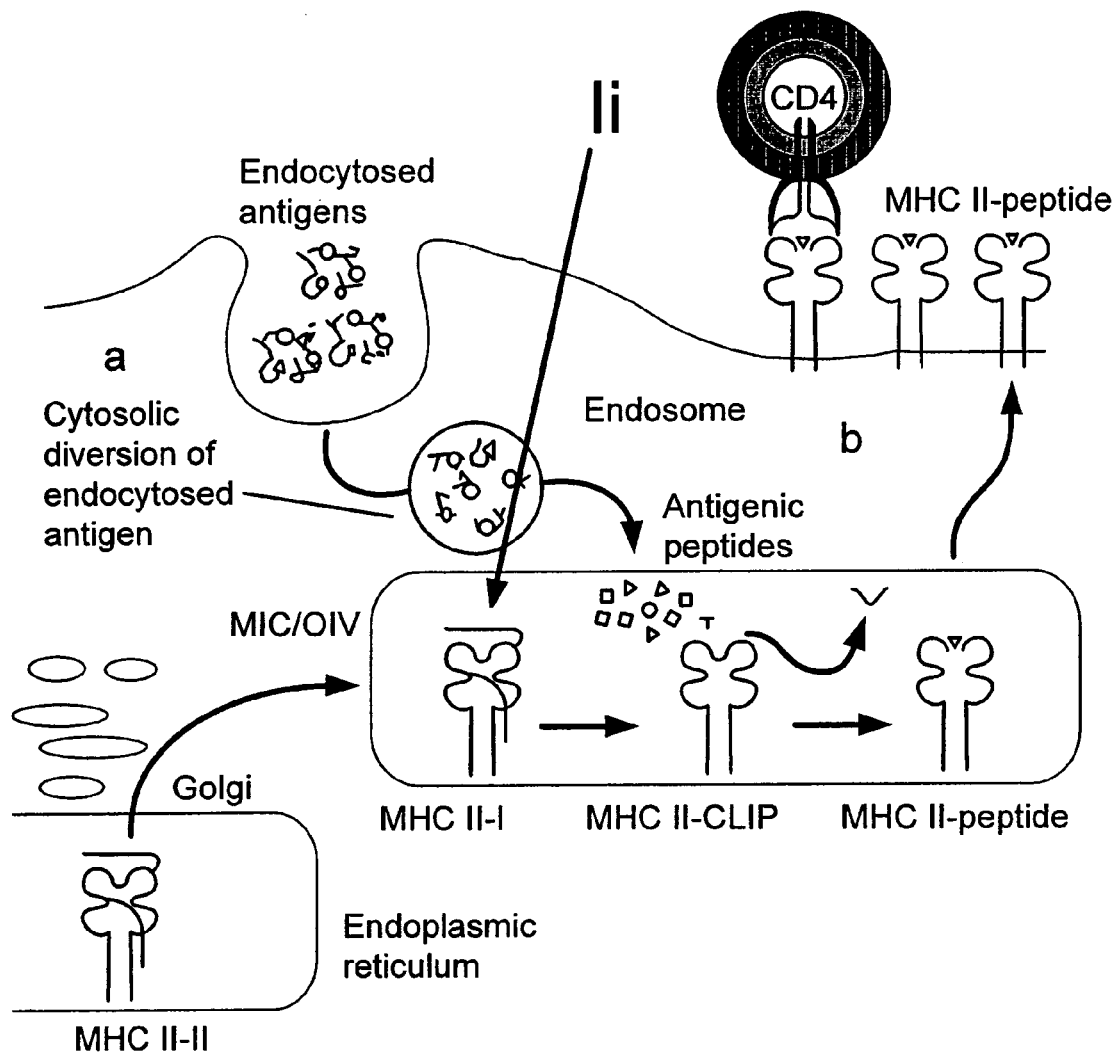
FIG. 1 depicts MHC II antigen presentation.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used in this disclosure, the following abbreviations and terms have the defined meaning, unless expressly modified in the context in which the term is used:

Ac acetyl
Bn benzyl
Boc t-butoxycarbonyl
Cbz or Z benzyloxycarbonyl
DCC N,N'-dicyclohexylcarbodiimide
DCM dichoromethane
DIBAL diisobutylaluminum hydride
DIC N,N'-diisopropylcarbodiimide
DIEA or DIPEA diisopropylethylamine
DMAP 4-(dimethylamino)pyridine
DMF dimethylformamide
DMSO dimethyl sulfoxide EDC or EDCI 1-ethyl-3-(dimethylaminopropyl)-carbodiimide
Fmoc 9-fluorenylmethoxycarbonyl
HATU O-(7-azabenzoatriazol-1-yl)-N,N,N',N'-tetramethyluronium hexafluorophosphate
HOBt 1-hydroxybenzotriazole
KHMDS potassium hexamethyldisilazide
LAH lithium aluminum hydride
LDA lithium diisopropylamide
LHMDS lithium hexamethyldisilazide
m-CPBA m-chloroperbenzoic acid
MW microwave
NaHMDS sodium hexamethyldisilazide
PCC pyridinium chlorochromate
PDC pyridinium dichromate
PG protecting group
PTSA p-toluenesulfonic acid
Py pyridine
RT or rt room temperature
TEA triethylamine
Tf trifluoromethanesulfonyl
TFA trifluoroacetic acid
THF tetrahydrofuran
Tol p-tolyl
TPAP tetrapropylammonium perruthenate The term "lower" referred to above and hereinafter in connection with organic radicals or compounds respectively defines a compound or radical which can be branched or unbranched with up to and including 7, preferably up to and including 4 and (as unbranched) one or two carbon atoms.

The term "perfluoro" referred to above and hereinafter in connection with organic radicals or compounds respectively, defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

An alkyl group is branched or unbranched and contains 1 to 7 carbon atoms, preferably 1-4 carbon atoms. Alkyl represents, for example, methyl, ethyl, propyl, butyl, isopropyl or isobutyl.

Alkenyl represents either straight chain or branched alkenyl of 2 to 7 carbon atoms, preferably 2-4 carbon atoms, e.g. as vinyl, propenyl, isopropenyl, butenyl, isobutenyl or butadienyl.

Alkynyl represents either straight chain or branched alkynyl of 2 to 7 carbon atoms, preferably 2-4 carbon atoms, e.g. as acetylenyl, propynyl, isopropynyl, butynyl or isobutynyl.

Alkyl, alkenyl or alkynyl can be substituted by up to 3 substituents selected from alkoxy, aryl, heterocyclyl, hydroxy, halogen, cyano, optionally substituted amino, or optionally substituted amino-oxy or trifluoromethyl.

Alkylene represents either straight chain or branched alkylene of 1 to 7 carbon atoms, i.e. a divalent hydrocarbon radical of 1 to 7 carbon atoms; for instance, straight chain alkylene being the bivalent radical of formula —$(CH_2)_n$-, where n is 1, 2, 3, 4, 5, 6 or 7. Preferably alkylene represents straight chain alkylene of 1 to 4 carbon atoms, e.g. a methylene, ethylene, propylene or butylene chain, or the methylene, ethylene, propylene or butylene chain monosubstituted by $C_1$-$C_3$-alkyl (preferably methyl) or disubstituted on the same or different carbon atoms by $C_1$-$C_3$-alkyl (preferably methyl), the total number of carbon atoms being up to and including 7.

An alkoxy (or alkyloxy) group preferably contains 1-7 carbon atoms, more preferably 1-6 carbon atoms, and represents for example ethoxy, propoxy, isopropoxy, isobutoxy, preferably methoxy. Alkoxy includes cycloalkyloxy and cycloalkyl-alkyloxy.

Halogen (halo) preferably represents chloro or fluoro, but may also be bromo or iodo.

Aryl represents monocyclic, bicyclic or tricyclic aryl, for example, phenyl or phenyl mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl. Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

Examples of substituted phenyl groups as R are, e.g. 4-chlorophen-1-yl, 3,4-dichlorophen-1-yl, 4-methoxyphen-1-yl, 4-methylphen-1-yl, 4-aminomethylphen-1-yl, 4-methoxyethylaminomethylphen-1-yl, 4-hydroxyethylaminomethylphen-1-yl, 4-hydroxyethyl-(methyl)-aminomethylphen-1-yl, 3-aminomethylphen-1-yl, 4-N-acetylaminomethylphen-1-yl, 4-aminophen-1-yl, 3-aminophen-1-yl, 2-aminophen-1-yl, 4-phenyl-phen-1-yl, 4-(imidazol-1-yl)-phen-yl, 4-(imidazol-1-ylmethyl)-phen-1-yl, 4-(morpholin-1-yl)-phen-1-yl, 4-(morpholin-1-ylmethyl)-phen-1-yl, 4-(2-methoxyethylaminomethyl)-phen-1-yl and 4-(pyrrolidin-1-ylmethyl)-phen-1-yl, 4-(thiophenyl)-phen-1-yl, 4-(3-thiophenyl)-phen-1-yl, 4-(4-methylpiperazin-1-yl)-phen-1-yl, and 4-(piperidinyl)-phenyl and 4-(pyridinyl)-phenyl optionally substituted in the heterocyclic ring.

Benzyl represents a phenyl-$CH_2$-group. Substituted benzyl means a benzyl group in which the phenyl ring is substituted with one or more ring system substituents. Representative benzyl groups include 4-bromobenzyl, 4-methoxybenzyl, 2,4-dimethoxybenzyl, and the like.

Heteroaryl represents monocyclic or bicyclic heteroaryl, for example pyridyl, pyridyl N-oxide, indolyl, indazolyl, quinoxalinyl, quinolinyl, isoquinolinyl, benzothienyl, benzofuranyl, benzopyranyl, benzothiopyranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Preferably, heteroaryl is pyridyl, pyridyl N-oxide, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

Biaryl may preferably be, e.g., biphenyl, namely 2, 3 or 4-biphenyl, preferably, 4-biphenyl, each optionally substituted by, e.g., alkyl, alkoxy, halogen, trifluoromethyl or cyano, or heterocyclic-carbocyclic biaryl, preferably, e.g., thienylphenyl, pyrrolylphenyl and pyrazolylphenyl.

Cycloalkyl represents a saturated cyclic hydrocarbon optionally substituted by alkyl which contains 3 to 10 ring carbons and is advantageously cyclopentyl, cyclohexyl, cycloheptyl or cyclooctyl optionally substituted by alkyl. The radical "$C_1$-$C_4$ alkyl substituted $C_3$-$C_8$ cycloalkyl" means that the cycloalkyl group is substituted with an alkyl group, for example a cyclopropyl methyl, cyclopentyl methyl, cyclohexyl methyl, and the like. In certain instances, the "$C_1$-$C_4$ alkyl" portion is attached to $C_3$-$C_8$ cycloalkyl as well as another portion of the molecule (e.g., divalent).

Bicycloalkyl represents a saturated bicyclic ring group of 7-15 carbon atoms. Exemplary bicycloalkyl rings include [3.3.0]bicyclooctanyl, [2.2.2]bicyclooctanyl, [4.3.0]bicyclononane, [4.4.0]bicyclodecane (decalin), spiro[3.4]octanyl, spiro[2.5]octanyl, and so forth, optionally substituted by alkyl.

Amino can be optionally substituted by, e.g., alkyl.

Carbocyclic represents a saturated or partially unsaturated cyclic hydrocarbon with 5 to 7 ring members, wherein 1 to 2 ring members can optionally be replaced with one of the following groups: —O—, —S—, —S(=O)—, —S(=O)$_2$— and —NR—, wherein R is a radical of the present invention.

Heterocyclyl represents a saturated cyclic hydrocarbon containing one or more, preferably 1 or 2, hetero atoms selected from O, N or S, and from 3 to 10, preferably 5 to 8, ring atoms; for example, tetrahydrofuranyl, tetrahydrothienyl, tetrahydropyrrolyl, piperidinyl, piperazinyl or morpholino; all of which can be optionally substituted, for instance as hereinbefore defined for aryl.

Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

"Treat", "treating" and "treatment" refer to a method of alleviating or abating a disease and/or its attendant symptoms.

"Inhibition", "inhibits" and "inhibitor" refer to a compound that prohibits, or a method of prohibiting, a specific action or function.

"Inhibition constant", $K_i$, is the dissociation constant of the enzyme-inhibitor complex, or the reciprocal of the binding affinity of the inhibitor to the enzyme. For classical inhibition the value of $K_i$ is much greater than the enzyme concentration and the $K_i$ can be measured by monitoring the rate of reaction for a competitive substrate at multiple inhibitor concentrations. The inhibited rates are then fit by nonlinear regression to the following equation:

$$v_i/v_o = \frac{K_m + [S]}{K_m(1 + [I]/K_i) + [S]}$$

where $v_o$ is the initial rate of substrate processing in the absence of inhibitor, $v_i$ is the initial rate of substrate processing at a concentration [I] of inhibitor, $K_m$ is the steady state Michaelis constant (Fersht, A. *Structure and Mechanism in Protein Science*. New York, W.H. Freeman and Company, 1999), and [S] is the concentration of competitive substrate.

The assumption being made for the classical inhibition described above is that the free inhibitor concentration is equal to the total inhibitor concentration. For inhibitors that have $K_i$'s that are approximately equal to the enzyme concentration [E], the assumption that the free inhibitor concentration is equal to the total inhibitor concentration is no longer valid and an alternative equation has to be fit for determination of the apparent inhibition constant, $K_i^{app}$ using described methods (Kuzmic, P., K. C. Elrod, et al., *Anal Biochem* 2000, 286(1), 45-50):

$$v_i/v_o = \frac{[E] - [I] - K_i^{app} + SQRT(([E] - [I] - K_i^{app})^2 + 4[E]K_i^{app})}{2[E]}.$$

The inhibition constant, $K_i$, can be determined from the apparent inhibition constant, $K_i^{app}$, for competitive inhibitors by using the following relationship:

$$K_i = \frac{K_i^{app}}{1 + [S]/K_m}.$$

"Therapeutically effective amount" refers to that amount of the compound being administered sufficient to prevent development of or alleviate to some extent one or more of the symptoms of the condition or disorder being treated.

"Composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the Formulation and deleterious to the recipient thereof.

"Subject" refers to animals such as mammals, including, but not limited to, primates (e.g., humans), cows, sheep, goats, horses, dogs, cats, rabbits, rats, mice and the like. In certain aspects, the subject is a human.

"Prodrug" refers to the compounds of this invention which may be modified by appending appropriate functionalities to enhance selective biological properties. Such modifications are known in the art and include those which increase penetration into a given biological compartment (e.g. central nervous system), increase oral bioavailability, increase solubility to allow administration by injection, alter metabolism and alter rate and/or route of excretion. In addition, the compounds may be altered to prodrug form such that the desired compound is created in the body of the patient as the result of the action of metabolic or other biochemical processes on the prodrug.

Compounds of this invention, wherein $R^5$=H, may exist in solution as either the open form 1a or the cyclic hemiacetal or acetal form 1a'. The representation herein of either isomeric form is meant to include the other.

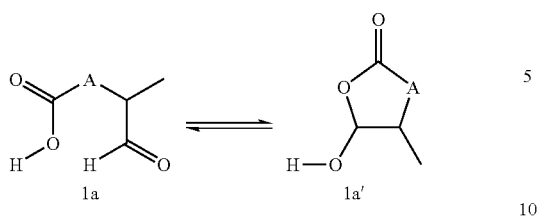

Likewise, it will be apparent to one skilled in the art that certain compounds of this invention may exist in tautomeric forms or hydrated forms, all such forms of the compounds being within the scope of the invention.

Structures depicted herein are also meant to include compounds that differ only in the presence of isotopically enriched atoms. For example, compounds having the present structures except for the replacement of a hydrogen by a deuterium are expressly included in the present invention.

II. General

Cathepsin S is a cysteine protease that has been associated with several normal and disease processes in mammals. Specifically, cathepsin S has been directly associated with inflammation, arthritis, and atherosclerosis, as a result of its role in MHC class II antigen presentation. In a preferred aspect, the present invention provides compounds that inhibit the activity of cathepsin S. The present invention also provides methods for treating several disease states in mammals by inhibiting the activity of cathepsin S. In a more preferred aspect, the compounds of the present invention selectively inhibit cathepsin S in the presence of at least one cathepsin isozyme.

III. Compounds

A. Preparation of Compounds

In the following schemes, several methods of preparing the compounds of the present invention are illustrative. One of skill in the art will appreciate that these methods are representative, and in no way inclusive of all methods for preparing the compounds of the present invention. The radicals in the schemes are as described in Formula I.

The aspartic acid derivatives as depicted in Scheme 1 can be prepared by methods well known in the art, see for example, D. S. Karanewsky et al. US2002/0042376 and references cited therein.

Scheme 1

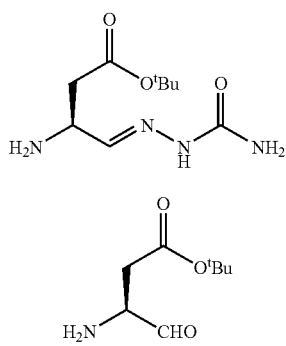

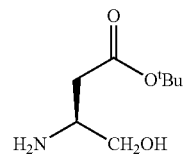

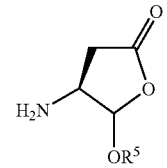

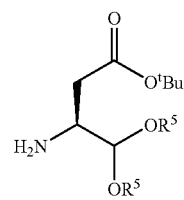

Amide coupling reactions were carried out under standard conditions, such as those described in M. Bodanszky and A. Bodanszky, "The Practice of Peptide Synthesis", Springer-Verlay $2^{nd}$ ed. 1994.

Compounds of the present invention can be made via the route shown in Scheme 2. The protected 4-oxo butanoic acid 2-A reported in the literature (D. S. Karanewsky et al. WO 00/01666) was coupled to an acid or acid chloride using standard coupling methodology to afford 2-B. After further synthetic manipulations on group X, such as those described in the example section, the hemiacetal was then generated by first removing the t-Bu group using TFA in DCM and anisole, and then exchange with formaldehyde in a mixture of acetic acid and dioxane or methanol to yield 2-D.

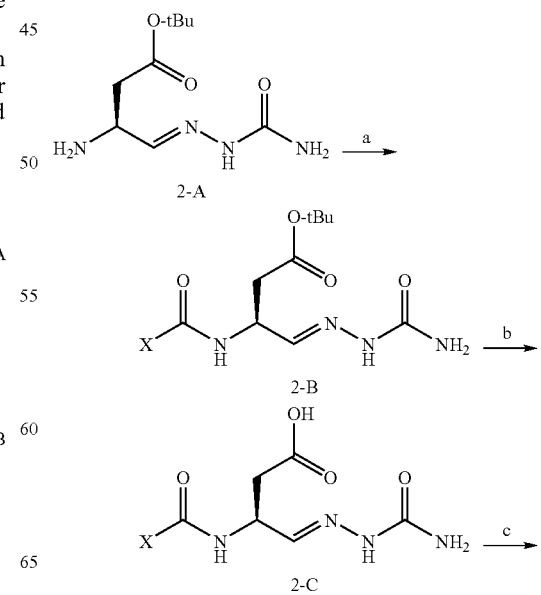

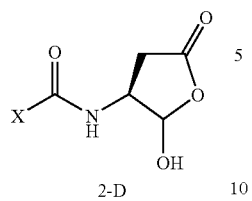

2-D a) X—COOH or X—COCl, standard amide coupling; further manipulation of group X;
b) TFA, anisole, DCM;
c) formaldehyde, AcOH, dioxane or methanol.

In another embodiment, the compounds of the present invention can be synthesized as shown in Scheme 3. The route started with Cbz-aspartinol t-butyl ester 3-A which was de-protected to the amine. The resulting amine was coupled with X—COOH or X—COCl to afford 3-B. The alcohol 3-B was then oxidized, and the resulting aldehyde was converted to the semicarbazone 3-C. In the last step, the hemiacetal was generated as described before. Preferred methods for the oxidation of alcohols to the corresponding aldehydes include, but are not limited to, the procedure as described in Dess-Martin periodinane (D. B. Dess et al. *J. Am. Chem. Soc.* 1991, 113, 7277 and *J. Org. Chem.* 1983, 48, 4155), Swern oxidation as well as its variations (D. Swern et al. *J. Org. Chem.* 1978, 43, 2480; T. T. Tidwell Org. React. 1990, 39, 297; M. Hudlicky *Oxidations in Organic Chemistry*; ACS: Washington, 1990), PCC (E. J. Corey et al. *Tetrahedron Lett.* 1975, 2647; G. Piancatelli *Synthesis* 1982, 245), PDC (E. J. Corey et al. *Tetrahedron Lett.* 1979, 399) and TPAP catalyzed oxidation (S. V. Ley et al. *Synthesis* 1994, 639).

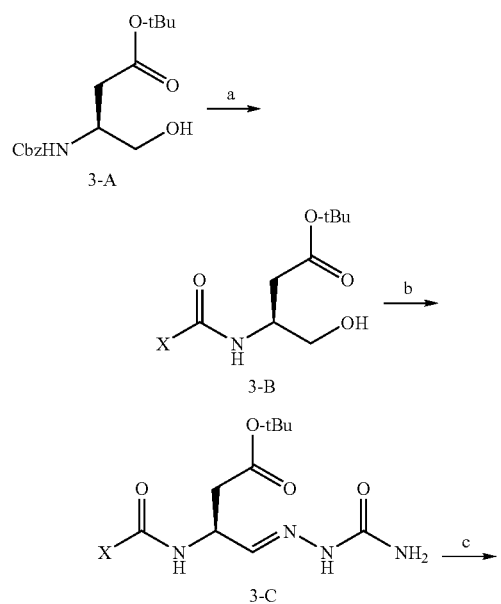

Scheme 3

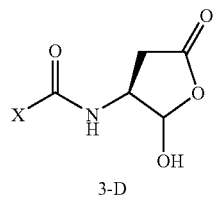

3-D a) i) $H_2$, Pd/C, EtOH; ii) X—COOH or X—COCl, standard amide coupling conditions;
iii) further manipulation of group X;
b) i) Dess-Martin periodinane, DCM; ii) semicarbazide hydrochloride, EtOH/$H_2O$ (2:1), NaOAc
c) i) TFA, anisole, DCM; ii) formaldehyde, AcOH, dioxane or methanol A route to compounds of this invention, wherein $R^5$ is other than hydrogen, is shown in Scheme 4.

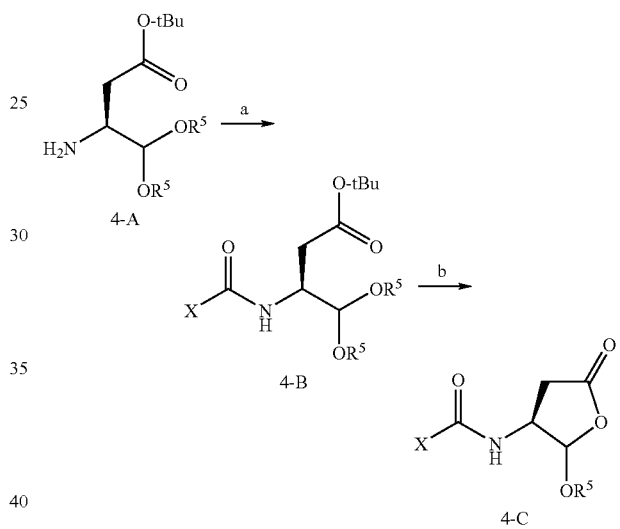

Scheme 4 a) X—COOH or X—COCl, standard amide coupling; further manipulations;
b) TFA, solvent.

The known acetal 4-A (D. S. Karanewsky et al. US 2002/0042376) was coupled to an acid using standard conditions to generate 4-B. After further modifications on the group X, the gamma-carboxyl acetal was cyclized to generate the cyclic acetal 4-C.

An alternative embodiment to the compounds of this invention is shown in scheme 5.

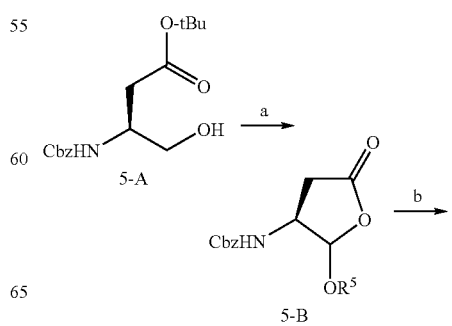

Scheme 5

-continued

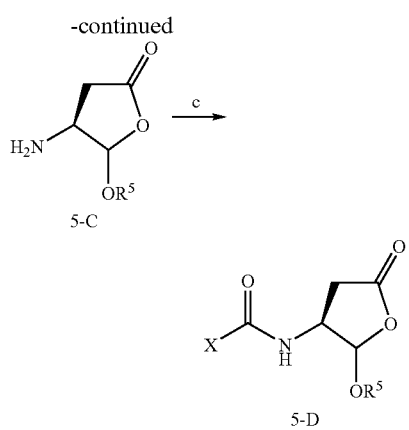

a) i) Dess-Martin periodinane, DCM; ii) [(OR⁵)₃CH, R⁵OH,TsOH]; iii) TFA, DCM, chromatography
b) H₂, Pd/C, solvent;
c) i) X—COOH or X—COCl, standard amide coupling conditions;
   ii) further manipulations on group X.

Cbz-aspartinol t-butyl ester was converted to 5-C using literature methods (D. S. Karanewsky et al. US2002/0042376). The amine 5-C was treated with X—COOH or X—COCl to provide the final conjugate using standard amide coupling conditions.

An illustration of the synthesis of the compounds in the present invention in which X=Q—C(=O)—CR¹H—O— in Formula I, is given in Scheme 6.

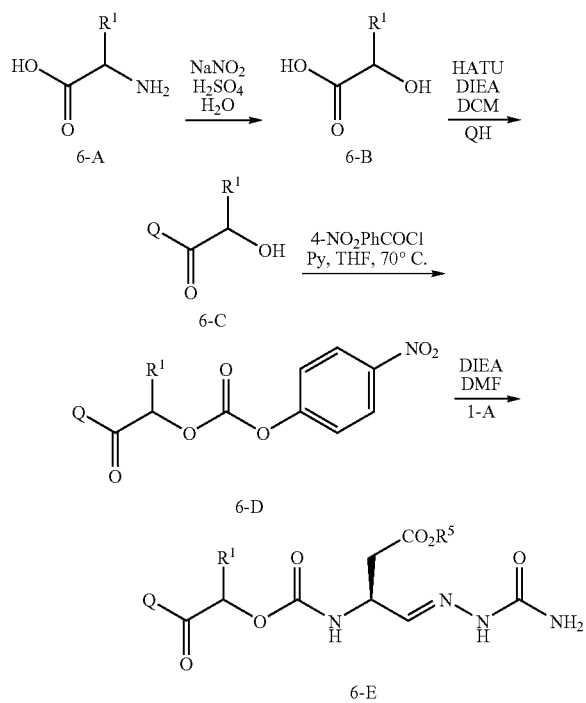

Methods for the synthesis of monosubstituted succinate derivatives are known in the art and are disclosed in a number of references including (a) D. A. Evans et al., *J. Org. Chem.* 1999, 64, 6411; (b) D. W. C. MacMillan et al., *J. Am. Chem. Soc.* 2001, 123, 2912; (c) S. Azam et al., *J. Chem.* *Soc. Perkin Trans. 1* 1996, 621; (d) A. Abell et al., *Org. Lett.* 2002, 4, 3663; (e) R. J. Cherney et al., *Bioorg. Med. Chem. Lett.* 2003, 13, 1297; (f) G. Shapiro et al., *Tetrahedron Lett.* 1992, 33, 2447; (g) N. J. S. Harmat et al., *Tetrahedron Lett.* 2000, 41, 1261. A representative procedure is outlined in Scheme 7, where acylation of an oxazolidinone chiral auxiliary with an acid chloride provides structure 7-A. Alkylation of the corresponding enolate with t-butyl bromoacetate followed by LiOH/H₂O₂ mediated cleavage of the chiral auxiliary gives rise to the enantiomerically pure monosubstituted succinic acid monoester 7-C.

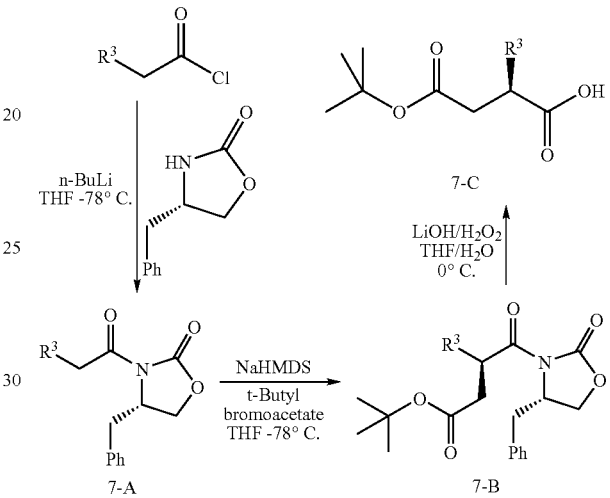

An illustration of the synthesis of the compounds of the present invention, in which X=W—C(=O)—O—CR³H— in Formula I, is given in Scheme 8.

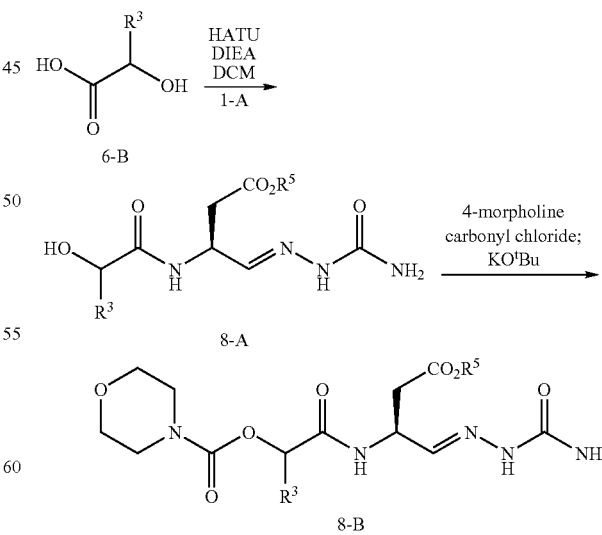

In one embodiment, the compounds in this invention, in which X=R⁶CH₂—CR¹H—O—, can be made as shown in Scheme 9.

Scheme 9

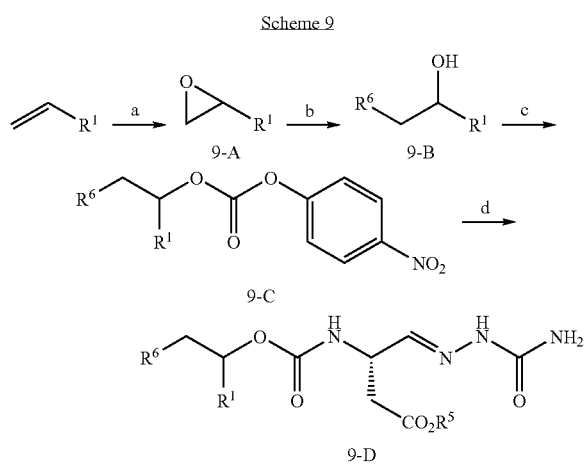

a) MeReO$_3$, H$_2$O$_2$, 3-cyanopyridine, CH$_2$Cl$_2$;
b) Heterocycle R$^6$H, K$_2$CO$_3$, DMF, 160° C., microwave, 6 min;
d) 4-Nitrophenyl chloroformate, pyridine, heat or 4-nitrophenyl chloroformate, DMAP, DMF, heat;
d) 1-A, DMF, DIEA.

An olefin was oxidized to the corresponding epoxide 9-A. Preferred methods for oxidation of olefin to epoxide include, but not limited to, the methyltrioxorhenium method (K. B. Sharpless et al. *Chem. Commun.* 1997, 1565; K. B. Sharpless et al. *J. Am. Chem. Soc.* 1997, 119, 6189), dimethyldioxirane (Adam, W. et al *Acc. Chem. Res.* 1989, 22, 205), peracids (Camps, F. et al. *J. Org. Chem.* 1982, 47, 5402). Enatiomerically enriched epoxides can be obtained via asymmetric dihydroxylation as described in Sharpless, K. B. et al. *Chem. Rev.* 1994, 94, 2483; Sharpless, K. B. et al. In *Catalytic Asymmetric Synthesis* Ojima, I. (Ed.); Wiley-VCH, 2002; 2$^{nd}$ Ed. Pp. 357-398. The epoxide 9-A was then opened to 9-B. If R$^6$ is an NH containing heteroaryl, the reaction was done using powdered potassium carbonate in DMF and microwave irradiation. If R$^6$ is an aliphatic amine, the reaction was done in neat amine using microwave irradiation. Expoxide like synthons such as cyclic sulfates and cyclic sulfites can be used in this transformation (B. B. Lohray *Synthesis* 1992, 1035). The hydroxyl of 9-B was then functionalized as a mixed carbonate 9-C. This was done with 4-nitrophenyl carbonate in pyridine or in DMF with DMAP as base. If these conditions were not tolerated, then the transformation was affected with phosgene in CH$_2$Cl$_2$. As those of skill in the art will recognize, other leaving groups (LG) can also be employed: methods for preparing compounds 9-C wherein LG is Cl are known in the art and may be used instead. Finally, the mixed carbonate 9C was reacted with an amine 1-A in DMF using DIEA as base to afford the desired carbamate 9-D.

Alternative route to compounds described in this invention is shown in Scheme 10.

Scheme 10

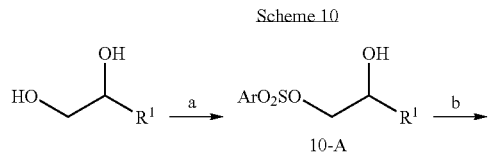

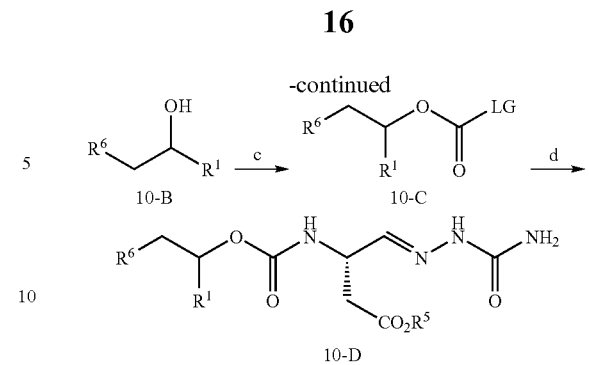

a) ArSO$_2$Cl, pyridine, CH$_2$Cl$_2$;
b) Heterocycle R$^6$H, K$_2$CO$_3$, DMF, 160° C., microwave, 6 min or amine, neat, 160° C. microwave, 6 min;
c) 4-Nitrophenyl chloroformate, pyridine, heat or Nitrophenyl chloroformate, DMAP, DMF, heat or phosgene, CH$_2$Cl$_2$, RT;
d) 1-A, DMF, DIEA.

Starting with a diol (available either through dihydroxylation of terminal olefins or reduction of the appropriate lactic acid), the primary hydroxyl group is selectively sulfonylated to generate 10-A. The terminal carbon is then functionalized using either a heteroaryl anion or an amine to afford 10-B. The secondary alcohol is then activated for carbamate formation using either nitrophenyl chloroformate or phosgene to afford 10-C. As above, other reactive acylating agents such as chloroformnates (10-C, where LG=Cl) may also be used by known methods. This intermediate is then reacted with amine 1-A to furnish the desired 10-D. For the preparation and derivatization of optically pure diols, see Sharpless, K. B. et al. Catalytic asymmetric dihydroxylation *Chem. Rev.* 1994, 94, 2483; Sharpless, K. B. et al. In *Catalytic Asymmetric Synthesis* Ojima, I. (Ed.); Wiley-VCH, 2002; 2$^{nd}$ Ed. Pp. 357-398.

In addition, compounds 6-E, 8-B, 9-D and 10-D can be de-protected as described in Scheme 2 to generates the corresponding cyclic hemiacetal of Formula I.

B. Preferred Compounds

Compounds that inhibit cathepsin S activity can be found in PCT Publications WO 04/084843 and WO 04/084842. The contents of each of the foregoing applications are incorporated herein by reference.

In one aspect, the present invention provides a compound of Formula I:

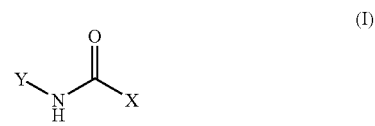

or a pharmaceutically acceptable salt or prodrug thereof, wherein:

Y is a member selected from the group consisting of

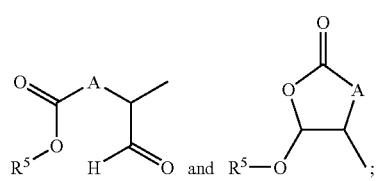

A is a member selected from the group consisting of —CH$_2$—, and —CH$_2$CH$_2$—;

R$^5$ is independently a member selected from the group consisting of H, C$_1$-C$_6$ alkyl, C$_3$-C$_8$ cycloalkyl, C$_1$-C$_4$ alkyl substituted C$_3$-C$_8$ cycloalkyl, and benzyl;

X is a member selected from the group consisting of —O—CR$^1$R$^2$—C(=O)—Q, —CR$^3$H—O—C(=O)—W, —CH$_2$—CHR$^3$—C(=O)—W, —CR$^3$H—CH$_2$—C(=O)—W, —CR$^4$H—NH—C(=O)—W, —O—CR$^1$R$^2$—B—R$^6$, —CR$^3$H—NH—C(=O)—O—Z, —CHR$^4$—NH—C(=O—R$^7$, and —CHR$^4$—NH—S(=O)$_2$—R$^8$;

Q is a heterocycle selected from the group consisting of pyrrolidinyl, piperidyl, morpholinyl, thiomorpholinyl, piperazinyl and indolinyl substituted with 0-2 R$^Q$, wherein Q is connected to —C(=O)— via a ring nitrogen atom;

each R$^Q$ is independently a member selected from the group consisting of OH, —S(=O)$_2$CH$_3$, acetyl, =O, C$_1$-C$_6$ alkyl, C$_1$-C$_6$ alkoxy, CF$_3$, OCF$_3$ and NR$^{10}$R$^{11}$;

W is morpholinyl, wherein W is connected to —C(=O)— via the ring nitrogen atom;

Z is a heterocycle selected from the group consisting of tetrahydrofuranyl, tetrahydropyranyl, thiotetrahydropyranyl, thiotetrahydrofuranyl, pyrrolidinyl, piperidyl, morpholinyl, thiomorpholinyl, piperazinyl and indolinyl each substituted with 0-2 R$^Z$, wherein Z is connected to —O—C(=O)— via a ring carbon atom;

each R$^Z$ is independently a member selected from the group consisting of OH, —S(=O)$_2$CH$_3$, acetyl, =O, C$_1$-C$_6$ alkyl, C$_1$-C$_6$ alkoxy, CF$_3$, OCF$_3$ and NR$^{10}$R$^{11}$;

B is a member selected form the group consisting of —CH$_2$—, —OCH$_2$—, —NR$^{11}$CH$_2$—, —CH$_2$CH$_2$— and a bond;

each R$^1$ is independently a member selected from the group consisting of H, a C$_1$-C$_6$ alkyl substituted with 0-2 R$^{1a}$, wherein said C$_1$-C$_6$ alkyl is optionally substituted with a heteroatom selected from the group consisting of —O—, —S—, —S(=O)—, and —S(=O)$_2$—; a C$_2$-C$_6$ alkenyl, a C$_3$-C$_6$ alkynyl, a C$_3$-C$_7$ cycloalkyl each substituted with 0-2 R$^{1b}$, and a C$_7$-C$_{11}$ bicycloalkyl substituted with 0-2 R$^{1b}$; phenyl substituted with 0-3 R$^{1c}$, a 5- to 6-membered heteroaryl containing 1 to 4 heteroatoms each independently a member selected from the group consisting of N, O and S, wherein said heteroaryl is substituted with 0-3 R$^{1c}$;

each R$^{1a}$ is independently a member selected from the group consisting of a C$_6$-C$_{10}$ aryl substituted with 0-3 R$^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 R$^{1c}$, a C$_3$-C$_8$ cycloalkyl substituted with 0-2 R$^{1b}$, a C$_7$-Cl$_1$ bicycloalkyl substituted with 0-2 R$^{1b}$, and a C$_1$-C$_3$ perfluoroalkyl;

each R$^{1b}$ is independently a member selected from the group consisting of a H, C$_1$-C$_6$ alkyl, C$_1$-C$_6$ alkoxy, CF$_3$, OCF$_3$, —S(=O)$_2$CH$_3$, and acetyl;

each R$^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, C$_1$-C$_6$ alkoxy, C$_1$-C$_3$ perfluoroalk C$_1$-C$_3$ perfluoroalkoxy and a C$_1$-C$_6$ alkyl;

each R$^2$ is independently a member selected from the group consisting of H and C$_1$-C$_6$ alkyl;

each R$^3$ is a C$_1$-C$_2$ alkyl substituted with 1 R$^{3a}$;

each R$^{3a}$ is independently a member selected from the group consisting of a C$_3$-C$_7$ cycloalkyl substituted with 0-2 R$^{1b}$, and a C$_7$-C$_{11}$ bicycloalkyl substituted with 0-2 R$^{1b}$;

each R$^4$ is a C$_1$-C$_2$ alkyl substituted with 1 R$^{4a}$;

each R$^{4a}$ is independently a member selected from the group consisting of a tert-butyl, a C$_3$-C$_7$ cycloalkyl substituted with 0-2 R$^{1b}$, and a C$_7$-C$_{11}$ bicycloalkyl substituted with 0-2 R$^{1b}$;

R$^6$ is independently a member selected from group consisting of a 5- to 6-membered monocyclic heteroaryl containing 1 to 4 heteroatoms each independently a member selected from the group consisting of N, O and S, wherein said heteroaryl is substituted with 1 R$^{6a}$ and 0-2 R$^{1c}$; and a 8- to 10-membered bicyclic heteroaryl containing 1 to 4 heteroatoms each independently a member selected from the group consisting of N, O and S, wherein said heteroaryl is substituted with 0-3 R$^{1c}$;

each R$^{6a}$ is independently a member selected from the group consisting of phenyl substituted with 0-3 R$^{1c}$; a 5- to 6-membered heteroaryl containing 1 to 4 heteroatoms each independently a member selected from the group consisting of N, O and S, wherein said heteroaryl is substituted with 0-3 R$^{1c}$;

R$^7$ is a member selected from the group consisting of a 5-membered heteroaryl containing 1 to 4 heteroatoms each independently a member selected from the group consisting of N, O and S, wherein said heteroaryl is substituted with 1 R$^{6a}$ and 0-2 R$^{1c}$; a phenyl substituted with 0-3 R$^{1c}$, OCH$_2$Ph, O-tert-Bu, and C$_3$-C$_6$ cycloalkyl;

R$^8$ is a member selected from the group consisting of a phenyl substituted with 0-3 R$^{1c}$, and a 5- to 6-membered heteroaryl containing 1 to 4 heteroatoms each independently a member selected from the group consisting of N, O and S, wherein said heteroaryl is substituted with 0-3 R$^{1c}$;

each R$^{10}$ is independently a member selected from the group consisting of H, C$_1$-C$_4$ alkyl, (C$_1$-C$_4$ alkyl)-C(=O)— and (C$_1$-C$_4$ alkyl)—S(=O)$_2$—;

each R$^{11}$ is independently a member selected from the group consisting of H and C$_1$-C$_4$ alkyl; and each R$^{12}$ is independently a member selected from the group consisting of H and C$_1$-C$_4$ alkyl.

In a preferred aspect, the present invention provides a compound of Formula Ia:

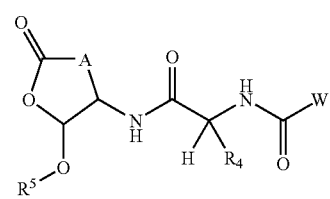

Ia wherein:

A is —CH$_2$—;

R$^4$ is a C$_1$-C$_2$ alkyl substituted with 1 R$^{4a}$;

R$^{4a}$ is selected from the group consisting of a tert-butyl, a C$_3$-C$_7$ cycloalkyl substituted with 0-2 R$^{1b}$, and a C$_7$-C$_1$I bicycloalkyl substituted with 0-2 R$^{1b}$;

each $R^{1b}$ is independently selected from the group consisting of a H, $C_1$-$C_6$ alkyl, $C_1$-$C_6$ alkoxy, $CF_3$, $OCF_3$, —S(=O)$_2$CH$_3$, and acetyl; and W is morpholinyl, wherein W is connected to —C(=O)— via the ring nitrogen atom.

In another preferred aspect, the present invention provides a compound of Formula Ib:

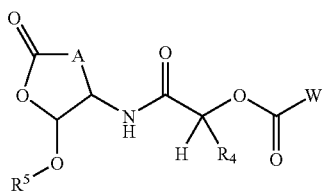

Ib wherein:

A is —CH$_2$—;

$R^3$ is a $C_1$-$C_2$ alkyl substituted with 1 $R^{3a}$;

$R^{3a}$ is selected from the group consisting of a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —S(=O)$_2$CH$_3$, and acetyl; and W is morpholinyl, wherein W is connected to —C(=O)— via the ring nitrogen atom.

In yet another aspect, the present invention provides a compound of Formula Ic:

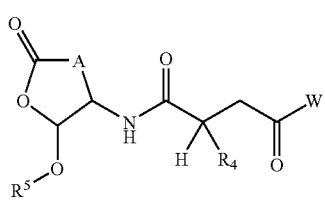

Ic wherein:

A is —CH$_2$—;

$R^3$ is a $C_1$-$C_2$ alkyl substituted with 1 $R^{3a}$;

$R^{3a}$ is selected from the group consisting of a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —S(=O)$_2$CH$_3$, and acetyl; and W is morpholinyl, wherein W is connected to —C(=O)— via the ring nitrogen atom.

In still yet another aspect, the present invention provides a compound of Formula Id:

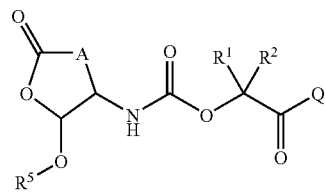

Id wherein:

A is —CH$_2$—;

$R^1$ is independently a member selected from the group consisting of H, a $C_1$-$C_6$ alkyl substituted with 0-2 $R^{1a}$, wherein said $C_{11}$-$C_6$ alkyl is optionally substituted with a heteroatom selected from the group consisting of —O—, —S—, —S(=O)— and —S(=O)$_2$—; a $C_2$-$C_6$ alkenyl, a $C_3$-$C_6$ alkynyl, a $C_3$-$C_7$ cycloalkyl each substituted with 0-2 $R^{1b}$, and a $C_7$-$C_1$ bicycloalkyl substituted with 0-2 $R^{1b}$; phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;

each $R^{1a}$ is independently a member selected from the group consisting of a $C_6$-$C_{10}$ aryl substituted with 0-3 $R^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1c}$, a $C_3$-$C_8$ cycloalkyl substituted with 0-2 $R^{1b}$, a $C_7$-$C_{11}$ bicycloalkyl substituted with 0-2 $R^{1b}$, and a $C_1$-$C_3$ perfluoroalkyl;

each $R^{1b}$ is independently a member selected from the group consisting of a H, $C_1$-$C_6$ alkyl, $C_1$-$C_6$ alkoxy, $CF_3$, $OCF_3$, —S(=O)$_2$CH$_3$, and acetyl;

each $R^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, $C_1$-$C_6$ alkoxy, $C_1$-$C_3$ perfluoroalk, $C_1$-$C_3$ perfluoroalkoxy and a $C_1$-$C_6$ alkyl;

each $R^2$ is independently a member selected from the group consisting of H and $C_1$-$C_6$ alkyl;

Q is a heterocycle selected from the group consisting of pyrrolidinyl, piperidyl, morpholinyl, thiomorpholinyl, piperazinyl and indolinyl substituted with 0-2 $R^Q$, wherein Q is connected to —C(=O)— via a ring nitrogen atom; and each $R^Q$ is independently a member selected from the group consisting of OH, —S(=O)$_2$CH$_3$, acetyl, =O, $C_1$-$C_6$ alkyl, $C_1$-$C_6$ alkoxy, $CF_3$, $OCF_3$ and NR$^{10}$R$^{11}$.

In especially preferred aspects, the compounds of Formula Id are of the formula wherein:

$R^1$ is a $C_1$-$C_2$ alkyl substituted with 1 $R^{4a}$;

$R^{4a}$ is selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently a member selected from the group consisting of a H, $C_1$-$C_6$ alkyl, $C_1$-$C_6$ alkoxy, $CF_3$, $OCF_3$, —S(=O)$_2$CH$_3$, and acetyl;

$R^2$ is H; and

Q is selected from the group of a morpholinyl, pyrrolidinyl, piperidyl, and piperazinyl, wherein Q is connected to —C(=O)— via a ring nitrogen.

In another preferred aspect, the present invention provides a compound of Formula Ie:

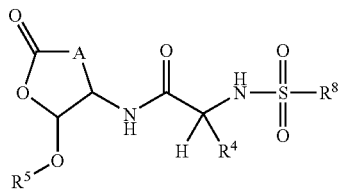

Ie wherein:

A is —CH$_2$—;

$R^4$ is a $C_1$-$C_2$ alkyl substituted with 1 $R^{4a}$;

$R^{4a}$ is selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —S(=O)$_2$CH$_3$, and acetyl;

$R^8$ is a member selected from the group consisting of a phenyl substituted with 0-3 $R^{1c}$, and a 5- to 6-membered heteroaryl containing 1 to 4 heteroatoms each independently a member selected from the group consisting of N, O and S, wherein said heteroaryl is substituted with 0-3 $R^{1c}$; and each $R^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, $C_1$-$C_6$ alkoxy, $C_1$-$C_3$ perfluoroalkyl, $C_1$-$C_3$ perfluoroalkoxy and a $C_1$-$C_6$ alkyl.

In yet another preferred aspect, the present invention provides a compound of Formula If:

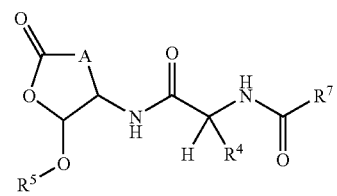

If wherein:

A is —CH$_2$—;

$R^4$ is a $C_1$-$C_2$ alkyl substituted with 1 $R^{4a}$.

$R^{4a}$ is selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —S(=O)$_2$CH$_3$, and acetyl;

$R^7$ is a member selected from the group consisting of a 5-membered heteroaryl containing 1 to 4 heteroatoms each independently a member selected from the group consisting of N, O and S, wherein said heteroaryl is substituted with 1 $R^{6a}$ and 0-2 $R^{1c}$; a phenyl substituted with 0-3 $R^{1c}$, OCH$_2$Ph, O-tert-Bu, and $C_3$-$C_6$ cycloalkyl;

each $R^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, $C_1$-$C_6$ alkoxy, $C_1$-$C_3$ perfluoroalkyl, $C_1$-$C_3$ perfluoroalkoxy and a $C_1$-$C_6$ alkyl; and each $R^{6a}$ is independently a member selected from the group consisting of phenyl substituted with 0-3 $R^{1c}$; a 5- to 6-membered heteroaryl containing 1 to 4 heteroatoms each independently a member selected from the group consisting of N, O and S, wherein said heteroaryl is substituted with 0-3 $R^{1c}$.

In still yet another preferred aspect, the present invention provides a compound of Formula Ig:

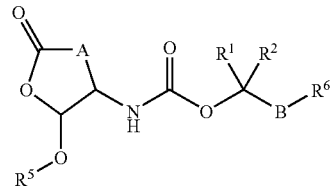

Ig wherein:

A is —CH$_2$—;

each $R^1$ is independently a member selected from the group consisting of H, a $C_1$-$C_6$ alkyl substituted with 0-2 $R^{1a}$, wherein said $C_1$-$C_6$ alkyl is optionally substituted with a heteroatom selected from the group consisting of —O—, —S—, —S(=O)— and —S(=O)$_2$—; a $C_2$-$C_6$ alkenyl, a $C_3$-$C_6$ alkynyl, a $C_3$-$C_7$ cycloalkyl each substituted with 0-2 $R^{1b}$, and a $C_7$-$C_{11}$ bicycloalkyl substituted with 0-2 $R^{1b}$; phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;

each $R^{1a}$ is independently a member selected from the group consisting of a $C_6$-$C_{10}$ aryl substituted with 0-3 $R^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1c}$, a $C_3$-$C_8$ cycloalkyl substituted with 0-2 $R^{1b}$, a $C_7$-$C_{11}$ bicycloalkyl substituted with 0-2 $R^{1b}$, and a $C_1$-$C_3$ perfluoroalkyl;

each $R^{1b}$ is independently a member selected from the group consisting of a H, $C_1$-$C_6$ alkyl, $C_1$-$C_6$ alkoxy, $CF_3$, $OCF_3$, —S(=O)$_2$CH$_3$, and acetyl;

each $R^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, $C_1$-$C_6$ alkoxy, $C_1$-$C_3$ perfluoroalkyl, $C_1$-$C_3$ perfluoroalkoxy and a $C_1$-$C_6$ alkyl;

each $R^2$ is independently a member selected from the group consisting of H and $C_1$-$C_6$ alkyl;

B is a member selected form the group consisting of —CH$_2$—, —OCH$_2$—, —NR$^{11}$CH$_2$—, —CH$_2$CH$_2$— and a bond;

R$^6$ is independently a member selected from group consisting of a 5- to 6-membered monocyclic heteroaryl containing 1 to 4 heteroatoms each independently a member selected from the group consisting of N, O and S, wherein said heteroaryl is substituted with 1 R$^{6a}$ and 0-2 R$^{1c}$; and a 8- to 10-membered bicyclic heteroaryl containing 1 to 4 heteroatoms each independently a member selected from the group consisting of N, O and S, wherein said heteroaryl is substituted with 0-3 R$^{1c}$; and each R$^{6a}$ is independently a member selected from the group consisting of phenyl substituted with 0-3 R$^{1c}$; a 5- to 6-membered heteroaryl containing 1 to 4 heteroatoms each independently a member selected from the group consisting of N, O and S, wherein said heteroaryl is substituted with 0-3 R$^{1c}$.

In especially preferred aspects, the compounds of Formula Ig are of the formula wherein:

R$^1$ is a C$_1$-C$_2$ alkyl substituted with 1 R$^{4a}$;

R$^{4a}$ is selected from the group consisting of a tert-butyl, a C$_3$-C$_7$ cycloalkyl substituted with 0-2 R$^{1b}$, and a C$_7$-C$_{11}$ bicycloalkyl substituted with 0-2 R$^{1b}$;

each R$^{1b}$ is independently a member selected from the group consisting of a H, C$_1$-C$_6$ alkyl, C$_1$-C$_6$ alkoxy, CF$_3$, OCF$_3$, —S(=O)$_2$CH$_3$, and acetyl;

R$^2$ is H;

R$^6$ is a 8- to 10-membered bicyclic heteroaryl containing 1 to 4 heteroatoms each independently a member selected from the group consisting of N, O and S, wherein said heteroaryl is substituted with 0-3 R$^{1c}$; and B is —CH$_2$—.

In yet another especially preferred aspect, the compounds have Formula Ih:

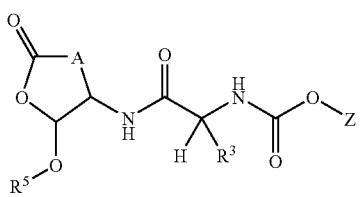

Ih wherein:

A is —CH$_2$—.

Preferred compounds of Formula I are set forth below:

1. (3S)-(3-Cyclopentyl-(2S)-{[5-(3-fluoro-phenyl)-furan-2-carbonyl]-amino}-propionylamino)-4-oxo-butyric acid;
2. (3S)-{3-Cyclopentyl-(2S)-[(morpholine-4-carbonyl)-amino]-propionylamino}-4-oxo-butyric acid;
3. (3S)-{3-cyclohexyl-(2S)-(morpholine-4-carbonyloxy)-propionylamino}-4-oxo-butyric acid;
4. (3S)-[(2R)-Cyclopentylmethyl-4-morpholin-4-yl-4-oxo-butyrylamino]-4-oxo-butyric acid;
5. (3S)-[(1S)-Cyclopentylmethyl-2-(5,6-dichloro-benzoimidazol-1-yl)-ethoxycarbonylamino]-4-oxo-butyric acid;
6. (3S)-{(2R)-Cyclohexylmethyl-4-morpholin-4-yl-4-oxo-butyrylamino}-4-oxo-butyric acid;
7. (3S)-[3-Cyclohexyl-(2S)-(3-trifluoromethoxy-benzenesulfonylamino)-propionylamino]-4-oxo-butyric acid;
8. (3S)-[3-Cyclopentyl-(2S)-(3-trifluoromethoxy-benzenesulfonylamino)-propionylamino]-4-oxo-butyric acid;
9. (3S)-[3,3-Dimethyl-(1S)-(morpholine-4-carbonyl)-butoxycarbonylamino]-4-oxo-butyric acid;
10. (3S)-[2-cyclohexyl-(1S)-(morpholin-4-carbonyl)-ethoxycarbonylamino]-4-oxo-butyric acid;
11. (3S)-[(2S)-benzyloxycarbonylamino-3-cycohexyl-propionylamino]-2-benzyloxy-5-oxo-tetrahydrofuran;
12. (3S)-[3-Cyclopentyl-(2S)-{[5-(3-fluoro-phenyl)-furan-2-carbonyl]-amino}propionylamino]2-ethoxy-5-oxo-tetrahydrofuran;
13. (3S)-[(2S)-t-butoxycarbonylamino-4,4-dimethyl-pentanoylamino]-(2R)-ethoxy-5-oxo-tetrahydrofuran;
14. (3S)-[3-Cyclopentyl-(2S)-{[5-(3-fluoro-phenyl)-furan-2-carbonyl]-amino}propionylamino]-(2R)-ethoxy-5-oxo-tetrahydrofuran;
15. (3S)-(3-Cyclohexyl-(2S)-{[5-(3-fluoro-phenyl)-furan-2-carbonyl]-amino}-propionylamino)-4-oxo-butyric acid;
16. (3S)-[3-Cyclohexyl-(2S)-{[5-(3-fluoro-phenyl)-furan-2-carbonyl]-amino}propionylamino]-2-methoxy-5-oxo-tetrahydrofuran;
17. (3S)-[3-Cyclohexyl-(2S)-{[5-(3-fluoro-phenyl)-furan-2-carbonyl]-amino}propionylamino]-2-ethoxy-5-oxo-tetrahydrofuran;
18. (3S)-((2S)-(3-cyanophenyl-carbonylamino)-3-cyclopentyl-propionylamino)-4-oxo-butyric acid;
19. (3S)-(3-Cyclopentyl-(2S)-(cyclopropylcarbonylamino)-propionylamino)-4-oxo-butyric acid;
20. (3S)-(3-Cyclopentyl-(2S)-(tetrahydro-pyran-4-yloxycarbonylamino)-propionylamino)-4-oxo-butyric acid;
21. (3S)-(3-Cyclopropyl-(2S)-(cyclopropylcarbonylamino)-propionylamino)-4-oxo-butyric acid;
22. (3S)-((2S)-(cyclopropylcarbonylamino)-4,4-dimethyl-pentanoylamino)-4-oxo-butyric acid;
23. (3S)-(3-Cyclopentyl-(2S)-{[5-(3-trifluoromethyl-phenyl)-furan-2-carbonyl]-amino}-propionylamino)-4-oxo-butyric acid;
24. (3S)-(3-Cyclopentyl-(2S)-(3-trifluoromethylphenyl-carbonylamino)-propionylamino)-4-oxo-butyric acid;
25. (3S)-[3-Cyclopentyl-(2S)-{[5-(3-fluoro-phenyl)-furan-2-carbonyl]-amino}propionylamino]-2-isopropoxy-5-oxo-tetrahydrofuran;
26. (3S)-[3-Cyclopentyl-(2S)-{[5-(3-fluoro-phenyl)-furan-2-carbonyl]-amino}propionylamino]-2-cyclopentoxy-5-oxo-tetrahydrofuran; and
27. (3S)-[3-Cyclopentyl-(2S)-{[5-(3-fluoro-phenyl)-furan-2-carbonyl]-amino}propionylamino]-2-cyclopentylmethoxy-5-oxo-tetrahydrofuran.

Compounds of the present invention are either obtained in the free form, or as a salt thereof if salt forming groups are present, or as esters if ester forming groups are present.

Compounds of the present invention that have acidic groups can be converted into salts with pharmaceutically acceptable bases, e.g., an aqueous alkali metal hydroxide, advantageously in the presence of an ethereal or alcoholic solvent, such as a lower alkanol. Resulting salts can be converted into the free compounds, e.g., by treatment with acids. These, or other salts can also be used for purification of the compounds obtained. Ammonium salts are obtained by reaction with the appropriate amine, e.g., diethylamine, and the like.

In certain aspects, compounds of the present invention having basic groups can be converted into acid addition salts, especially pharmaceutically acceptable salts. These are formed, for example, with inorganic acids, such as mineral acids, for example, sulfuric acid, a phosphoric or hydrohalic acid, or with organic carboxylic acids, such as $(C_1-C_4)$ alkane carboxylic acids which, for example, are unsubstituted or substituted by halogen, for example, acetic acid, such as saturated or unsaturated dicarboxylic acids, for example, oxalic, succinic, maleic or fumaric acid, such as hydroxycarboxylic acids, for example, glycolic, lactic, malic, tartaric or citric acid, such as amino acids, for example, aspartic or glutamic acid, or with organic sulfonic acids, such as $(C_1-C_4)$-alkylsuflonic acids (for example, methanesulfonic acid) or arylsulfonic acids which are unsubstituted or substituted (for example, by halogen). Preferred are salts formed with hydrochloric acid, methanesulfonic acid and maleic acid.

In view of the close relationship between the free compounds and the compounds in the form of their salts or esters, whenever a compound is referred to in this context, a corresponding salt or ester is also intended, provided such is possible or appropriate under the circumstances.

The compounds, including their salts, can also be obtained in the form of their hydrates, or include other solvents used for their crystallization.

The compounds of the present invention that comprise free hydroxyl groups may also exist in the form of pharmaceutically acceptable, physiologically cleavable esters, and as such are included within the scope of the invention. Such pharmaceutically acceptable esters are preferably prodrug ester derivatives, such being convertible by solvolysis or cleavage under physiological conditions to the corresponding compounds of the present invention which comprise free hydroxyl groups. Suitable pharmaceutically acceptable prodrug esters are those derived from a carboxylic acid, a carbonic acid monoester or a carbamic acid, preferably esters derived from an optionally substituted lower alkanoic acid or an arylcarboxylic acid.

As will be apparent to one of skill in the art, certain compounds of the present invention possess asymmetric carbon atoms (optical centers) or double bonds; the racemates, diastereomers, enantiomers, geometric isomers and individual isomers are all intended to be encompassed within the scope of the present invention.

The present invention provides compounds which inhibit cathepsin S selectively. In certain preferred aspects, the present invention provides compounds which selectively inhibit cathepsin S in the presence of cathepsin isozymes, such as cathepsin A, B, C, D, E, F, G, H, K, L, M, O, P, Q, R, V, W and X. In a more preferred aspect, the present invention provides compounds which selectively inhibit cathepsin S in the presence of cathepsin K, L, B, or combinations thereof. In certain preferred aspects, the compounds of the present invention do not inhibit caspase, such as caspase-1, -3 or -8.

Compounds of the present invention useful for treating cathepsin S dependent conditions, preferably have cathepsin S inhibition constants less than 10 μM. More preferably, compounds of the present invention useful for treating cathepsin S dependent conditions have cathepsin S inhibition constants of less than 1.0 μM. Most preferably, compounds of the present invention useful for treating cathepsin S dependent conditions have cathepsin S inhibition constants of less than 0.1 μM.

In a preferred aspect, compounds of the present invention that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

In certain aspects, the inhibition constant a compound of Formula I for at least one caspase is at least 10 times greater than the inhibition constant for at least one cathepsin S. Preferably, the inhibition constant of a compound of Formula I for at least one caspase is at least 100 times greater than the inhibition constant for at least one cathepsin S. More preferably, the inhibition constant of a compound of Formula I for at least one caspase is at least 1000 times greater than the inhibition constant for at least one cathepsin S. Yet more preferably, the inhibition constant of a compound of Formula I for at least one caspase is at least 10,000 times greater than the inhibition constant for at least one cathepsin S.

IV. Compositions

The pharmaceutical compositions according to the invention are those suitable for enteral, such as oral or rectal, transdermal, topical, and parenteral administration to mammals, including humans, to inhibit cathepsin S activity, and for the treatment of cathepsin S dependent disorders, in particular chronic neuropathic pain (see, WO 03/020287), Alzheimer's disease and certain autoimmune disorders, including, but not limited to, juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to, asthma; and allogeneic immune responses, including, but not limited to, rejection of organ transplants or tissue grafts.

More particularly, the pharmaceutical compositions comprise an effective cathepsin S inhibiting amount of a compound of the present invention.

The pharmacologically active compounds of the present invention are useful in the manufacture of pharmaceutical compositions comprising an effective amount thereof in conjunction or mixture with excipients or carriers suitable for either enteral or parenteral application.

Preferred are tablets and gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and contain about 0.1 to 75%, preferably about 1 to 50%, of the active ingredient.

Tablets may be either film coated or enteric coated according to methods known in the art.

Suitable formulations for transdermal application include an effective amount of a compound of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical formulations contain an effective cathepsin S inhibiting amount of a compound of the present invention as defined above, either alone or in combination with another therapeutic agent.

In conjunction with another active ingredient, a compound of the present invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50 to 70 kg may contain between about 5 and 500 mg of the active ingredient.

In a preferred aspect, the pharmaceutical composition of the present invention provides a compound according to Formula I.

In one aspect of the present invention, compositions of the present invention that comprise compounds of the present invention and pharmaceutically acceptable excipients, selectively inhibit cathepsin S in the presence of other cathepsin isozymes. In a more preferred aspect, the present invention provides compositions which selectively inhibit cathepsin S in the presence of cathepsin K, L, B, or combinations thereof. In certain preferred aspects, the compounds in the compositions of the present invention do not inhibit caspase, such as caspase-1, -3 or -8.

In another aspect of the present invention, compositions of the present invention useful for treating cathepsin S dependent conditions, preferably have cathepsin S inhibition constants less than 10 µM. More preferably, compositions of the present invention useful for treating cathepsin S dependent conditions have cathepsin S inhibition constants of less than 1.0 µM. Most preferably, compositions of the present invention useful for treating cathepsin S dependent conditions have cathepsin S inhibition constants of less than 0.1 µM.

In a preferred aspect, compositions of the present invention utilize compounds that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

V. Methods

In view of their activity as inhibitors of cathepsin S, compounds of the present invention are particularly useful in mammals as agents for treatment and prophylaxis of diseases and medical conditions involving elevated levels of cathepsin S. For example, the compounds of the present invention are useful in treating Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogeneic immune responses, including, but not limited to, rejection of organ transplants or tissue grafts.

Beneficial effects are evaluated in vitro and in vivo pharmacological tests generally known in the art, and as illustrated herein.

The above cited properties are demonstrable in vitro and in vivo tests, using advantageously mammals, e.g., rats, mice, dogs, rabbits, monkeys or isolated organs and tissues, as well as mammalian enzyme preparations, either natural or prepared by, e.g., recombinant technology. Compounds of the present invention can be applied in vitro in the form of solutions, e.g., preferably aqueous solutions or suspensions, and in vivo either enterally or parenterally, preferably orally, e.g., as a suspension or in aqueous solution, or as a solid capsule formulation. In vitro dosages may range between about $10^{-5}$ molar and $10^{-9}$ molar concentrations. The dosage in vivo may range, depending on the route of administration, between about 0.1 and 100 mg/kg.

The antiarthritic efficacy of the compounds of the present invention for the treatment of rheumatoid arthritis can be determined using models such as, or similar to, the rat model of adjuvant arthritis, as described previously (R. E. Esser, et al, *J. Rheumatology* 1993, 20, 1176). The efficacy of the compounds of the present invention for the treatment of osteoarthritis can be determined using models such as, or similar to, the rabbit partial lateral meniscectomy model, as described previously (Colombo et al., *Arth. Rheum.* 1993, 26, 875-886). The efficacy of the compounds in the model can be quantified using histological scoring methods, as described previously (O'Byrne et al., *Inflamm. Res.* 1995, 44, S 177-S118).

The present invention also relates to methods of using compounds of the present invention and their pharmaceutically acceptable salts, or pharmaceutical compositions thereof, in mammals for inhibiting cathepsin S, and for the treatment of cathepsin S dependent conditions, such as the cathepsin S dependent conditions described herein, e.g., inflammation, rheumatoid arthritis and osteoarthritis.

In a preferred aspect, the present invention relates to a method of treating rheumatoid arthritis, osteoarthritis, and inflammation (and other diseases as identified above) in mammals comprising administering to a mammal in need thereof, a correspondingly effective amount of a compound of the present invention.

In a preferred aspect, the method of the present invention provides a compound according to Formula I.

Methods of the present invention useful for treating cathepsin S dependent conditions, preferably use compounds that have cathepsin S inhibition constants less than 10 μM. More preferably, methods of the present invention useful for treating cathepsin S dependent conditions use compounds that have cathepsin S inhibition constants of less than 1.0 μM. Most preferably, methods of the present invention useful for treating cathepsin S dependent conditions use compounds that have cathepsin S inhibition constants of less than 0.1 μM.

Moreover, the present invention relates to a method of selectively inhibiting cathepsin S activity in a mammal which comprises administering to a mammal in need thereof, an effective cathepsin S inhibiting amount of a compound of the present invention. In a preferred aspect, the methods of the present invention use compounds that selectively inhibit cathepsin S in the presence of a cathepsin isozyme, such as cathepsin A, B, C, D, E, F, G, H, K, L, M, O, P, Q, R, V, W and X. In a more preferred aspect, methods of the present invention use compounds that selectively inhibit cathepsin S in the presence of cathepsin K, L, B, or combinations thereof. In certain preferred aspects, the compounds in the methods of the present invention do not inhibit caspase, such as caspase-1, -3 or -8.

In a preferred aspect, methods of the present invention use compounds that selectively inhibit cathepsin S in the presence of a cathepsin isozyme, have a cathepsin isozyme inhibition constant at least 10 times greater than their cathepsin S inhibition constant. In a more preferred aspect, compounds of the present invention that selectively inhibit cathepsin S in the presence of cathepsin isozyme, have a cathepsin isozyme inhibition constant at least 100 times greater than their cathepsin S inhibition constant. In a most preferred aspect, compounds of the present invention that selectively inhibit cathepsin S in the presence of cathepsin isozyme, have a cathepsin isozyme inhibition constant at least 1000 times greater than their cathepsin S inhibition constant.

In certain aspects, methods of the present invention provide compounds wherein the inhibition constant for at least one caspase is at least 10 times greater than the inhibition constant for at least one cathepsin S. Preferably, the methods provide an inhibition constant of a compound of Formula I for at least one caspase that is at least 100 times greater than the inhibition constant for at least one cathepsin S. More preferably, the methods provide an inhibition constant of a compound of Formula I for at least one caspase that is at least 1000 times greater than the inhibition constant for at least one cathepsin S. Yet more preferably, the methods provide an inhibition constant of a compound of Formula I for at least one caspase that is at least 10,000 times greater than the inhibition constant for at least one cathepsin S.

VI. EXAMPLES

A. Compounds

General Procedure. All solvents stated as anhydrous were purchased that way from the manufacturer and used as received. All other purchased reagents were used as received. Unless otherwise stated, all reactions were carried out under a positive pressure of nitrogen. Silica gel chromatography was performed using pre-packed cartridges and an instrument for making a linear solvent gradient along with automated fraction collection. $^1$H NMR spectral data were reported as follows: chemical shift on the δ scale (using residual protio solvent as the internal standard), multiplicity (s=singlet, d=doublet, t=triplet, q=quartet, m=multiplet), integration and coupling constant in hertz. $^{13}$C spectra were recorded as APT experiments and were reported in ppm with residual solvent for internal standard.

Preparation 1. (3S)-amino-4-oxobutanoic acid t-butyl ester semicarbazone, p-toluenesulfonate salt.

The title compound was prepared according to the procedure described in WO 00/01666 (D. S. Karanewsky et al.).

Preparation 2. (S)-2-hydroxy-3-cyclohexylpropionic acid.

To a stirring suspension of L-cyclohexylalanine (4.00 g, 23.4 mmol) in 0.5M $H_2SO_4$ (120 mL) at 0° C. was slowly added dropwise an aqueous solution of $NaNO_2$ (12.1 g in 40 mL $H_2O$). Addition was complete after approximately 1 h, at which point the solution was allowed to warm to room temperature. After 16 h, the reaction mixture was extracted with ether (3×100 mL), and the combined organic extracts were washed with 1M $NaHSO_4$ (1×200 mL) and brine (1×100 mL) and then dried over anhydrous $Na_2SO_4$. The solvent was removed in vacuo, and the crude product was recrystallized from $Et_2O$/pentane (10 mL/100 mL) to afford 2.1 g (52% yield) of (S)-2-hydroxy-3-cyclohexylpropionic acid as fine white needles.

Preparation 3. 2-cyclohexyl-(1S)-(morpholin-4-carbonyl)-ethyl 4-nitrophenyl carbonate.

To a stirring solution of (S)-2-hydroxy-3-cyclohexylpropionic acid (300 mg, 1.74 mmol), morpholine (0.15 mL, 1.74 mmol), and DIEA (0.91 mL, 5.23 mmol) in $CH_2Cl_2$ (3 mL) was added HATU (728 mmol, 1.92 mmol) and the reaction mixture was stirred at room temperature overnight. EtOAc (100 mL) was added and the solution was washed with sat'd $NaHCO_3$ (2×100 mL), brine (1×100 mL), dried over $Na_2SO_4$, and concentrated in vacuo to afford the corresponding amide as a colorless oil which was used without purification.

The resulting amide (1.74 mmol) was dissolved in pyridine (5 mL) and 4-nitrophenyl chloroformate (405 mg, 2.21 mmol) was added. The reaction mixture was stirred at 70° C. for 4h at which point the starting material had disappeared by LCMS. The reaction was then cooled to room temperature, EtOAC (100 mL) was added, the organic layer was washed with 1M $NaHSO_4$, and dried over $Na_2SO_4$. The crude material was purified by silica gel chromatography (hexanes/EtOAc) to afford 550 mg (78% yield, over two steps) of the nitrophenyl carbonate as a white powder.

Preparation 4. 1-(S)-cyclopentylmethyl-2-(5,6-dichlorobenzoimidazol-1-yl)-ethyl 4-nitrophenyl carbonate.

Step A. Preparation of (S)-2,4,6-Triisopropyl-benzenesulfonic acid 3-cyclopentyl-2-hydroxy-propyl ester. A flask was charged with t-BuOH (250 mL), water (250 mL), (DHQ)$_2$PYR (440 mg, 0.50 mmol), $K_3Fe(CN)_6$ (49.5 g, 0.15 mol), $K_2CO_3$ (21 g, 0.15 mol) and $K_2OsO_4.2H_2O$ (70 mg, 0.19 mmol) and stirred until most of the salts dissolved. The flask was then cooled to 4° C. and allyl cyclopentane (5 g, 45 mmol) was added. The reaction was stirred overnight at 4° C. and quenched by addition of $Na_2SO_3$ (50 g). After stirring at room temperature for 1.5 hours, the volatiles were removed in vacuo. The resulting material was partitioned between ethyl acetate and water. The aqueous layer was extracted with ethyl acetate twice more and the combined organics were dried over $MgSO_4$ and the solvent was removed. The resulting oil was chromatographed over silica using 80% ethyl acetate in hexane to afford 4.81 g (74% of diol). A sample (1.21 g, 8.4 mmol) of this material was dissolved in dichloromethane (20 mL) and treated with pyridine (1.44 g, 18 mmol). The reaction was then cooled to ice bath temperature and treated with 2,4,6-triisopropylbenzenesulfoyl chloride (2.83 g, 9.3 mmol). The reaction was allowed to slowly come to room temperature and stirred for 3 days. A solution of 1 M aqueous HCl was added and the reaction was extracted with dichloromethane twice. The combined organics were dried over MgSO$_4$ and the solvent was removed. The residue was purified using silica gel chromatography to afford 1.75 g (51%) of a white powder. The material was crystallized by dissolving in warm hexane and cooling to −4° C. overnight. The mass recovery was 75%: $^1$H NMR (CDCl$_3$, 400 MHz) δ 0.92-1.08 (m, 2H), 1.15 (dd, 1H, J$_1$=5.5, J$_2$=6.8), 1.17-1.22 (m, 18H), 1.27-1.36 (m, 2H), 1.40-1.57 (m, 5H), 1.64-1.76 (m, 2H), 1.78-1.90 (m, 1H), 3.82-3.89 (m, 2H), 3.97-4.10 (m, 3H), 7.13 (s, 2H); HPLC-MS calcd. for C$_{23}$H$_{38}$O$_4$S (M+H$^+$) 411.3, found 411.4.

Step B. Preparation of (S)-1-cyclopentyl-3-(5,6-dichloro-benzimidazol-1-yl)-propan-2-ol. Two large (2-5 mL) microwave reactor tubes were charged with (S)-2,4,6-Triisopropyl-benzenesulfonic acid 3-cyclopentyl-2-hydroxy-propyl ester (1.88 g, 4.6 mmol), 5,6-dichlorobenzimidazole (859 mg, 4.6 mmol), K$_2$CO$_3$ (1.27 g, 9.2 mmol) and DMF (4 mL). The tubes were then heated to 160° C. for 6 minutes. The reaction was partitioned between ethyl acetate and water. The aqueous layer was extracted a total of 2 times with ethyl acetate and the combined organics were dried over MgSO$_4$. The solvent was removed and the resulting oil was chromatographed over silica gel using a linear gradient of 0-100% ethyl acetate in hexane to afford 566 mg (40%) of the title compound as a solid: HPLC-MS calcd. for C$_{15}$H$_{18}$Cl$_2$N$_2$O (M+H$^+$) 313.1, found 313.2.

Step C. 1-(S)-cyclopentylmethyl-2-(5,6-dichloro-benzimidazol-1-yl)-ethyl 4-nitro-phenyl carbonate was prepared in 18% yield an analogous fashion to preparation 3. $^1$H NMR (CDCl$_3$, 400 MHz) δ 1.03-1.21 (m, 2H), 1.47-1.66 (m, 5H), 1.76-1.95 (m, 4H), 4.26 (dd, 1H, J$_1$=7.8, J$_2$=15.2), 4.34 (dd, 1H, J$_1$=3.7, J$_2$=15.2), 5.04-5.12 (m, 1H), 7.06-7.11 (m, 2H), 7.52 (s, 1H), 7.85 (s, 1H), 7.89 (s, 1H), 8.14-8.19 (m, 2H); HPLC-MS calcd. for C$_{22}$H$_{21}$Cl$_2$N$_3$ (M+H$^+$) 478.1, found 478.2.

Preparation 5. Cbz-O-tBu-aspartinal diethyl acetal was described in US2002/0042376 (D. S. Karanewsky et al).

Preparation 6. (3S)-benzyloxycarbonylamino-(2R)-ethoxy-5-oxo-tetrahydrofuran was described in US2002/0042376 (D. S. Karanewsky et al).

Example 1

(3 S)-(3-Cyclopentyl-(2S)-{[5-(3-fluoro-phenyl)-furan-2-carbonyl]-amino}-propionylamino)-4-oxo-butyric acid

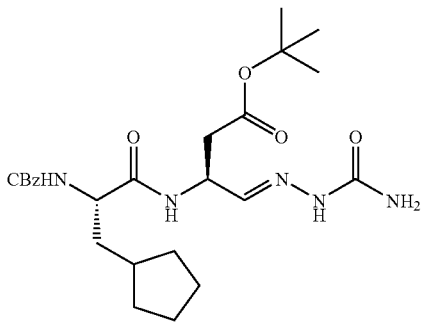

Step A. Synthesis of (3S)-[(2S)-Benzyloxycarbonylamino-3-cyclopentyl-propionylamino]-4-oxo-butyric acid t-butyl ester semicarbazone.

A flask was charged with (3S)-amino-4-oxobutanoic acid t-butyl ester semicarbazone, p-toluenesulfonate salt (170 mg, 0.42 mmol) and Cbz-cyclopentyl alanine dicyclohexylamine salt (170 mg, 0.42 mmol), HATU (177 mg, 0.47 mmol) and DCM (4 mL). Stirring was initiated and the reaction was treated with diisopropylethylamine (109 mg, 846 mmol). After stirring for 3 hours, the contents of the flask were transferred to a separatory funnel and treated with saturated aqueous sodium bicarbonate. The aqueous phase was extracted with DCM a total of 3 times and discarded. The combined organic phases were dried over MgSO$_4$ and the solvent was removed. The resulting oil was purified over silica gel using 0-7% MeOH in DCM to afford 187 mg (88%) of (3S)-[(2S)-benzyloxycarbonylamino-3-cyclopentyl-propionylamino]-4-oxo-butyric acid t-butyl ester semicarbazone as a foam: $^1$H NMR (CDCl$_3$, 400 MHz) δ 0.98-1.08 (m, 2H), 1.34 (s, 9H), 1.37-1.46 (m, 2H), 1.45-1.63 (m, 3H), 1.64-1.80 (m, 4H), 4.99 (dd, 1H, J$_1$=6.5, J$_2$=15.7), 2.59-2.68 (m, 1H), 4.77-4.85 (m, 1H), 4.97-5.07 (m, 2H), 5.45 (d, 1H, J=7.6), 7.04-7.10 (m, 1H), 7.21-7.30 (m, 5H), 7.43 (d, 1H, J=7.7), 9.22-9.26 (m, 1H); HPLC-MS calcd. for C$_{25}$H$_{37}$N$_5$O$_6$ (M+H$^+$) 504.3, found 504.4.

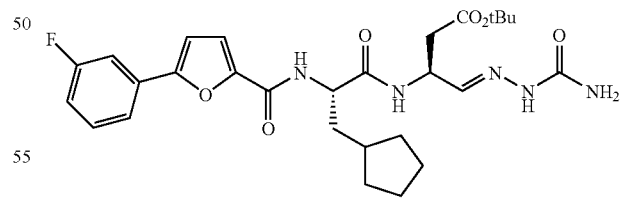

Step B. Synthesis of (3S)-(3-Cyclopentyl-(2S)-{[5-(3-fluoro-phenyl)-furan-2-carbonyl]-amino}-propionylamino)-4-oxo-butyric acid t-butyl ester semicarbazone.

A flask was charged with (3S)-[(2S)-Benzyloxycarbonylamino-3-cyclopentyl-propionylamino]-4-oxo-butyric acid t-butyl ester semicarbazone (168 mg, 0.33 mmol), 10% Pd/C (27 mg) and EtOH (3 mL). The atmosphere in the reaction was then exchanged for hydrogen by bubbling hydrogen gas through the solution with a needle for 5 minutes. The

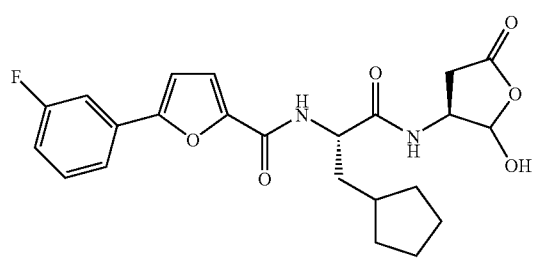

reaction was left under balloon pressure hydrogen for 1.5 h and then the atmosphere was exchanged back to nitrogen by a similar protocol as above. The reaction was filtered through Celite and the solvent was removed. After keeping the material on the high vacuum pump for 1 hour, the resulting material was treated with 5-(3-Fluoro-phenyl)-furan-2-carboxylic acid (83 mg, 0.40 mmol), HATU (165 mg, 0.43 mmol), DCM (5 mL) and diisopropylethylamine (129 mg, 1.0 mmol) in that order. The reaction was allowed to stir for 2 hours, poured into a separatory funnel and treated with saturated aqueous NaHCO$_3$ solution. The aqueous phase was extracted with DCM 3 times. The combined organics were dried over MgSO$_4$ and the solvent was removed. The resulting oil was purified over silica gel using a linear gradient of 0 to 10% MeOH in DCM to afford the desired product in nearly quantitative yield: HPLC-MS calcd. for C$_{28}$H$_{36}$FN$_5$O$_6$ (M+H$^+$) 558.3, found 558.4.

Step C. A portion of (3S)-(3-Cyclopentyl-(2S)-{[5-(3-fluoro-phenyl)-furan-2-carbonyl]-amino}-propionylamino)-4-oxo-butyric acid t-butyl ester semicarbazone (250 mg, 0.45 mmol) was dissolved in DCM (2 mL) and treated with anisole (0.5 mL) and trifluoroacetic acid (2 mL). The reaction was stirred for 2 hours and was completed according to HPLC-MS analysis. The solvent was removed and the residual TFA was removed azeotropically with toluene. The resulting oil was treated with dioxane (3 mL), acetic acid (1 mL) and 37% aqueous formaldehyde (1 mL). After 1 hour of stirring, the reaction was completed by HPLC-MS analysis. The solvent was removed and the residue was triturated with boiling ethyl acetate and filtered. This process was repeated once more and the resulting material was dissolved in 1 mL of 1:1 DMSO/MeOH and purified by reverse phase HPLC to afford 117 mg (58%) of title compound as a solid after lyophilization: $^1$H NMR (CD$_3$OD, 400 MHz) δ 1.14-1.38 (m, 2H), 1.48-1.70 (m, 4H), 1.79-1.97 (m, 5H), 2.46-2.56 (m, 1H), 2.62-2.72 (m, 1H), 4.25-4.34 (m, 1H), 4.56-4.63 (m, 2H), 3.65 (d, 1H, J=3.6), 7.07-7.13 (m, 1H), 7.23-7.26 (m, 1H), 7.42-7.48 (m, 1H), 7.67-7.72 (m, 2H); HPLC-MS calcd. for C$_{23}$H$_{25}$FN$_2$O$_6$ (M+H$^+$) 445.2, found 4.3.

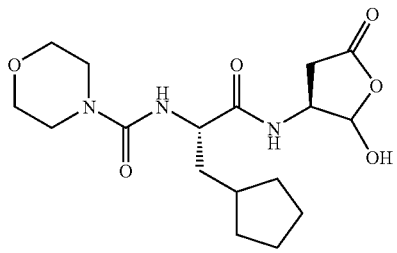

Example 2

(3S)-{3-Cyclopentyl-(2S)-[(morpholine-4-carbonyl)-amino]-propionylamino}-4-oxo-butyric acid

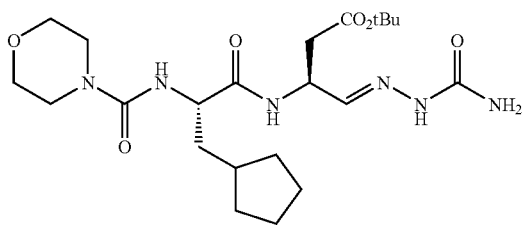

Step A. The synthesis of (3S)-{3-Cyclopentyl-(2S)-[(morpholine-4-carbonyl)-amino]-propionylamino}-4-oxo-butyric acid tert-butyl ester semicarbazone was performed in an analogous manner to example 1, step A and B except that 4-morpholine carbonyl chloride (1 eq.) was used as the electrophile to afford the desired material in 78% yield: $^1$H NMR (CDCl$_3$, 400 MHz) δ 1.04-1.18 (m, 2H), 1.42 (s, 9H), 1.44-1.62 (m, 5H), 1.73-1.88 (m, 4H), 2.60 (dd, 1H, J$_1$=7.0, J$_2$=15.7), 2.75 (dd, 1H, J$_1$=4.7, J$_2$=15.7), 3.30-3.34 (m, 4H), 3.62-3.72 (m, 4H), 4.27-4.36 (m, 1H), 4.79-4.87 (m, 1H), 5.28-5.33 (m, 1H) 7.24 (d, 1H, J=2.6), 7.70 (d, 1H, J=7.6), 9.27 (s, 1H); HPLC-MS calcd. for C$_{22}$H$_{38}$N$_6$O$_6$ (M+H$^+$) 483.3, found 483.4.

Step B. (3S)-{3-Cyclopentyl-(2S)-[(morpholine-4-carbonyl)-amino]-propionylamino}-4-oxo-butyric acid was prepared in an analogous manner to example 1, step C to afford the title compound in 41% yield: $^1$H NMR (CD$_3$OD, 400 MHz) δ 1.10-1.21 (m, 2H), 1.48-1.93 (m, 9H), 2.46-2.54 (m, 1H), 2.59-2.70 (m, 1H), 3.37-3.4 (m, 4H), 3.63-3.68 (m, 4H), 4.21-4.31 (m, 2H), 4.57-4.59 (m, 1H); HPLC-MS calcd. for C$_{17}$H$_{27}$N$_3$O$_6$ (M+$^+$) 370.2, found 370.4.

Example 3

(3S)-{3-cyclohexyl-(2S)-(morpholine-4-carbonyloxy)-propionylamino}-4-oxo-butyric acd

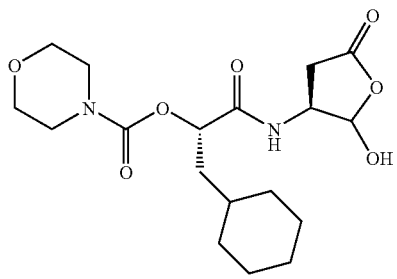

Step A. Preparation of (3S)-(3-Cyclohexyl-(2S)-hydroxypropionylamino)-4-oxo-butyric acid t-butyl ester semicarbazone.

A solution of (S)-2-hydroxy-3-cyclohexylpropionic acid (0.20 g, 1.2 mmol) in DMF (2 mL) was treated with HOBt (0.17 g, 1.3 mmol) and EDC (0.25 g, 1.3 mmol) and allowed to stir for 30 minutes. The reaction was then treated with (3S)-amino-4-oxobutanoic acid t-butyl ester semicarbazone, p-toluenesulfonate salt (515 mg, 1.3 mmol) and stirred for 16 hours. The reaction was then diluted with ethyl acetate and extracted twice with water. The organics were dried over MgSO₄ and the solvent was removed. The resulting oil was purified over silica gel using 0-10% MeOH in DCM to afford 53 mg (12%) of the title compound: ¹H NMR (400 MHz, CDCl₃) δ 0.76-0.96 (m, 2H), 1.01-1.25 (m, 3 H), 1.36 (s, 9H), 1.33-1.68 (m, 7H), 1.69-1.78 (m, 1H), 2.54 (dd, 1H, J₁=6.6, J₂=15.7), 2.62 (dd, 1H, J₁=5.4, J₂=15.7), 4.07-4.14 (m, 1H), 4.66-4.78 (m, 1H), 4.83-4.91 (m, 1H), 5.60-6.10 (m, 2H), 7.06 (d, 1H, J=2.7), 7.69 (d, 1H, J=8.9), 9.83 (s, 1H); HPLC-MS calcd. for C₁₈H₃₂N₄O₅ (M+H⁺) 385.2, found 385.4.

Step B. A solution of the resulting material from step A (48 mg, 0.13 nmnol) in DMF (1 mL) was treated with potassium tert-butoxide (17 mg, 0.15 mmol) and allowed to stir for 5 minutes. The resulting yellow solution was cooled in an ice/water bath and treated with 4-morpholine carbonyl chloride (21 mg, 0.14 mmol). After 3 hours, the reaction was quenched by addition of a solution of saturated aqueous NaHCO₃. The reaction was also treated with ethyl acetate and transferred to a separatory funnel. The aqueous layer was discarded and the organics were extracted twice with water, dried over MgSO₄ and the solvent was removed. The residue was purified over silica gel using 0-10% MeOH in DCM to afford 35 mg (56%) of (3S)-{3-cyclohexyl-(2S)-(morpholine-4-carbonyloxy)-propionylamino}-4-oxobutyric acid t-butyl ester semicarbazone: ¹H NMR (400 MHz, CDCl₃) δ 0.74-0.93 (m, 2H), 0.99-1.14 (m, 3 H), 1.22-1.32 (m, 1H), 1.31 (s, 9H), 1.48-1.69 (m, 7H), 2.44 (dd, 1H, J₁=6.3, J₂=15.8), 2.62 (dd, 1H, J₁=4.4, J₂=15.8), 3.29-3.41 (m, 3H), 3.43-3.62 (m, 5H), 4.78-4.85 (m, 1H), 5.02 (dd, 1H, J₁=4.6, J₂=8.8), 7.00 (d, 1H, J=2.7), 7.51 (d, 1H, J=8.8), 9.36 (s, 1H); HPLC-MS calcd. for C₂₃H₃₉N₅O₇ (M+H⁺) 498.3 found 498.4.

Step C. The title compound was obtained in an analogous manner to example 1, step C in 92% yield: ¹H NMR (CD₃OD, 400 MHz) δ 0.87-1.06 (m, 2H), 1.12-1.36 (m, 5H), 1.38-1.50 (m, 1H), 1.57-1.83 (m, 10H), 2.49-2.57 (m, 1H), 2.59-2.68 (m, 1H), 3.34-3.54 (m, 4H), 3.57-3.74 (m, 7H), 4.22-4.30 (m, 1H), 4.58 (dd, 1H, J₁=4.1, J₂=8.2), 4.94-5.03 (m, 1H); HPLC-MS calcd. for C₁₈H₂₈N₂O₇ (M+H⁺) 385.2, found 385.5.

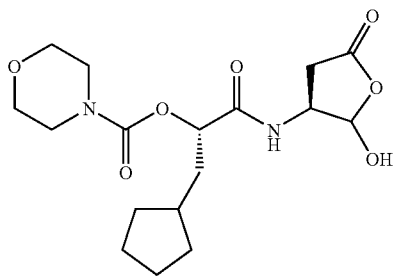

Example 4

(3S)-[(2R)-Cyclopentylmethyl-4-morpholin-4-yl-4-oxo-butyrylamino]-4-oxo-butyric acid

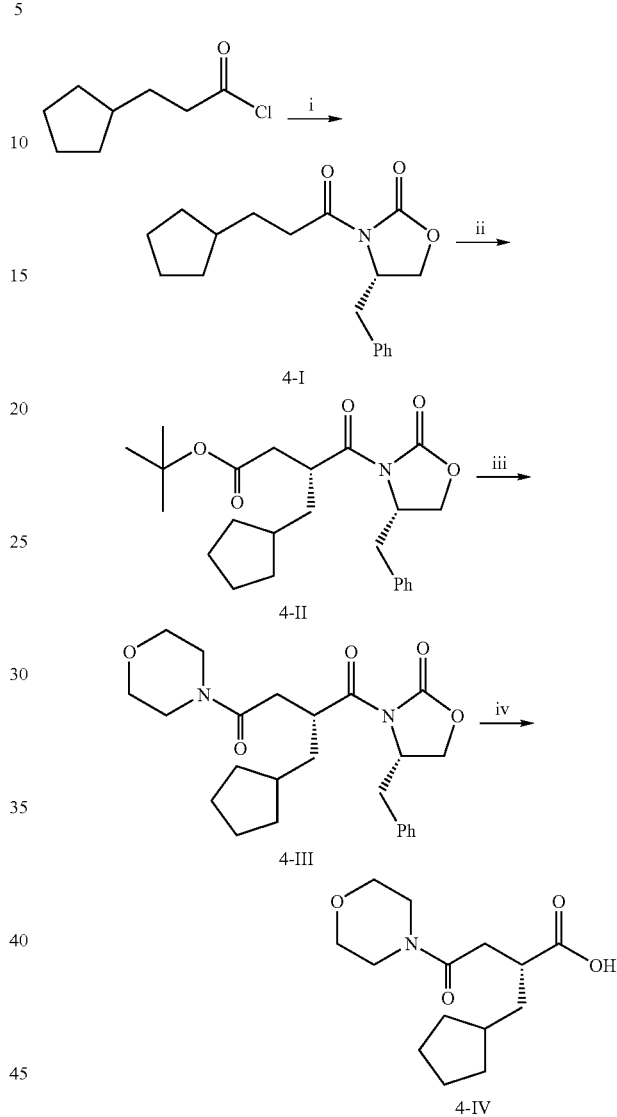

The literature protocols used in this example referred to a) Evans, D. A.; Britton, T. C.; Dorow, R. L.; Dellaria, J. F. *Tetrahedron* 1988, 44(17), 5525; b) Evans, D. A.; Wu, L. D.; Wiener, J. J. M.; Johnson, J. S.; Ripin, D. H. B.; Tedrow, J. S. *J. Org. Chem.* 1999, 64, 6411.

Step A. The acyl oxazolidinone 4-I was prepared according to literature protocol in 66% yield: ¹H NMR (CDCl₃, 400 MHz) δ 1.01-1.15 (m, 2H), 1.41-1.80 (m, 9H), 2.69 (dd, 1H, J₁=9.6, J₂=13.3), 2.77-2.98 (m, 2H), 3.23 (dd, 1H, J₁=3.3, J₂=13.3), 4.06-4.16 (m, 2H), 4.56-4.63 (m, 1H), 7.13-7.29 (m, 5H); HPLC-MS calcd. for C₁₈H₂₃NO₃ (M+H⁺) 302.2, found 302.4.

Step B. The succinic acid t-butyl ester 4-II was prepared as per literature protocol in 63% yield: ¹H NMR (CDCl₃, 400 MHz) δ 0.96-1.08 (m, 1H), 1.09-1.12 (m, 1H), 1.36 (s, 9H), 1.37-1.79 (m, 9H), 2.45 (dd, 1H, J₁=4.5, J₂=16.7), 2.63-2.75 (m, 2H), 3.28 (dd, 1H, J₁=3.2, J₂=13.5), 4.04-4.10 (m, 2H), 4.09-4.18 (m, 1H), 4.54-4.62 (m, 1H), 7.17-7.30 (m, 5H); HPLC-MS calcd. for C₂₄H₃₃NO₅ (M+Na⁺) 438.2, found 438.4.

Step C. A solution of 4-II (400 mg, 0.96 mmol) was treated with a cleavage cocktail of TFA:DCM:H$_2$O (50:45:5 v/v, 2 mL) and stirred overnight. The solvent was then removed and the reaction was co-evaporated with toluene. The residue was treated with HATU (383 mg, 1.0 mmol), DCM (3 mL) and excess morpholine. After stirring for 2 hours, the reaction mixture was diluted with ethyl acetate and extracted with saturated aqueous sodium bicarbonate solution once and water twice. The organics were dried over MgSO$_4$ and the solvent was removed. The residue was purified by silica gel chromatography using a linear gradient of 0 to 100% ethyl acetate in hexane to afford 398 mg (97%) of 4-III: HPLC-MS calcd. for C$_{24}$H$_{32}$N$_2$O$_5$ (M+H$^+$) 429.2, found 429.4.

Step D. A solution of 4-III (396 mg, 0.93 mmol) in THF (14 mL) was cooled in an ice/water bath and treated with a solution of 31% aqueous hydrogen peroxide (408 μL, 3.4 mmol) followed by a solution of LiOH (45 mg, 1.9 mmol) in water (4.6 mL). After 2 hours, HPLC-MS analysis indicated that the hydrolysis was completed and the reaction mixture was treated with saturated aqueous Na$_2$SO$_3$ solution (3 mL) and saturated aqueous NaHCO$_3$ solution (3 mL) and allowed to stir overnight. Most of the solvent was removed by rotary evaporation and the residue was diluted with water. The reaction was extracted with dichloromethane twice and the organic extracts were discarded. The aqueous phase was acidified with concentrated HCl and extracted with dichloromethane twice. The combined organics were dried over MgSO$_4$ and the solvent was removed. The resulting oil 4-IV was used without further purification: HPLC-MS calcd. for C$_{14}$H$_{23}$NO$_4$ (M+H$^+$) 270.2, found 270.4.

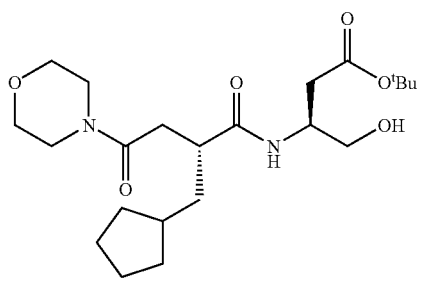

Step E. (3S)-[(2R)-Cyclopentylmethyl-4-morpholin-4-yl-4-oxo-butyrylamino]-4-hydroxy-butyric acid tert-butyl ester.

A solution of Cbz-aspartinol t-butyl ester (0.345 g, 1.1 mmol) in methanol (3 mL) was hydrogenated over 10% Pd/C (15 mg) overnight. The catalyst was removed by filtration through Celite and the solvent was removed. The resulting oil was combined with the abovementioned 4-IV, dissolved in dichloromethane (5 mL) and treated with HATU (0.42 g, 1.1 mmol) and diisopropylethylamine (240 mg, 1.9 mmol). After 30 minutes of stirring, the reaction was treated with a saturated solution of NaHCO$_3$ in water and the aqueous phase was. extracted with dichloromethane three times. The organics were dried over MgSO$_4$ and the solvent was removed. The resulting oil was purified over silica gel using ethyl acetate as solvent to afford 425 mg (>100%, there was solvent trapped in the product) of the desired product: $^1$H NMR (CDCl$_3$, 400 MHz) δ 0.94-1.07 (m, 2H), 1.24-1.58 (m, 5H), 1.37 (s, 9H), 1.61-1.78 (m, 3H), 2.25-2.35 (m, 1H), 2.45 (dd, 1H, J$_1$=6.0, J$_2$=16.1), 2.58 (dd, 1H, J$_1$6.9, J$_2$=16.1), 2.59-2.70 (m, 2H), 3.13 (dd, 1H, J$_1$=7.4, J$_2$=14.9), 3.32-3.73 (m, 10H), 3.96-4.04 (m, 1H), 6.65 (d, 1H, J=7.7); HPLC-MS calcd. for C$_{22}$H$_{38}$N$_2$O$_6$ (M+H$^+$) 427.3, found 427.5.

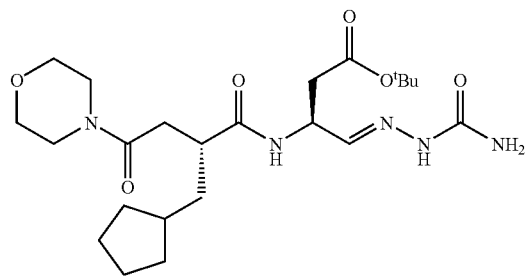

Step F. A solution of the product of Step E (409 mg, 0.96 mmol) in dichloromethane (5 mL) was treated with Dess-Martin periodinane (488 mg, 1.15 mmol) and stirred for 2 hours. The reaction was then treated with 1 M Na$_2$S$_2$O$_3$ (10 mL) and saturated aqueous NaHCO$_3$ (10 mL). The aqueous phase was extracted 3 times with dichloromethane, dried over MgSO$_4$ and the solvent was removed. The oil was dissolved in a mixture of EtOH and water (2:1) (3.5 mL) and cooled in an ice/water bath. The reaction was then treated with sodium acetate trihydrate (143 mg, 1.1 mmol) and semicarbazide hydrochloride (118 mg, 1.1 mmol) in that order and stirred overnight allowing the reaction to slowly come to room temperature. The reaction was then diluted with ethyl acetate and extracted with water three times. The organics were dried over MgSO$_4$ and the solvent was removed and the resulting oil was used without further purification or thorough drying): HPLC-MS calcd. for C$_{23}$H$_{39}$N$_5$O$_6$ (M+H$^+$) 482.3, found 482.6.

Step G. The product from step F was dissolved in dichloromethane (2 mL) and treated with anhydrous anisole (0.5 mL) and TFA (2 mL). The reaction was stirred for 2 hours and the solvent was removed. The residue was co-evaporated with toluene twice. The resulting oil was treated with dioxane (3 mL), acetic acid (1 mL) and 37% aqueous formaldehyde (1 mL) in that order and stirred for 2 hours. The reaction was diluted with ethyl acetate, extracted with water twice, dried over MgSO$_4$ and the solvent was removed. The residue was purified on a mass-triggered preparative HPLC system to afford 33 mg (9% over 4 steps) of the title compound as a lyophilized solid. The mass signal of this material is extremely weak and may have been responsible for the low recovery: $^1$H NMR (CD$_3$OD, 400 MHz) δ 1.03-1.17 (m, 2H), 1.32-1.40 (m, 1H), 1.48-1.96 (m, 8H), 2.32-2.53 (m, 2H), 2.60-2.83 (m, 3H), 3.28-3.32 (m; 1H), 3.47-3.69 (m, 8H), 4.20-4.30 (m, 1H), 4.57-4.60 (m, 1H); HPLC-MS calcd. for C$_{18}$H$_{28}$N$_2$O$_6$ (M+H$^+$) 369.4, found 369.5.

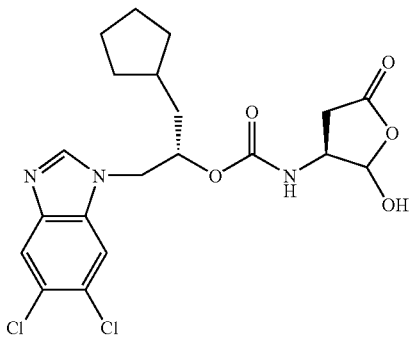

Example 5

(3S)-[(1S)-Cyclopentylmethyl-2-(5,6-dichloro-benzoimidazol-1-yl)-ethoxycarbonylamino]-4-oxo-butyric acid

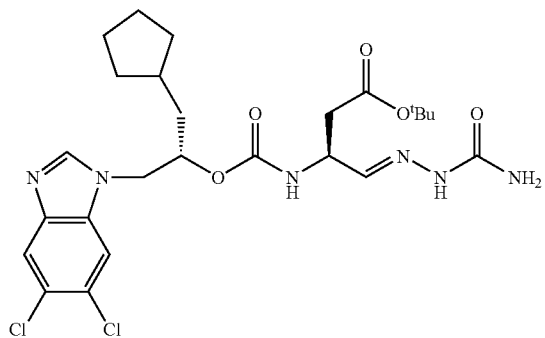

Step A. A solution of 1-(S)-cyclopentylmethyl-2-(5,6-dichloro-benzoimidazol-1-yl)-ethyl 4-nitrophenyl carbonate (169 mg, 0.35 mmol) and (3S)-amino-4-oxobutanoic acid t-butyl ester semicarbazone, p-toluenesulfonate salt (142 mg, 0.35 mmol) in DMF (3 mL) was treated with diisopropylethylamine (112 mg, 0.86 mmol) and allowed to stir for 18 hours. The reaction was diluted with 1 M aqueous NaOH and extracted with ethyl acetate 3 times. The combined organics were extracted with 1 M NaOH until the aqueous extracts were no longer yellow. The organics were then dried over MgSO$_4$ and the solvent was removed. The residual oil was purified over silica gel using a gradient of 0 to 10% MeOH in dichloromethane to afford 91 mg (45%) of the product as a white crystalline solid: $^1$H NMR (CDCl$_3$, 400 MHz) δ 1.00-1.12 (m, 2H), 1.35 (s, 9H), 1.48-1.84 (m, 11H), 2.50 (dd, 1H, J$_1$=6.5, J$_2$=15.6), 2.59 (dd, 1H, J$_1$=5.5, J$_2$=15.7), 4.16 (dd, 1H, J$_1$=6.6, J$_1$=15.0), 4.29 (dd, 1H, J$_1$=3.7, J$_2$=15.0), 4.50-4.60 (m, 1H), 5.03-5.11 (m, 1H), 6.60 (d, 1H, J=8.9), 7.14 (d, 1H, J=1.4), 7.46 (s, 1H), 7.74 (s, 1H), 7.85 (s, 1H), 9.91 (s, 1H); HPLC-MS calcd. for C$_{25}$H$_{34}$C$_{12}$N$_6$O$_5$ (M+H$^+$) 569.2, found 569.3.

Step B. The t-butyl ester semicarbazone obtained from last step was converted to the title compound in an analogous manner to example 1, step C in 24% yield: HPLC-MS calcd. for C$_{20}$H$_{23}$C$_{12}$N$_3$O$_5$ (M$^+$) 455.1, found 455.5.

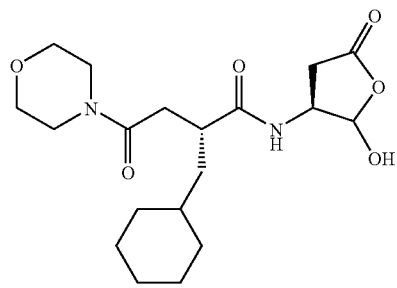

Example 6

(3S)-{(2R)-Cyclohexylmethyl-4-morpholin-4-yl-4-oxo-butyrylamino}-4-oxo-butyric acid

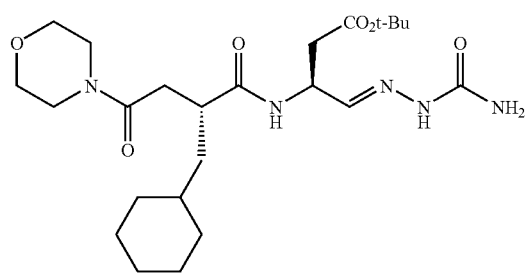

Step A. The synthesis of (3S)-{(2R)-Cyclohexylmethyl-4-morpholin-4-yl-4-oxo-butyrylamino}-4-oxo-butyric acid t-butyl ester semicarbazone was performed in an analogous manner to example 1, step 1 except that (2R)-Cyclohexylmethyl-4-morpholin-4-yl-4-oxo-butyric acid was used as the carboxylic acid to afford the title material in 9.1% yield: HPLC-MS calcd. for C$_{24}$H$_{41}$N$_5$O$_6$ (M+H$^+$) 496.3, found 496.4.

Step B. This transformation was performed in an analogous manner to example 1, step C except that after the removal of the formaldehyde solution, the material was crashed out of cold ether. The solid was then dissolved in ethyl acetate and extracted with water twice. The organics were dried over MgSO$_4$ and the solvent was removed to afford the title compound in 56% yield: HPLC-MS calcd. for C$_{19}$H$_{30}$N$_2$O$_6$ (M+H$^+$) 383.2, found 383.4.

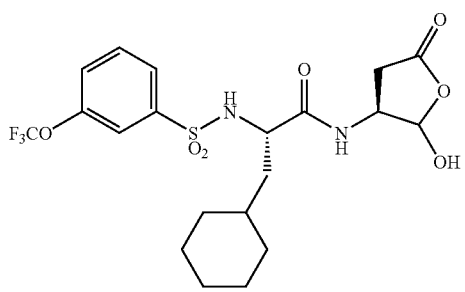

Example 7

(3S)-[3-Cyclohexyl-(2S)-(3-trifluoromethoxy-benzenesulfonylamino)-propionylamino]-4-oxo-butyric acd

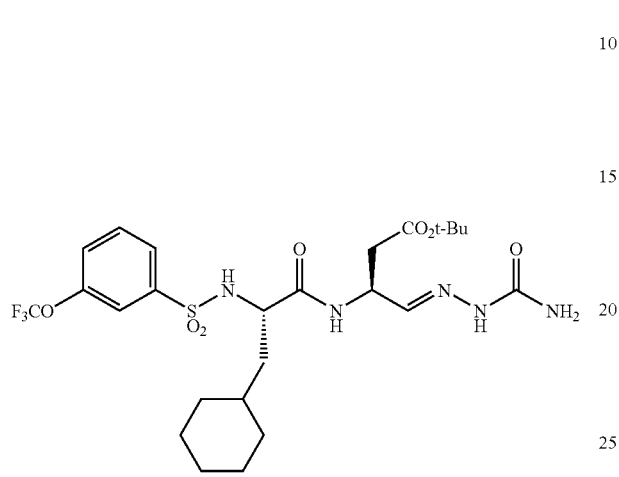

Step A. (3S)-[3-Cyclohexyl-(2S)-(3-trifluoromethoxy-benzenesulfonylamino)-propionylamino]-4-oxo-butyric acid t-butyl ester semicarbazone was prepared in 48% yield in an analogous manner to example 1 except that 3-Cyclohexyl-2-(S)-(3-trifluoromethoxy-benzenesulfonylamino)-propionic acid was used as the carboxylic acid: HPLC-MS calcd. for $C_{25}H_{36}F_3N_5O_7S$ (M+H$^+$) 608.2, found 608.4.

Step B. This transformation was performed in an analogous manner to example 1, step C to afford the title material in 16% yield: HPLC-MS calcd. for $C_{20}H_{25}F_3N_2O_7S$ (M+H$^+$) 495.1, found 495.3.

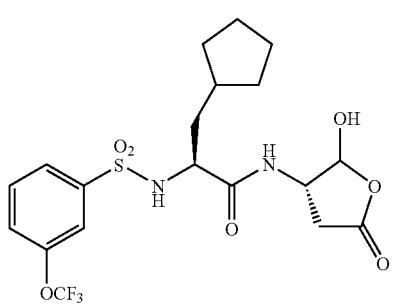

Example 8

(3 S)-[3-Cyclopentyl-(2S)-(3-trifluoromethoxy-benzenesulfonylamino)-propionylamino]-4-oxo-butyric acid

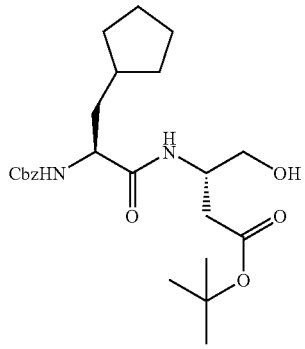

Step A. (3S)-[(2S)-Benzyloxycarbonylamino-3-cyclopentyl-propionylamino]-4-hydroxy-butyric acid tert-butyl ester was prepared in an analogous manner to example 4, step E except that cbz-cyclopentylalanine dicyclohexylamine salt was used as the acid to afford the desired product in 79% yield: $^1$H NMR (CDCl$_3$, 400 MHz) δ 1.05-1.20 (m, 2H), 1.44 (s, 9H), 1.41-1.70 (m, 5H), 1.71-1.88 (m, 4H), 2.47-2.58 (m, 2H), 2.81-2.88 (m, 1H), 3.62-3.73 (m, 2H), 4.06-4.23 (m, 2H), 5.11 (s, 2H), 5.23 (d, 11H, J=7.0), 6.81 (d, 1H, J=7.8), 7.29-7.38 (m, 5H); HPLC-MS calcd. for $C_{24}H_{36}N_2O_6$ (M+H$^+$) 449.3, found 449.5.

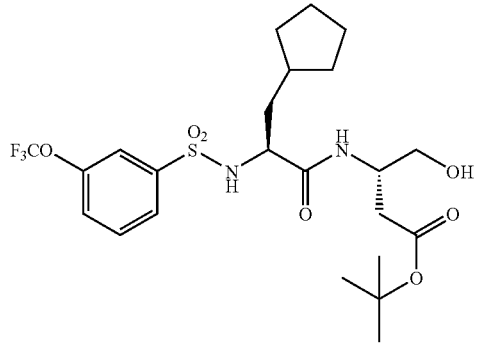

Step B. A sample of (3S)-[(2S)-benzyloxycarbonylamino-3-cyclopentyl-propionylamino]-4-hydroxy-butyric acid tert-butyl ester (205 mg, 0.46 mmol) was treated with 10% Degussa type Pd/C (27 mg) and ethanol (5 mL). The material was then hydrogenated and worked up as described in example 1, step B to afford the intermediate amine which was used without further purification: HPLC-MS calcd. for $C_{16}H_{30}N_2O_4$ (M+H$^+$) 315.2, found 315.5.

This material was then dissolved in dichloromethane (5 mL) and cooled with an ice/water bath. The mixture was treated with 3-trifluoromethoxybenzenesulfonyl chloride (125 mg, 0.48 mmol) and diisopropylethylamine and allowed to stir and warm to room temperature overnight. The reaction was then diluted with dichloromethane, extracted with water once, dried over Na$_2$SO$_4$, filtered and the solvent was removed. The resulting oil was purified over silica gel using a linear gradient of 0-80% ethyl acetate in hexane to afford 214 mg (87%) of (3S)-[3-Cyclopentyl-(2S)-(3-trifluoromethoxy-benzenesulfonylamino)-propionylamino]4-hydroxy-butyric acid tert-butyl ester: $^1$H NMR (CDCl$_3$, 400 MHz) δ 0.81-1.03 (m, 2H), 1.16-1.24 (m, 1H), 1.25-1.54 (m, 4H), 1.44 (s, 9H), 1.55-1.70 (m, 4H), 1.71-1.88 (m, 4H), 2.47 (d, 2H, J=6.4), 3.13 (dd, 1H, J$_1$=6.2, J$_2$=6.3), 3.57-3.67 (m, 3H), 4.15-4.23 (m, 1H), 6.11 (d, 1H, J=7.0), 7.14 (d, 1H, J=8.4), 7.44 (d, 1H, J=8.3), 7.57 (dd, 1H, J$_1$=8.0, J$_2$=8.1), 7.74 (s, 1H), 7.84 (d, 1H, J=7.9); HPLC-MS calcd. for C$_{23}$H$_{33}$F$_3$N$_2$O$_7$S (M+H$^+$) 539.2, found (M−C$_4$H$_{10}$+H$^+$) 465.4; (M−C$_4$H$_8$+H$^+$) 483.4.

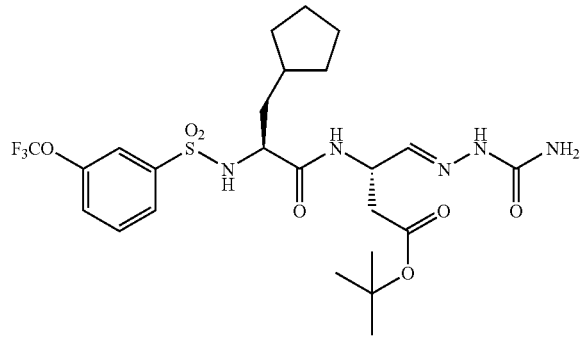

Step C: (3S)-[3-Cyclopentyl-(2S)-(3-trifluoromethoxy-benzenesulfonylamino)-propionylamino]-4-oxo-butyric acid tert-butyl ester semicarbazone was prepared in 86% yield in an analogous manner to example 4, step F except that the material was purified on silica gel using 0-10% methanol in dichloromethane: $^1$H NMR (CDCl$_3$, 400 MHz) δ 0.80-1.07 (m, 3H), 1.18-29 (m, 1H), 1.32-1.40 (m, 3H), 1.44 (s, 9H), 1.55-1.67 (m, 4H), 2.66-2.80 (m, 2H), 3.62-3.70 (m, 1H), 4.85-4.92 (m, 1H), 5.27 (m, 1H), 6.44 (m, 1H), 7.12 (d, 1H, J=1.6), 7.37-7.45 (m, 2H), 7.58 (dd, 1H, J$_1$=8.0, J$_2$=8.1), 7.72-7.76 (m, 1H), J=8.0), 7.86 (d, 1H, J=8.0), 9.03 (s, 1H); HPLC-MS calcd. for C$_{24}$H$_{34}$F$_3$N$_5$O$_7$S (M+H$^+$) 594.2, found 594.5.

Step D: (3S)-[3-Cyclopentyl-(2S)-(3-trifluoromethoxy-benzenesulfonylamino)-propionylamino]-4-oxo-butyric acid was synthesized in 41% yield in an analogous manner to example 4, step G: $^1$H NMR (CD$_3$OD, 400 MHz) δ 0.90-1.00 (m, 2H), 1.30-1.60 (m, 7H), 1.62-1.76 (m, 2H), 2.26-2.75 (m, 1H), 2.47-2.59 (m, 1H), 3.64-3.73 (m, 1H), 4.08-4.16 (m, 1H), 4.51 (d, 0.5H, J=3.9), 4.54 (d, 0.5H, J=4.2), 7.51-7.56 (m, 1H), 7.66 (dd, 1H, J$_1$=J$_2$=8.0), 7.74-7.76 (m, 1H), 7.81-7.85 (m, 1H); HPLC-MS calcd. for C$_{19}$H$_{23}$F$_3$N$_2$O$_7$S (M+H$^+$) 481.1, found 481.4.

Example 9

(3S)-[3,3-Dimethyl-(1S)-(morpholine-4-carbonyl)-butoxycarbonylamino]-4-oxo-butyric acid

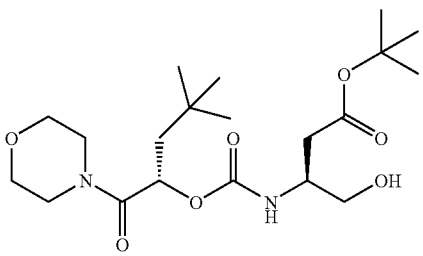

Step A. (3S)-[3,3-Dimethyl-(1S)-(morpholine-4-carbonyl)-butoxycarbonylamino]-4-hydroxy-butyric acid tert-butyl ester was prepared in an analogous manner to example 5, step A except that (S)-3,3-dimethyl-1-(morpholine-4-carbonyl)-butyl 4-nitrophenyl carbonate was used, which was used without further purification: HPLC-MS calcd. for C$_{20}$H$_{36}$N$_2$O$_7$ (M+H$^+$) 417.3, found 417.5.

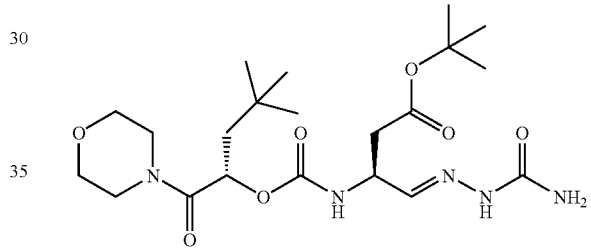

Step B. (3S)-[3,3-Dimethyl-(1S)-(morpholine-4-carbonyl)-butoxycarbonylamino]-4-oxo-butyric acid tert-butyl ester semicarbazone was synthesized in 68% yield over 2 steps, in an analogous manner to example 4, step F except that the material was purified on silica gel using 0-10% methanol in dichloromethane (data are for the major geometrical isomer): $^1$H NMR (CDCl$_3$, 400 MHz) δ 0.95 (s, 9H), 1.40 (s, 9H), 1.40-1.47 (m, 1H), 1.79 (dd, 1H, J$_1$=9.9, J$_2$=14.9), 4.57-4.64 (m, 1H), 5.32-5.37 (m, 1H), 6.55 (d, 1H, J=8.8), 7.16 (d, 1H, J=2.7), 9.71 (s, 1H); HPLC-MS calcd. for C$_{21}$H$_{37}$N$_5$O$_7$ (M+H$^+$) 472.3, found 472.2.

Step C. The title compound was obtained in 41% yield in an analogous manner to example 4, step G: HPLC-MS calcd. for C$_{16}$H$_{26}$N$_2$O$_7$ (M+H$^+$) 359.2, found 359.4.

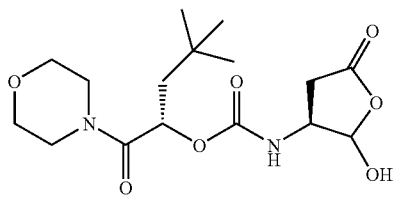

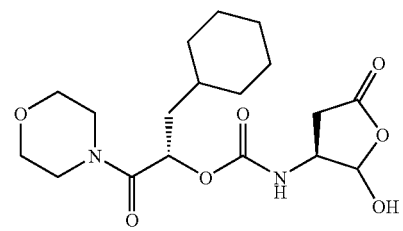

Example 10

(3S)-[2-cyclohexyl-(1S)-(morpholin-4-carbonyl)-ethoxycarbonylamino]-4-oxo-butyric acid

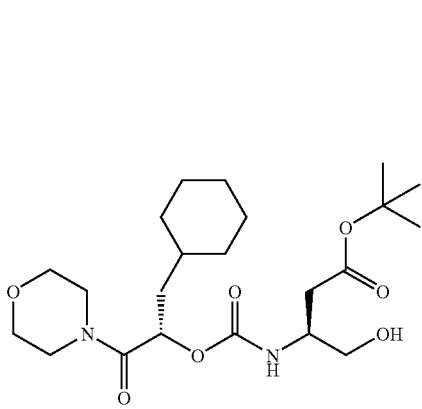

Step A. (3S)-[2-Cyclohexyl-(1S)-(morpholin-4-carbonyl)-ethoxycarbonylamino]-4-hydroxy-butyric acid tert-butyl ester was prepared in an analogous manner to example 5, step A except that 2-cyclohexyl-(1S)-(morpholin-4-carbonyl)-ethyl 4-nitrophenyl carbonate was used to afford 61% of the desired product which was purified by silica gel chromatography using 0-100% ethyl acetate in hexane): $^1$H NMR (CDCl$_3$, 400 MHz) δ 0.81-1.03 (m, 2H), 1.08-1.32 (m, 4H), 1.45 (s, 9H), 1.62-1.86 (m, 7H), 2.49-2.62 (m, 2H), 3.38-3.78 (m, 9H), 3.93-4.02 (m, 1H), 5.29 (d, 1H, J=8.3), 5.63 (d, 1H, J=6.7); HPLC-MS calcd. for $C_{22}H_{38}N_2O_7$ (M+H$^+$) 443.3, found 443.5.

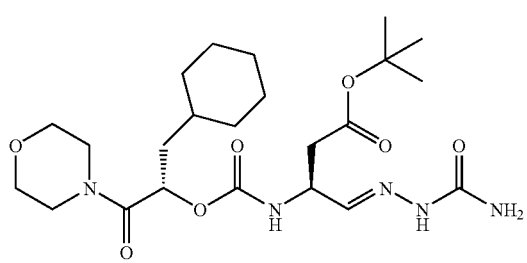

Step B. (3 S)-[2-cyclohexyl-(1S)-(morpholin-4-carbonyl)-ethoxycarbonylamino]-4-oxo-butyric acid tert-butyl ester semicarbazone was synthesized in 89% yield over 2 steps in an analogous manner to example 4, step F except that the material was purified on silica gel using 0-10% methanol in dichloromethane (data are for the major geometrical isomer): $^1$H NMR (CDCl$_3$, 400 MHz) δ 0.78-0.99 (m, 2H), 1.05-1.27 (m, 3H), 1.39 (s, 9H), 1.36-1.47 (m, 2H), 1.58-1.82 (m, 6H), 2.58 (dd, 1H, J$_1$=7.1, J$_2$=16.0), 2.72 (dd, 1H, 3.39-3.77 (m, 9H), 4.55-4.63 (m, 1H), 5.26-5.62 (m, 1H), 6.53 (d, 1H, J=8.7), 7.18 (d, 1H, J=2.7), 9.76 (s, 1H); HPLC-MS calcd. for $C_{22}H_{39}N_5O_7$ (M+H$^+$) 498.3, found 498.5.

Step C. The title compound was prepared in 41% yield in an analogous manner to example 4, step G: HPLC-MS calcd. for $C_{18}H_{28}N_2O_7$ (M+H$^+$) 385.2, found 385.4.

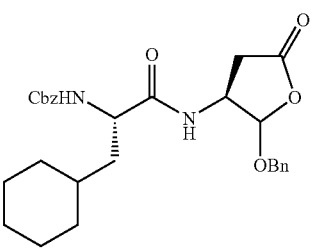

Example 11

(3S)-[(2S)-benzyloxycarbonylamino-3-cycohexyl-propionylamino]-2-benzyloxy-5-oxo-tetrahydrofuran Step A. Preparation of (3S)-[(2S)-Benzyloxycarbonylamino-3-cyclohexyl-propionylamino]-4,4-diethoxy-butyric acid tert-butyl ester.

A mixture of Cbz-O-tBu-aspartinal diethyl acetal (320 mg, 0.84 mmol) and 10% Pd/C (30 mg) was treated with ethyl acetate (10 mL). The atmosphere in the reaction was then exchanged for hydrogen by bubbling hydrogen gas through the solution with a needle for 5 minutes. The reaction was left under balloon pressure hydrogen for 3 h and then the atmosphere was exchanged back to nitrogen by a similar protocol as above. The reaction was filtered through celite and the solvent was removed. The material was coevaporated with dichloromethane 3 times and combined with cbz-cyclohexylalanine dicyclohexylamine salt (448 mg, 92 mmol) and HATU (458 mg, 1.2 mmol). The mixture was treated with dichloromethane (5 mL) and diisopropylethylamine (220 mg, 1.7 mmol) and stirred for 3 hours. The reaction was charged to a separatory funnel, treated with saturated aqueous NaHCO$_3$ and the aqueous phase was extracted with dichloromethane 3 times and discarded. The organics were dried over MgSO$_4$ and the solvent was removed. The residue was purified by silica gel chromatography using a linear gradient of 0 to 60% ethyl acetate in hexane to afford 372 mg (83%) of the desired material: $^1$H NMR (CDCl$_3$, 400 MHz) δ 0.76-0.94 (m, 2H), 1.00-1.20 (m, 9H), 1.23-1.35 (m, 1H), 1.36 (s, 9H), 1.35-1.43 (m, 1H), 1.54-1.65 (m, 5H), 1.66-1.74 (m, 1H), 2.45-2.50 (m, 2H), 3.37-3.51 (m, 2H), 3.57-3.66 (m, 2H), 4.07-4.17 (m, 1H), 4.28-4.38 (m, 1H), 4.40-4.43 (m, 1H), 5.03

(dd, 2H, J₁=12.3, J₂=20.4), 5.10 (d, 1H, J=8.1), 6.39 (d, 1H, J=8.8), 7.21-7.31 (m, 5H); HPLC-MS calcd. for $C_{29}H_{46}N_2O_7$ (M+H⁺) 557.3, found 557.5.

Step B. A sample of the product from step A (47 mg, 88 μmol) was treated with benzyl alcohol (0.5 mL) and TFA (0.5 mL) and stirred for 30 minutes. The reaction was quenched by pouring it into a solution of saturated aqueous NaHCO₃ and the aqueous layer was extracted with dichloromethane 3 times. The organics were dried over MgSO₄ and the solvent was removed. The residue was purified by silica gel chromatography using a linear gradient of 0 to 60% ethyl acetate in hexane to afford 28 mg (64%) of the title compound: HPLC-MS calcd. for $C_{28}H_{34}N_2O_6$ (M+H⁺) 495.2, found 495.5.

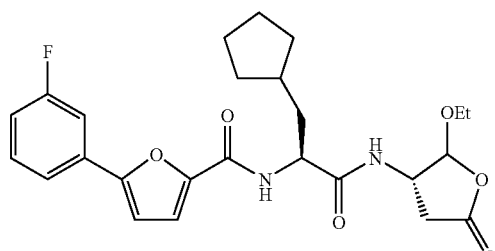

Example 12

(3S)-[3-Cyclopentyl-(2S)-{[5-(3-fluoro-phenyl)-furan-2-carbonyl]-amino}propionylamino]-2-ethoxy-5-oxo-tetrahydrofuran

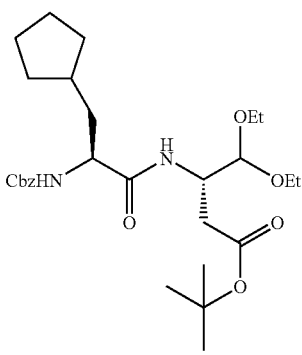

Step A. (3S)-[(2S)-Benzyloxycarbonylamino-3-cyclopentyl-propionylamino]-4,4-diethoxy-butyric acid tert-butyl ester was prepared in 47% yield in an analogous manner to example 11, step A except that Cbz-cyclopentylalanine dicyclohexylamine salt was used as the acid: HPLC-MS calcd. for $C_{28}H_{44}N_2O_7$ (M+Na⁺) 543.3, found 543.5.

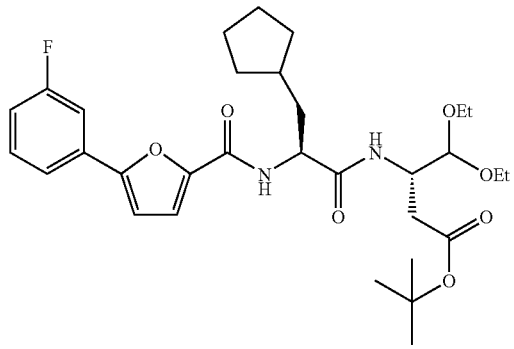

Step B. A sample of (3S)-[3-Cyclopentyl-(2S)-{[5-(3-fluoro-phenyl)-furan-2-carbonyl]-amino}-propionylamino]-4,4-diethoxy-butyric acid tert-butyl ester was prepared in 46% yield in an analogous manner to example 1, step B: HPLC-MS calcd. for $C_{31}H_{43}FN_2O_7$ (M+H⁺) 575.3, found 575.4.

Step C. A sample of (3S)-[3-Cyclopentyl-(2S)-{[5-(3-fluoro-phenyl)-furan-2-carbonyl]-amino}-propionylamino]-4,4-diethoxy-butyric acid tert-butyl ester (50 mg, 91 μmol) was treated with 4 M HCl in dioxane and stirred for 1 hour. The solvent was then removed and the residue was purified using mass-triggered preparative HPLC to afford 15 mg (34%) of the desired material as anomeric mixture: HPLC-MS calcd. for $C_{25}H_{29}FN_2O_6$ (M+H⁺) 473.2, found 473.3.

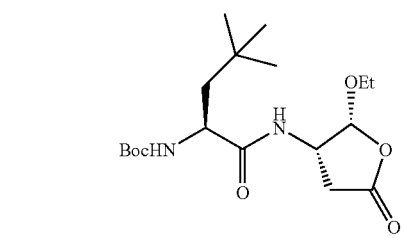

Example 13

(3S)-[(2S)-t-butoxycarbonylamino-4,4-dimethyl-pentanoylamino]-(2R)-ethoxy-5-oxo-tetrahydrofuran The title compound was obtained in 23% yield in an analogous manner to example 11, step A except that t-Boc-cyclopentylalanine and the known (3S)-benzyloxycarbonylamino-(2R)-ethoxy-5-oxo-tetrahydrofuran were used: ¹H NMR (CDCl₃, 400 MHz) δ 0.96 (s, 9H), 1.25 (t, 3H, J=7.1), 1.36 (dd, 1H, J₁=8.6, J₂=14.6), 1.44 (s, 9H), 1.92 (dd, 1H, J₁=3.8, J₂=14.5), 2.41 (dd, 1H, J₁=10.3, J₂=17.3), 2.84 (dd, 1H, J₁=8.6, J₂=17.3), 3.64 (dq, 1H, J₁=7.1, J₂=9.6), 3.91 (dq, 1H, J₁=7.1, J₂=9.6), 4.08-4.96 (m, 1H), 4.66-4.78 (m, 2H), 5.44 (d, 1H, J=5.3), 6.81 (d, 1H, J=7.4); HPLC-MS calcd. for $C_{18}H_{32}N_2O_6$ (M+H⁺) 373.2, found 373.4.

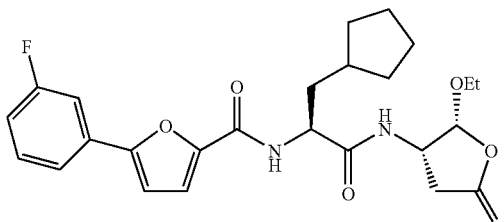

Example 14

(3S)-[3-Cyclopentyl-(2S)-{[5-(3-fluoro-phenyl)-furan-2-carbonyl]-amino}propionylamino]-(2R)-ethoxy-5-oxo-tetrahydrofuran

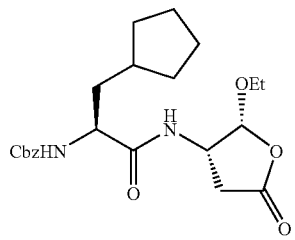

Step A. (3S)-[(2S)-benzyloxycarbonylamino-3-cycopentyl-propionylamino]-(2R)-ethoxy-5-oxo-tetrahydrofuran was obtained in 28% yield in an analogous manner to example 11, step A except that cbz-cyclopentylalanine dicyclohexylamine salt and the known (3S)-benzyloxycarbonylamino-(2R)-ethoxy-5-oxo-tetrahydrofuran were used: $^1$H NMR (CDCl$_3$, 400 MHz) δ 1.07-1.18 (m, 2H), 1.24 (t, 3H, J=7.0), 1.47-1.57 (m, 2H), 1.57-1.68 (m, 3H), 1.73-1.88 (m, 4H), 2.39 (dd, 1H, J$_1$=10.1, J$_2$=17.1), 2.83 (dd, 1H, J$_1$=8.7, J$_2$=17.8), 3.58-3.68 (m, 1H), 3.86-3.96 (m, 1H), 4.09-4.18 (m, 1H), 4.67-4.77 (m, 1H), 5.08-5.17 (m, 3H), 5.43 (d, 1H, J=4.5), 6.56 (d, 1H, J=7.9), 7.30-7.40 (m, 5H); HPLC-MS calcd. for C$_{22}$H$_{30}$N$_2$O$_6$ (M+H$^+$) 419.2, found 419.5.

Step B. The title compound was prepared in 71% yield in an analogous manner to example 1, step B except that (3S)-[(2S)-benzyloxycarbonylamino-3-cycopentyl-propionylamino]-(2R)-ethoxy-5-oxo-tetrahydrofuran was used as the starting material: $^1$H NMR (CDCl$_3$, 400 MHz) δ 1.13-1.27 (m, 2H), 1.25 (t, 3H, J =8.7), 1.48-1.70 (m, 4H), 1.78-2.03 (m, 5H), 2.48 (dd, 1H, J$_1$=10.4, J$_2$=17.4), 2.85 (dd, 1H, J$_1$=8.6, J$_2$=17.4), 3.65 (dq, 1H, J$_1$=7.1, J$_2$=9.6), 3.92 (dq, 1H, J$_1$=7.1, J$_2$=9.6), 4.56-4.64 (m, 1H), 4.70-4.79 (m, 1H), 5.47 (d, 1H, J=5.3), 6.74 (d, 1H, J=8.0), 6.77 (d, 1H, J=3.6), 6.80 (d, 1H, J=8.2), 7.02-7.08 (m, 1H), 7.21 (d, 1H, J=3.6), 7.36-7.43 (m, 2H), 7.47-7.52 (m, 1H); HPLC-MS calcd. for C$_{25}$H$_{29}$FN$_2$O$_6$ (M+H$^+$) 473.2, found 473.5.

Example 15

(3S)-(3-Cyclohexyl-(2S)-{[5-(3-fluoro-phenyl)-furan-2-carbonyl]-amino}-propionylamino)-4-oxo-butyric acid

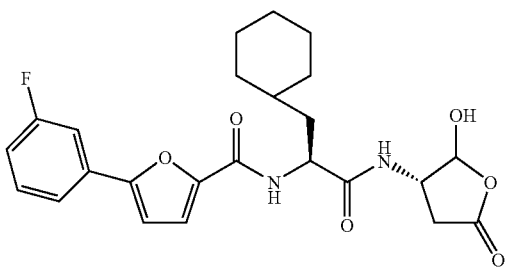

Step A. 0.168 g of 3-Fluorophenylboronic acid (1.2 mmol, 1.2 equiv.), 0.191 g of 5-bromo-furan-2-carboxylic acid (1.0 mmol, 1 equiv.), 0.375 mL of saturated sodium carbonate, and 0.018 mg of dichloro (1,1-bis(diphenylphosphino)ferrocene) palladium(II) methylene chloride adduct (0.025 mmol, 2 mol %) were added to a microwave tube, adding dry reagents first followed by 2 mL of water and then base, the tube was capped and the vial purged with an appropriate inert gas such as nitrogen or argon. The tube was sonicated for 5 minutes to break up any large lumps and the reaction was heated in a microwave for a fixed time of 120 seconds at 200° C. The slurry was acidified with citric acid and the product was extracted into ethyl acetate. The organic layer was dried over MgSO$_4$, filtered and concentrated to dryness resulting in 0.198 g of product as a light pink material. This product was 98% pure and was suitable for further synthesis as is. LC/MS found: 207 (M+H$^+$).

Step B. The title compound was synthesized by the same exact route as example 1 except S-cyclohexylalanine was used in place of S-cyclopentylalanine. The product was isolated as a mixture of diastereomers about the lactol bond. LC-MS calculated for C$_{24}$H$_{27}$FN$_2$O$_6$ M+H$^+$: 459.18, found 459.1.

Example 16

(3S)-[3-Cyclohexyl-(2S)-{[5-(3-fluoro-phenyl)-furan-2-carbonyl]-amino}propionylamino]-2-methoxy-5-oxo-tetrahydrofuran

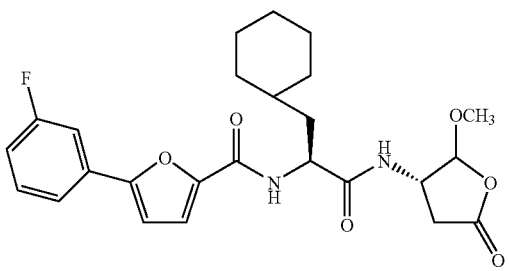

The title compound was synthesized directly from the product of example 15 by dissolving 450 mg of which in 8 mL of dry methanol, a trace amount of TFA was added and the reaction was allowed to stir for 15 min. The product was

Example 17

(3S)-[3-Cyclohexyl-(2S)-{[5-(3-fluoro-phenyl)-furan-2-carbonyl]-amino}propionylamino]-2-ethoxy-5-oxo-tetrahydrofuran

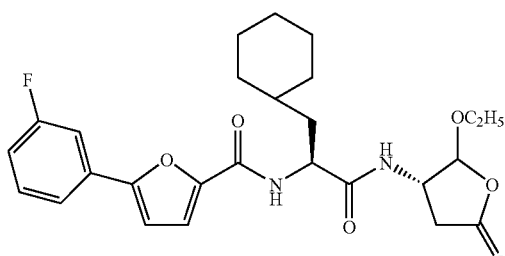

The title compound was synthesized from the product of example 15 by dissolving 80 mg of which in 5 mLs of dry ethanol. Triethylorthoformate (1 mL) was added as well as a trace amount of formic acid. The reaction was allowed to stir overnight and the crude product was purified by reverse phase prep HPLC. Yield 25 mg. $^1$H NMR (CDCl$_3$, 400 MHz), δ 7.49 (d, J=7.9 Hz, 1H), 7.43-7.37 (m, 2H), 7.29 (d, J=3.5 Hz, 1H), 7.05 (td, J=8.3, 2.5 Hz, 1H), 6.77 (d, J=3.5 Hz, 1H), 6.74 (t, J=7.9 Hz, 2H), 5.47 (d, J=5.3 Hz, 1H), 4.79-4.65 (m, 2H), 3.96-3.88 (m, 1H), 3.7-3.62 (m, 1H), 2.88-2.82 (m, 1H), 2.5-2.43 (m, 1H), 1.87-1.64 (m, 7H), 1.45-1.33 (m, 1H), 1.31-1.11 (m, 6H), 1.08-0.89 (m, 2H). HPLC-MS calcd. for C$_{26}$H$_{31}$FN$_2$O$_6$ (M+H$^+$) 487.2, found 487.2.

Example 18

(3S)-((2S)-(3-cyanophenyl-carbonylamino)-3-cyclopentyl-propionylamino)-4-oxo-butyric acid

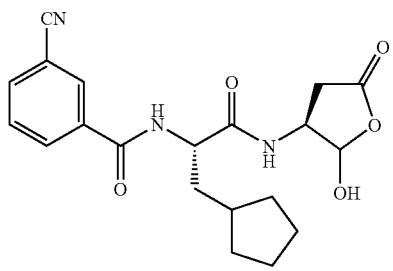

$^1$H NMR (CD$_3$OD, 400 MHz) δ 8.21 (m, 1H), 8.14 (m, 1H), 7.88 (m, 1H), 7.66 (dd, J=7.9, 7.8 Hz, 1H), 4.58 (m, 1H), 4.30 (m, 1H), 2.68 (ddd, J=16.1, 10.4, 5.1 Hz, 1H), 2.52 (ddd, J=16.1, 8.2, 2.8 Hz, 1H), 1.82-1.96 (m, 6H), 1.65 (m, 2H), 1.56 (m, 2H), 1.23 (m, 1H), 0.91 (m, 1H); HPLC-MS calcd. for C$_{20}$H$_{24}$N$_3$O$_5$ (M +H$^+$) 386.4, found 386.5.

Example 19

(3S)-(3-Cyclopentyl-(2S)-(cyclopropylcarbonylamino)-propionylamino)-4-oxo-butyric acid

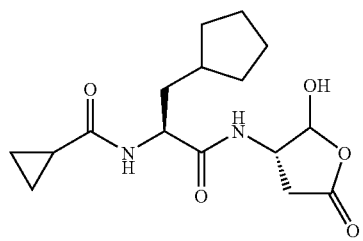

HPLC-MS calcd. for C$_{16}$H$_{24}$N$_2$O$_5$ (M+H$^+$) 325.2, found 325.4.

Example 20

(3S)-(3-Cyclopentyl-(2S)-(tetrahydro-pyran-4-yloxy-carbonylamino)-propionylamino)-4-oxo-butyric acid HPLC-MS calcd. for C$_{18}$H$_{28}$N$_2$O$_7$ (M+H$^+$) 385.2, found 385.4.

Example 21

(3S)-(3-Cyclopropyl-(2S)-(cyclopropylcarbonylamino)-propionylamino)-4-oxo-butyric acid

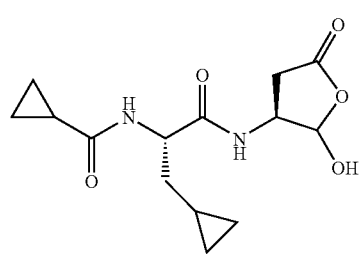

$^1$H NMR (CD$_3$OD, 600 MHz) δ 4.57 (dd, J=7.8, 3.9 Hz, 1H), 4.39 (dd, J=7.8, 6.2 Hz), 4.27 (m, 1H), 2.50 (m, 1H), 1.58-1.68 (m, 1H), 0.84 (m, 3H), 0.77 (m, 4H), 0.47 (m, 3H), 0.09-0.17 (m, 2H); HPLC-MS calcd. for C$_{14}$H$_{21}$N$_2$O$_5$ (M + H$^+$) 297.3, found 297.4.

Example 22

(3 S)-((2S)-(cyclopropylcarbonylamino)-4,4-dimethyl-pentanoylamino)-4-oxo-butyric acid

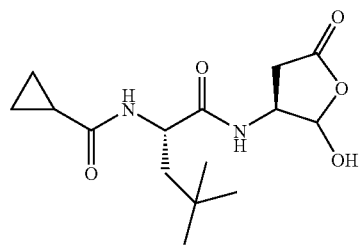

$^1$H NMR (CD$_3$OD, 600 MHz) δ 4.56 (dd, J=8.6, 4.0 Hz, 1H), 4.43 (m, 1H), 4.22 (m, 1H), 2.48 (m, 1H), 1.79 (m, 1H), 1.62 (m, 2H), 1.53 (m, 1H), 0.95 (s, 9H), 0.86 (m, 4H), 0.76 (m, 3H); HPLC-MS calcd. for C$_{15}$H$_{25}$N$_2$O$_5$ (M +H$^+$) 313.4, found 313.6.

Example 23

(3S)-(3-Cyclopentyl-(2S)-{[5-(3-trifluoromethyl-phenyl)-furan-2-carbonyl]-amino}-propionylamino)-4-oxo-butyric acid

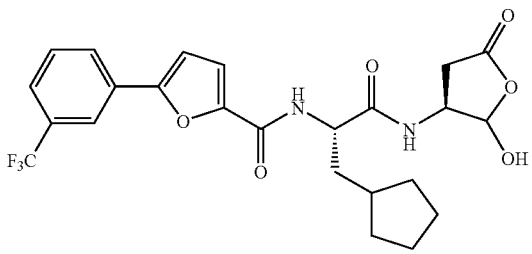

$^1$H NMR (CD$_3$OD, 600 MHz) δ 8.25 (m, 1H), 8.14 (m, 1H), 7.66 (m, 2H), 7.29 (m, (d, J=3.6 Hz, 1H), 5.36 (m, 1H), 4.60 (m, 1H), 4.30 (m, 1H), 2.67 (m, 1H), 2.50 (m, 1H), 1.90 (m, 5H), 1.63 (m, 2H), 1.58 (m, 2H), 1.25 (2H); HPLC-MS calcd. for C$_{24}$H$_{26}$F$_3$N$_2$O$_6$ (M+H$^+$) 495.5, found 495.2.

Example 24

(3S)-(3-Cyclopentyl-(2S)-(3-trifluoromethylphenyl-carbonylamino)-propionylamino)-4-oxo-butyric acid

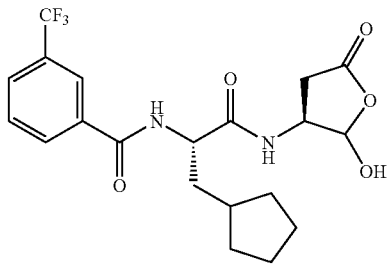

$^1$H NMR (CD$_3$OD, 600 MHz) δ 8.19 (m, 1H), 8.12 (m, 1H), 7.86 (m, 1H), 7.69 (m, 1H), 5.48 (m, 1H), 4.60 (m, 1H), 4.30 (m, 1H), 2.66 (m, 1H), 2.53 (m, 1H), 1.90 (m, 5H), 1.67 (m, 2H), 1.58 (m, 2H), 1.26 (m, 2H); HPLC-MS calcd. for C$_{20}$H$_{24}$F$_3$N$_2$O$_5$ (M +H$^+$) 429.4, found 429.2.

Example 25

(3 S)-[3-Cyclopentyl-(2S)-{[5-(3-fluoro-phenyl)-furan-2-carbonyl]-amino}propionylamino]-2-isopropoxy-5-oxo-tetrahydrofuran

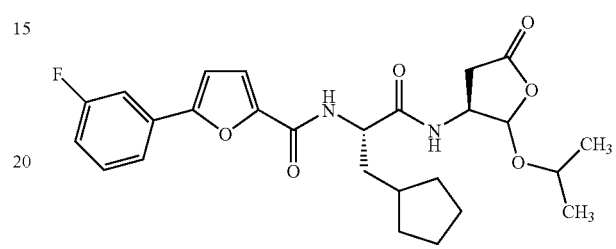

$^1$H NMR (CDCl$_3$, 400 MHz) δ 7.82 (m, 1H), 7.48 (m, 1H), 7.37 (m, 2H), 7.23 (d, J=3.6 Hz, 1H), 7.11 (m, 1H), 7.03 (ddd, J=10.8, 2.3, 2.3 Hz, 1H), 6.76 (d, J=3.6 Hz, 1H), 4.71 (m, 1H), 4.31 (m, 1H), 3.97 (m, 1H), 2.97 (dd, J=18.0, 7.7 Hz, 1H), 2.45 (dd, J=18.0, 1.8 Hz, 1H), 1.89 (m, 6H), 1.60 (m, 2H), 1.52 (m, 2H), 1.21 (dd, J=6.1, 4.8 Hz, 6H), 1.17 (m, 2H); HPLC-MS calcd. for C$_{26}$H$_{32}$FN$_2$O$_6$ (M+H$^+$) 487.5, found 487.3.

Example 26

(3S)-[3-Cyclopentyl-(2S)-{[5-(3-fluoro-phenyl)-furan-2-carbonyl]-amino}propionylamino]-2-cyclopentoxy-5-oxo-tetrahydrofuran Calculated [M+H] for C$_{28}$H$_{34}$FN$_2$O$_6$ 513.6. Found: 513.3

Example 27

(3 S)-[3-Cyclopentyl-(2S)-{[5-(3-fluoro-phenyl)-furan-2-carbonyl]-amino}propionylamino]-2-cyclopentylmethoxy-5-oxo-tetrahydrofuran

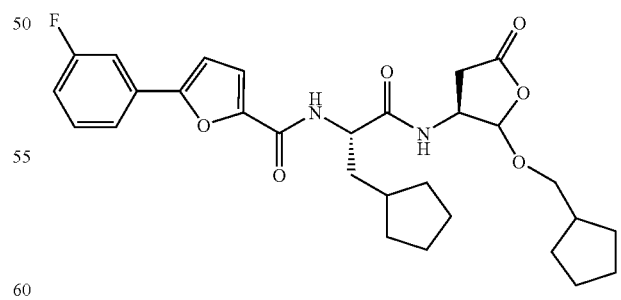

$^1$H NMR (CDCl$_3$, 400 MHz) δ 7.50 (m, 1H), 7.41 (m, 2H), 7.22 (d, J=3.6 Hz, 1H), 7.06 (m, 1H), 6.78 (d, J=3.6 Hz, 1H), 6.73 (dd, J=21.0, 8.3 Hz, 1H), 5.46 (d, J=5.3 Hz, 1H), 4.76 (m, 1H), 4.61 (m, 1H), 3.76 (dd, J=9.2, 7.1 Hz, 1H), 3.44 (dd, J=9.1, 7.5 Hz, 1H), 2.87 (dd, J=17.4, 8.6 Hz, 1H), 2.47 (dd, J=17.4, 10.3 Hz, 1H), 2.15 (m, 1H), 1.94 (m, 1H), 1.83 (m, 4H), 1.63-1.74 (m, 6H), 1.47-1.58 (m, 5H), 1.19 (m, 4H); HPLC-MS calcd. for $C_{29}H_{36}FN_2O_6$ (M+H$^+$) 527.6, found 527.3.

B. Assays for Cathepsin Inhibitory Activity

Cathepsin S

The optimal substrate for cathepsin S, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci U S A* 2000, 97(14), 7754-9). Kinetic measurements are performed in a total reaction volume of 30 μl in 384-well microtiter plates. Cathepsin S, at a final concentration of 0.3-3 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 50 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin K

The optimal substrate for cathepsin K, acetyl-lysine-histidine-proline-lysine-amino carbamoyl coumarin, was identified from screening a combinatorial library of fluorogenic peptide substrates (Harris, J. L., B. J. Backes, et al., *Proc Natl Acad Sci USA* 2000, 97(14), 7754-9). Kinetic measurements are performed in a total reaction volume of 30 μl in 384-well microtiter plates. Cathepsin K, at a final concentration of 3.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-lysine-histidine-proline-lysine-amino carbamoyl coumarin, to a final concentration of 40 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Catheipsin L

The optimal substrate for cathepsin L, acetyl-histidine-lysine-phenylalanine-lysine-amino carbamoyl coumarin, was identified from screening a combinatorial library of fluorogenic peptide substrates (Harris, J. L., B. J. Backes, et al.; *Proc Natl Acad Sci USA* 2000, 97(14), 7754-9). Kinetic measurements are performed in a total reaction volume of 30 μl in 384-well microtiter plates. Cathepsin L, at a final concentration of 0.1 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-lysine-phenylalanine-lysine-amino carbamoyl coumarin, to a final concentration of 20 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Cathepsin B

The optimal substrate for cathepsin B, acetyl-histidine-proline-valine-lysine-amino carbamoyl coumarin, was identified from screening a combinatorial library of fluorogenic peptide substrates (Harris, J. L., B. J. Backes, et al., *Proc Natl Acad Sci US A* 2000, 97(14), 7754-9). Kinetic measurements are performed in a total reaction volume of 30 μl in 384-well microtiter plates. Cathepsin B, at a final concentration of 1.5 nM (active site), is incubated with the compounds at twelve varying concentrations in a buffer containing 100 mM NaAc (pH5.5), 1 mM EDTA, 100 mM NaCl, 0.01% Brij-35 for 20 minutes at room temperature. Control reactions in the absence of inhibitor are performed in replicates of 24. The reactions are initiated by adding the substrate, acetyl-histidine-proline-valine-lysine-amino carbamoyl coumarin, to a final concentration of 10 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, P., K. C. Elrod, et al., *Anal Biochem* 2000, 286(1), 45-50) and are then used to calculate the inhibition constants for competitive inhibitors.

Preferred cathepsin S inhibition constants for compounds of the present invention are less than 10 μM. More preferred inhibition constants for compounds of the present invention are less than 1.0 μM. Most preferred inhibition constants for compounds of the present invention are less than 0.1 μM.

Selectivity for cathepsin S in the presence of cathepsin isozymes was determined by the ratio of the cathepsin isozyme inhibition constant of a compound of the present invention to the cathepsin S inhibition constant of the same compound. Preferred compounds of the present invention selective for cathepsin S have ratios of greater than 10. More preferred compounds of the present invention selective for cathepsin S have ratios of greater than 100. Most preferred compounds of the present invention selective for cathepsin S have ratios of greater than 1000.

TABLE I

Assay Data for Inhibitors of Cathepsin S

| Example | $K_i$ Cat. S$^a$ | Selectivity for Cat. S over Cat. K$^b$ | Selectivity for Cat. S over Cat. L$^b$ | Selectivity for Cat. S over Cat. B$^b$ |
|---|---|---|---|---|
| 1 | +++ | + | ++ | +++ |
| 2 | +++ | ++ | ++ | +++ |
| 3 | +++ | + | + | +++ |
| 4 | +++ | + | ++ | +++ |

TABLE I-continued

Assay Data for Inhibitors of Cathepsin S

| Example | $K_i$ Cat. S[a] | Selectivity for Cat. S over Cat. K[b] | Selectivity for Cat. S over Cat. L[b] | Selectivity for Cat. S over Cat. B[b] |
|---|---|---|---|---|
| 5 | +++ | + | + | +++ |
| 6 | +++ | ++ | ++ | +++ |
| 7 | +++ | ++ | ++ | +++ |
| 8 | +++ | ++ | ++ | +++ |
| 9 | +++ | − | ++ | ++ |
| 10 | +++ | ++ | +++ | +++ |
| 11 | +++ | + | − | + |
| 12 | +++ | + | ++ | ++ |
| 13 | ++ | − | + | ++ |
| 15 | +++ | ++ | ++ | +++ |
| 16 | ++ | + | + | + |
| 18 | +++ | ++ | + | +++ |
| 19 | +++ | ++ | +++ | +++ |
| 20 | +++ | ++ | ++ | +++ |
| 21 | +++ | + | ++ | ++ |
| 22 | +++ | + | +++ | +++ |
| 23 | +++ | ++ | +++ | +++ |
| 24 | +++ | ++ | + | +++ |
| 26 | +++ | + | +++ | +++ |

[a]Cathepsin S inhibition constant for compounds of Formula I: +, <10 μM; ++, <1.0 μM; +++, <0.1 μM.
[b]Selectivity of compounds of Formula I for cathepsin S over another cathepsin: +, >10; ++, >100; +++, >1000.

C. Assays for Caspase Inhibitory Activity

Caspases (cysteinyl aspartate-specific proteases) are a family of cysteine proteases with at least 12 human members and strong phylogenetic conservation, which have been found to play critical roles in both cytokine maturation and apoptosis (R. V. Talanian et al. *J. Med. Chem.* 2000, 43, 3351; S. Ashwell *Expert Opin. Ther. Patents* 2001, 11, 1593).

Inhibition Assay for Caspase 1:

The widely used substrate for caspase 1, acetyl-tryptophan-glutamate-histidine-spartic acid-amino carbamoyl coumarin, was used. Kinetic measurements are performed in a total reaction volume of 30 μl in 384-well microtiter plates. Caspase 1, at a final concentration of 0.2-1 nM (active site), is incubated with the compounds at twelve varying concentrations in a buffer containing 20 mM Hepes (pH 7.4), 1 mM EDTA, 100 mM NaCl, 0.1% CHAPS, 10% sucrose, 10 mM DTT for 20 minutes at room temperature. Control reactions in the absence of inhibitor are performed in replicates of 12. The reactions are initiated by adding the substrate to a final concentration of 4 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, Elrod et al. 2000) and are then used to calculate the inhibition constants for competitive inhibitors (Km=8 μM).

Inhibition Assay for Caspase 3:

The widely used substrate for caspase 3, acetyl-aspartate-glutamate-valine-aspartic acid-amino carbamoyl coumarin, was used. Kinetic measurements are performed in a total reaction volume of 30 μl in 384-well microtiter plates. Caspase 3, at a final concentration of 0.2-1 nM (active site), is incubated with the compounds at twelve varying concentrations in a buffer containing 20 mM Hepes (pH7.4), 1 mM EDTA, 100 mM NaCl, 0.1% CHAPS, 10% sucrose, 10 mM DTT for 20 minutes at room temperature. Control reactions in the absence of inhibitor are performed in replicates of 12. The reactions are initiated by adding the substrate to a final concentration of 2 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, Elrod et al. 2000) and are then used to calculate the inhibition constants for competitive inhibitors (Km=9.71 μM).

Inhibition Assay for Caspase 8:

The widely used substrate for caspase 8, acetyl-aspartate-glutamate-valine-aspartic acid-amino carbamoyl coumarin, was used. Kinetic measurements are performed in a total reaction volume of 30 μl in 384-well microtiter plates. Caspase 8, at a final concentration of 0.2-1 nM (active site), is incubated with the compounds at twelve varying concentrations in a buffer containing 20 mM Hepes (pH 7.4), 1 mM EDTA, 100 mM NaCl, 0.1% CHAPS, 10% sucrose, 10 mM DTT for 20 minutes at room temperature. Control reactions in the absence of inhibitor are performed in replicates of 12. The reactions are initiated by adding the substrate to a final concentration of 2 μM. The rate of substrate hydrolysis is measured by monitoring the increase in fluorescence at an excitation wavelength of 380 nm and an emission wavelength of 450 nm that results from cleavage of the aniline bond in the substrate by the enzyme. The apparent inhibition constants for the compounds are determined from the enzyme progress curves (Kuzmic, Elrod et al. 2000) and are then used to calculate the inhibition constants for competitive inhibitors (Km=25.7 μM).

TABLE II

Assay Data for Inhibitors of Caspase

| Example | $K_i$ Cas-1 | $K_i$ Cas-3 | $K_i$ Cas-8 |
|---|---|---|---|
| 1 | 0 | 0 | 0 |
| 2 | 000 | 00 | 00 |
| 3 | 00 | 00 | 00 |
| 4 | 00 | 00 | 00 |
| 5 | 00 | 00 | 00 |
| 6 | 000 | 00 | 00 |
| 7 | 00 | 00 | 00 |
| 8 | 000 | 0 | 00 |
| 9 | 000 | 000 | 000 |
| 10 | 000 | 000 | 000 |

Caspase -1, -3 and -8 inhibition constant for compounds of Formula I:: 0, >1 μM.; 00, >10 μM.; 000, >100 μM.

Although the foregoing invention has been described in some detail by way of illustration and example for purposes of clarity of understanding, it will be obvious that certain changes and modifications may be practiced within the scope of the appended claims. In addition, each reference provided herein is incorporated by reference in its entirety to the same extent as if each reference was individually incorporated by reference.

What is claimed is:

1. A compound having Formula (I):

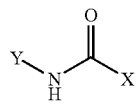

or a pharmaceutically acceptable salt or prodrug thereof, wherein:

Y is

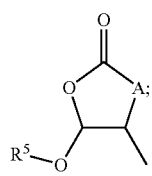

A is a member selected from the group consisting of —$CH_2$—, and —$CH_2CH_2$—;

$R^5$ is independently a member selected from the group consisting of H, $C_1$-$C_6$ alkyl, $C_3$-$C_8$ cycloalkyl, $C_1$-$C_4$ alkyl substituted $C_3$-$C_8$ cycloalkyl, and benzyl;

X is a member selected from the group consisting of —O—$CR^1R^2$—C(=O)—Q, —$CR^3$H—O—C(=O)—W, —$CH_2$—$CHR^3$—C(=O)—W, —$CR^3$H—$CH_2$—C(=O)—W, —$CR^4$H—NH—C(=O)—W, —O—$CR^1R^2$—B—$R^6$, —$CR^3$H—NH—C(=O)—O—Z, —$CHR^4$—NH—C(=O)—$R^7$, and —$CHR^4$—NH—S(=O)$_2$—$R^8$;

Q is a heterocycle selected from the group consisting of pyrrolidinyl, piperidyl, morpholinyl, thiomorpholinyl, piperazinyl and indolinyl substituted with 0-2 $R^Q$, wherein Q is connected to —C(=O)— via a ring nitrogen atom;

each $R^Q$ is independently a member selected from the group consisting of OH, —S(=O)$_2$CH$_3$, acetyl, =O, $C_1$-$C_6$ alkyl, $C_1$-$C_6$ alkoxy, CF$_3$, OCF$_3$ and NR$^{10}$R$^{11}$;

W is morpholinyl, wherein W is connected to —C(=O)— via the ring nitrogen atom;

Z is a heterocycle selected from the group consisting of tetrahydrofaranyl, tetrahydropyranyl, thiotetrahydropyranyl, thiotetrahydrofuranyl, pyrrolidinyl, piperidyl, morpholinyl, thiomorpholinyl, piperazinyl and indolinyl each substituted with 0-2 $R^Z$, wherein Z is connected to —O—C(=O)— via a ring carbon atom;

each $R^Z$ is independently a member selected from the group consisting of OH, —S(=O)$_2$CH$_3$, acetyl, =O, $C_1$-$C_6$ alkyl, $C_1$-$C_6$ alkoxy, CF$_3$, OCF$_3$ and NR$^{10}$R$^{11}$;

B is a member selected from the group consisting of —$CH_2$—, —$OCH_2$—, —NR$^{11}$CH$_2$—, —$CH_2CH_2$— and a bond;

each $R^1$ is independently a member selected from the group consisting of H, a $C_1$-$C_6$ alkyl substituted with 0-2 $R^{1a}$, wherein said $C_1$-$C_6$ alkyl is optionally substituted with a heteroatom selected from the group consisting of —O—, —S—, —S(=O)—, and —S(=O)$_2$—; a $C_2$-$C_6$ alkenyl, a $C_3$-$C_6$ alkynyl, a $C_3$-$C_7$ cycloalkyl each substituted with 0-2 $R^{1b}$, and a $C_7$-$C_{11}$ bicycloalkyl substituted with 0-2 $R^{1b}$; phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;

each $R^{1a}$ is independently a member selected from the group consisting of a $C_6$-$C_{10}$ aryl substituted with 0-3 $R^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1c}$, a $C_3$-$C_8$ cycloalkyl substituted with 0-2 $R^{1b}$, a $C_7$-$C_{11}$ bicycloalkyl substituted with 0-2 $R^{1b}$, and a $C_1$-$C_3$ perfluoroalkyl;

each $R^{1b}$ is independently a member selected from the group consisting of a H, $C_1$-$C_6$ alkyl, $C_1$-$C_6$ alkoxy, CF$_3$, OCF$_3$, —S(=O)$_2$CH$_3$, and acetyl;

each $R^{1c}$ is independently a member selected from the group consisting of a H, OH, F, Cl, Br, CN, NO$_2$, COOR$^{12}$, C(=O)NR$^{12}$R$^{11}$, S(=O)$_2$NR$^{12}$R$^{11}$, acetyl, —SCH$_3$, —S(=O)CH$_3$, —S(=O)$_2$CH$_3$, —NR$^{10}$R$^{11}$, $C_1$-$C_6$ alkoxy, $C_1$-$C_3$ perfluoroalkyl, $C_1$-$C_3$ perfluoroalkoxy and a $C_1$-$C_6$ alkyl;

each $R^2$ is independently a member selected from the group consisting of H and $C_1$-$C_6$ alkyl;

each $R^3$ is a $C_1$-$C_2$ alkyl substituted with 1 $R^{3a}$;

each $R^{3a}$ is independently a member selected from the group consisting of a $C_3$-$C_7$ cycloalkyl substituted with 0-2 $R^{1b}$, and a $C_7$-$C_{11}$ bicycloalkyl substituted with 0-2 $R^{1b}$;

each $R^4$ is a $C_1$-$C_2$ alkyl substituted with 1 $R^{4a}$;

each $R^{4a}$ is independently a member selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;

$R^6$ is independently a member selected from group consisting of a 5- to 6-membered monocyclic heteroaryl containing 1 to 4 heteroatoms each independently a member selected from the group consisting of N, O and S, wherein said heteroaryl is substituted with 1 $R^{6a}$ and 0-2 $R^{1c}$; and a 8- to 10-membered bicyclic heteroaryl containing 1 to 4 heteroatoms each independently a member selected from the group consisting of N, O and S, wherein said heteroaryl is substituted with 0-3 $R^{1c}$;

each $R^{6a}$ is independently a member selected from the group consisting of phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;

$R^7$ is a member selected from the group consisting of a 5-membered heteroaryl containing 1 to 4 heteroatoms each independently a member selected from the group consisting of N, O and S, wherein said heteroaryl is substituted with 1 $R^{6a}$ and 0-2 $R^{1c}$, a phenyl substituted with 0-3 $R^{1c}$, OCH$_2$Ph, O-tert-Bu, and $C_3$-$C_6$ cycloalkyl;

$R^8$ is a member selected from the group consisting of a phenyl substituted with 0-3 $R^{1c}$, and a 5- to 6-membered heteroaryl containing 1 to 4 heteroatoms each independently a member selected from the group consisting of N, O and S, wherein said heteroaryl is substituted with 0-3 $R^{1c}$;

each $R^{10}$ is independently a member selected from the group consisting of H, $C_1$-$C_4$ alkyl, ($C_1$-$C_4$ alkyl)-C(=O)— and ($C_1$-$C_4$ alkyl)-S(=O)$_2$—;

each $R^{11}$ is independently a member selected from the group consisting of H and $C_1$-$C_4$ alkyl; and each $R^{12}$ is independently a member selected from the group consisting of H and $C_1$-$C_4$ alkyl.

2. The compound of claim 1, wherein said compound has formula Ia:

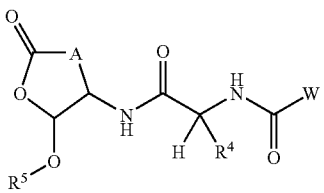

Ia wherein:

A is —$CH_2$—;

$R^4$ is a $C_1$-$C_2$ alkyl substituted with 1 $R^{4a}$;

$R^{4a}$ is selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —$S(=O)_2CH_3$, and acetyl; and W is morpholinyl, wherein W is connected to —C(=O)— via the ring nitrogen atom.

3. The compound of claim 1, wherein said compound has formula Ib:

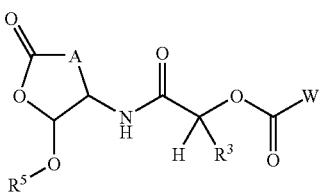

Ib wherein:

A is —$CH_2$—;

$R^3$ is a $C_1$-$C_2$ alkyl substituted with 1 $R^{3b}$;

$R^{3a}$ is selected from the group consisting of a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —$S(=O)_2CH_3$, and acetyl; and W is morpholinyl, wherein W is connected to —C(=O)— via the ring nitrogen atom.

4. The compound of claim 1, wherein said compound has formula Ic:

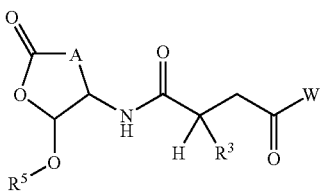

Ic wherein:

A is —$CH_2$—;

$R^3$ is a $C_1$-$C_2$ alkyl substituted with 1 $R^{3a}$;

$R^{3a}$ is selected from the group consisting of a $C_3$-$C_7$ cycloalkyl substituted with 0-2 $R^{1b}$, and a $C_7$-$C_{11}$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —$S(=O)_2CH_3$, and acetyl; and W is morpholinyl, wherein W is connected to —C(=O)— via the ring nitrogen atom.

5. The compound of claim 1, wherein said compound has formula Id:

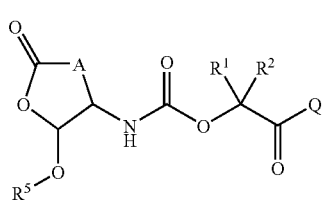

Id wherein:

A is —$CH_2$—;

$R^1$ is independently a member selected from the group consisting of H, a $C_1$-$C_6$ alkyl substituted with 0-2 $R^{1a}$, wherein said $C_1$-$C_6$ alkyl is optionally substituted with a heteroatom selected from the group consisting of —O—, —S—, —S(=O)— and —$S(=O)_2$—; a $C_2$-$C_6$ alkenyl, a $C_3$-$C_6$ alkynyl, a $C_3$-$C_7$ cycloalkyl each substituted with 0-2 $R^{1b}$, and a $C_7$-$C_{11}$ bicycloalkyl substituted with 0-2 $R^{1b}$; phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;

each $R^{1a}$ is independently a member selected from the group consisting of a $C_6$-$C_{10}$ aryl substituted with 0-3 $R^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1c}$, a $C_3$-$C_8$ cycloalkyl substituted with 0-2 $R^{1b}$, a $C_7$-$C_{11}$ bicycloalkyl substituted with 0-2 $R^{1b}$, and a $C_1$-$C_3$ perfluoroalkyl;

each $R^{1b}$ is independently a member selected from the group consisting of a H, $C_1$-$C_6$ alkyl, $C_1$-$C_6$ alkoxy, $CF_3$, $OCF_3$, —$S(=O)_2CH_3$, and acetyl;

each $R^{1c}$ is independently a member selected from the group consisting of a H, OH, F, Cl, Br, CN, $NO_2$, $COOR^{12}$, $C(=O)NR^{12}R^{11}$, $S(=O)_2NR^{12}R^{11}$, acetyl, —$SCH_3$, —$S(=O)CH_3$, —$S(=O)_2CH_3$, —$NR^{10}R^{11}$, $C_1$-$C_6$ alkoxy, $C_1$-$C_3$ perfluoroalkyl, $C_1$-$C_3$ perfluoroalkoxy and a $C_1$-$C_6$ alkyl;

each $R^2$ is independently a member selected from the group consisting of H and $C_1$-$C_6$ alkyl;

Q is a heterocycle selected from the group consisting of pyrrolidinyl, piperidyl, morpholinyl, thiomorpholinyl, piperazinyl and indolinyl substituted with 0-2 $R^Q$, wherein Q is connected to —C(=O)— via a ring nitrogen atom; and each $R^Q$ is independently a member selected from the group consisting of OH, —$S(=O)_2CH_3$, acetyl, =O, $C_1$-$C_6$ alkyl, $C_1$-$C_6$ alkoxy, $CF_3$, $OCF_3$ and $NR^{10}R^{11}$.

6. The compound of claim 5 wherein:
$R^1$ is a $C_1$-$C_2$ alkyl substituted with 1 $R^{4a}$;
$R^{4a}$ is selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;
each $R^{1b}$ is independently a member selected from the group consisting of a H, $C_1$-$C_6$ alkyl, $C_1$-$C_6$ alkoxy, $CF_3$, $OCF_3$, —$S(=O)_2CH_3$, and acetyl;
$R^2$ is H; and
Q is a member selected form the group consisting of morpholinyl, pyrrolidinyl, piperidyl, and piperazinyl, wherein Q is connected to —C(=O)— via a ring nitrogen.

7. The compound of claim 1, wherein said compound has formula Ie:

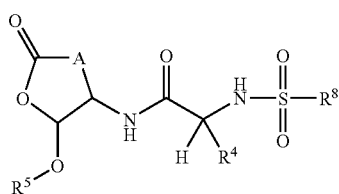

wherein:
A is —$CH_2$—;
$R^4$ is a $C_1$-$C_2$ alkyl substituted with 1 $R^{4a}$;
$R^{4a}$ is selected from the group consisting of a tert-butyl, a $C_3$-$C_7$ cycloalkyl substituted with 0-2 $R^{1b}$, and a $C_7$-$C_{11}$ bicycloalkyl substituted with 0-2 $R^{1b}$;
each $R^{1b}$ is independently selected from the group consisting of a H, $C_1$-$C_6$ alkyl, $C_1$-$C_6$ alkoxy, $CF_3$, $OCF_3$, —$S(=O)_2CH_3$, and acetyl;
$R^8$ is a member selected from the group consisting of a phenyl substituted with 0-3 $R^{1c}$, and a 5- to 6-membered heteroaryl containing 1 to 4 heteroatoms each independently a member selected from the group consisting of N, O and S, wherein said heteroaryl is substituted with 0-3 $R^{1c}$; and
each $R^{1c}$ is independently a member selected from the group consisting of a H, OH, F, Cl, Br, CN, $NO_2$, $COOR^{12}$, $C(=O)NR^{12}R^{11}$, $S(=O)_2NR^{12}R^{11}$, acetyl, —$SCH_3$, —$S(=O)CH_3$, —$S(=O)_2CH_3$, —$NR^{10}R^{11}$, $C_1$-$C_6$ alkoxy, $C_1$-$C_3$ perfluoroalkyl, $C_1$-$C_3$ perfluoroalkoxy and a $C_1$-$C_6$ alkyl.

8. The compound of claim 1, wherein said compound has formula If:

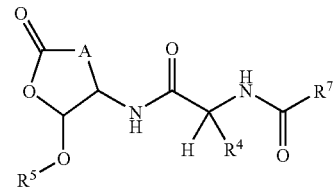

wherein:
A is —$CH_2$—
$R^4$ is a $C_1$-$C_2$ alkyl substituted with 1 $R^{4a}$;
$R^{4a}$ is selected from the group consisting of a tert-butyl, a $C_3$-$C_7$ cycloalkyl substituted with 0-2 $R^{11}$, and a $C_7$-$C_1$ bicycloalkyl substituted with 0-2 $R^{1b}$;

each $R^{1b}$ is independently selected from the group consisting of a H, $C_1$-$C_6$ alkyl, $C_1$-$C_6$ alkoxy, $CF_3$, $OCF_3$, —$S(=O)_2CH_3$, and acetyl;
$R^7$ is a member selected from the group consisting of a 5-membered heteroaryl containing 1 to 4 heteroatoms each independently a member selected from the group consisting of N, O and S, wherein said heteroaryl is substituted with 1 $R^{6a}$ and 0-2 $R^{1c}$; a phenyl substituted with 0-3 $R^{1c}$, $OCH_2Ph$, O-tert-Bu, and $C_3$-$C_6$ cycloalkyl;
each $R^{1c}$ is independently a member selected from the group consisting of a H, OH, F, Cl, Br, CN, $NO_2$, $COOR^{12}$, $C(=O)NR^{12}R^{11}$, $S(=O)_2NR^{12}R^{11}$, acetyl, —$SCH_3$, —$S(=O)CH_3$, —$S(=O)_2CH_3$, —$NR^{10}R^{11}$, $C_1$-$C_6$ alkoxy, $C_1$-$C_3$ perfluoroalkyl, $C_1$-$C_3$ perfluoroalkoxy and a $C_1$-$C_6$ alkyl; and
each $R^{6a}$ is independently a member selected from the group consisting of phenyl substituted with 0-3 $R^{1c}$; a 5- to 6-membered heteroaryl containing 1 to 4 heteroatoms each independently a member selected from the group consisting of N, O and S, wherein said heteroaryl is substituted with 0-3 $R^{1c}$.

9. The compound of claim 1, wherein said compound has formula Ig

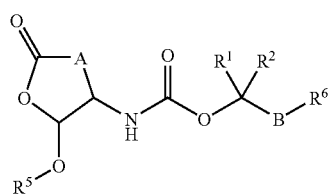

wherein:
A is —$CH_2$—;
each $R^1$ is independently a member selected from the group consisting of H, a $C_1$-$C_6$ alkyl substituted with 0-2 $R^{1a}$, wherein said $C_1$-$C_6$ alkyl is optionally substituted with a heteroatom selected from the group consisting of —O—, —S—, —S(=O)— and —S(=O)$_2$—; a $C_2$-$C_6$ alkenyl, a $C_3$-$C_6$ alkynyl, a $C_3$-$C_7$ cycloalkyl each substituted with 0-2 $R^{1b}$, and a $C_7$-$C_{11}$ bicycloalkyl substituted with 0-2 $R^{1b}$; phenyl substituted with 0-3 $R^{1c}$, a 5- to 6-membered heteroaryl containing 1 to 4 heteroatoms each independently a member selected from the group consisting of N, O and S, wherein said heteroaryl is substituted with 0-3 $R^{1c}$;
each $R^{1a}$ is independently a member selected from the group consisting of a $C_6$-$C_{10}$ aryl substituted with 0-3 $R^{1c}$, a perfluorophenyl, a 5- to 6-membered monocyclic or 8- to 10-membered bicyclic heteroaryl containing 1 to 4 heteroatoms each independently a member selected from the group consisting of N, O and S, wherein said heteroaryl is substituted with 0-3 $R^{1c}$, a $C_3$-$C_8$ cycloalkyl substituted with 0-2 $R^{1b}$, a $C_7$-$C_{11}$ bicycloalkyl substituted with 0-2 $R^{1b}$, and a $C_1$-$C_3$ perfluoroalkyl;
each $R^{1b}$ is independently a member selected from the group consisting of a H, $C_1$-$C_6$ alkyl, $C_1$-$C_6$ alkoxy, $CF_3$, $OCF_3$, —$S(=O)_2CH_3$, and acetyl;
each $R^{1c}$ is independently a member selected from the group consisting of a H, OH, F, Cl, Br, CN, $NO_2$, $COOR^{12}$, $C(=O)NR^{12}R^{11}$, $S(=O)_2NR^{12}R^{11}$, acetyl, —$SCH_3$, —$S(=O)CH_3$, —$S(=O)_2CH_3$, —NR$^{12}$OR$^{11}$, C$_1$-C$_6$ alkoxy, C$_1$-C$_3$ perfluoroalkyl, C$_1$-C$_3$ perfluoroalkoxy and a C$_1$-C$_6$ alkyl;

each R$^2$ is independently a member selected from the group consisting of H and C$_1$-C$_6$ alkyl;

B is a member selected form the group consisting of —CH$_2$—, —OCH$_2$—, —NR$^{11}$CH$_2$—, —CH$_2$CH$_2$— and a bond;

R$^6$ is independently a member selected from group consisting of a 5- to 6-membered monocyclic heteroaryl containing 1 to 4 heteroatoms each independently a member selected from the group consisting of N, O and S, wherein said heteroaryl is substituted with 1 R$^{6a}$ and 0-2 R$^{1c}$; and a 8- to 10-membered bicyclic heteroaryl containing 1 to 4 heteroatoms each independently a member selected from the group consisting of N, O and S, wherein said heteroaryl is substituted with 0-3 R$^{1c}$; and each R$^{6a}$ is independently a member selected from the group consisting of phenyl substituted with 0-3 R$^{1c}$; a 5- to 6-membered heteroaryl containing 1 to 4 heteroatoms each independently a member selected from the group consisting of N, O and S, wherein said heteroaryl is substituted with 0-3 R$^{1c}$.

10. The compound of claim 9, wherein
R$^1$ is a C$_1$-C$_2$ alkyl substituted with 1 R$^{4a}$;
R$^{4a}$ is selected from the group consisting of a tert-butyl, a C$_3$-C$_7$ cycloalkyl substituted with 0-2 R$^{1b}$, and a C$_7$-C$_{11}$ bicycloalkyl substituted with 0-2 R$^{1b}$;
each R$^{1b}$ is independently a member selected from the group consisting of a H, C$_1$-C$_6$ alkyl, C$_1$-C$_6$ alkoxy, CF$_3$, OCF$_3$, —S(═O)$_2$CH$_3$, and acetyl;
R$^2$ is H;
R$^6$ is a 8- to 10-membered bicyclic heteroaryl containing 1 to 4 heteroatoms each independently a member selected from the group consisting of N, O and S, wherein said heteroaryl is substituted with 0-3 R$^{1c}$; and
B is —CH$_2$—.

11. The compound of claim 1, wherein said compound has formula Ih:

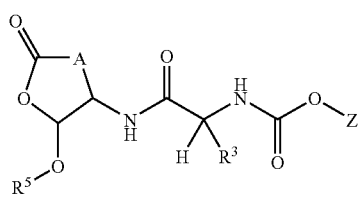

wherein:
A is —CH$_2$—.

12. The compound of claim 1, wherein said compound does not inhibit a caspase.

13. The compound of claim 12, wherein the inhibition constant of the compound for at least one caspase is at least 10 times greater than the inhibition constant for cathepsin S.

14. The compound of claim 12, wherein the inhibition constant of the compound for at least one caspase is at least 100 times greater than the inhibition constant for cathepsin S.

15. The compound of claim 12, wherein the inhibition constant of the compound for at least one caspase is at least 1000 times greater than the inhibition constant for cathepsin S.

16. The compound of claim 12, wherein the inhibition constant of the compound for at least one caspase is at least 10,000 times greater than the inhibition constant for cathepsin S.

17. A pharmaceutical composition, said composition comprising a compound according to claim 1, and a pharmaceutically acceptable excipient.

18. The compound of claim 1, wherein said compound is selected from the group consisting of:

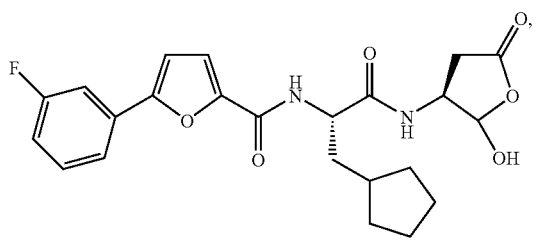

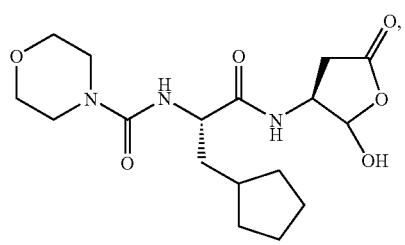

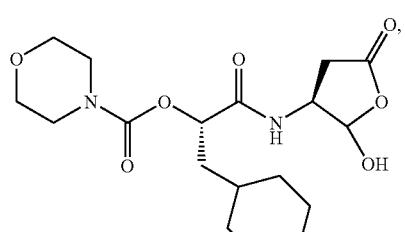

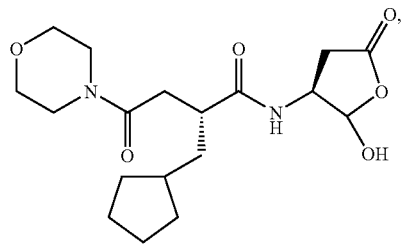

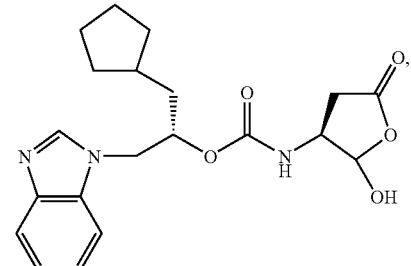

-continued
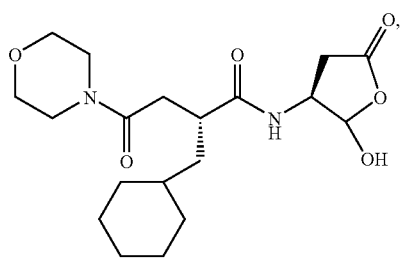
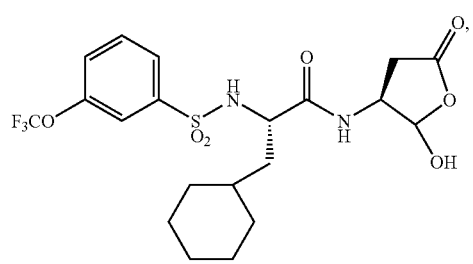
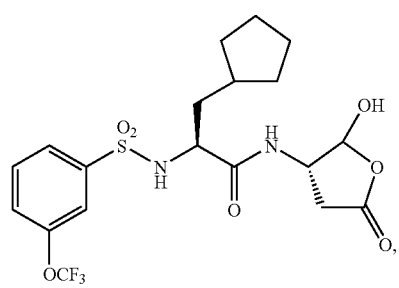
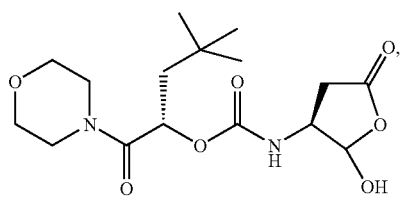
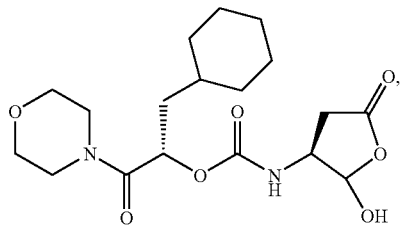
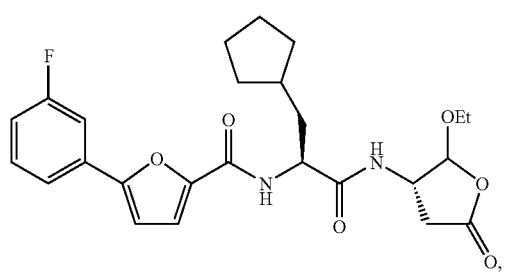
-continued
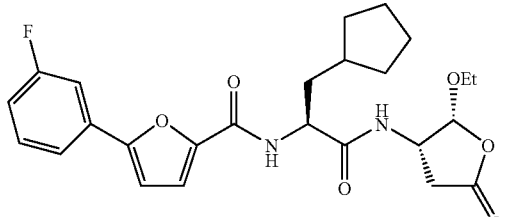
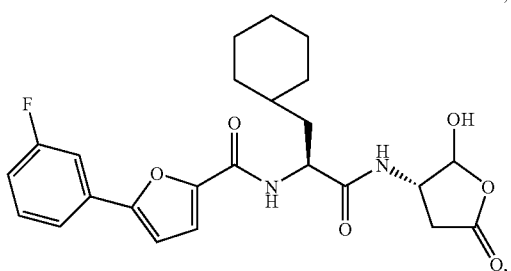
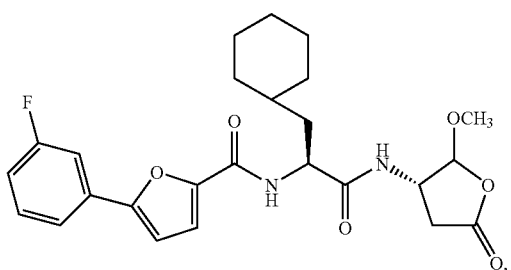
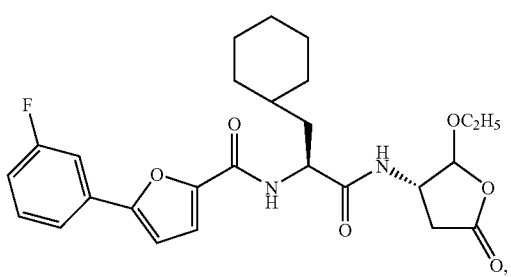
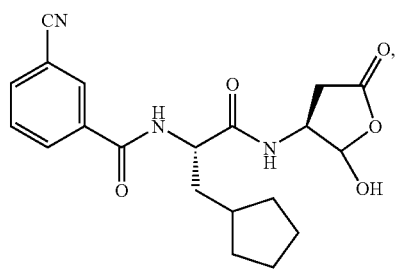
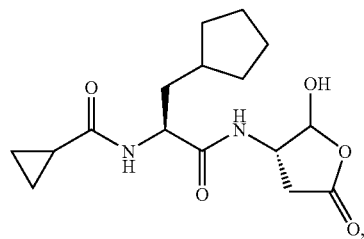

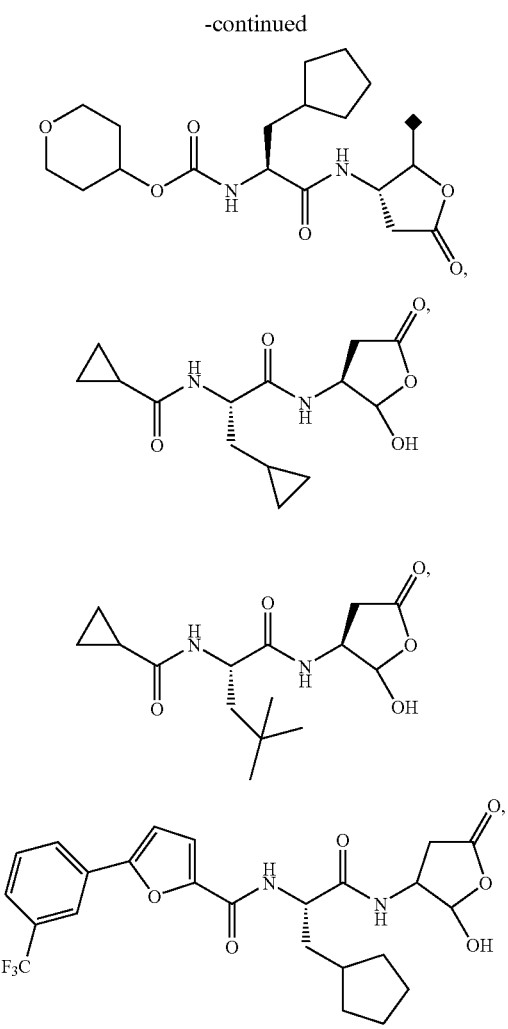
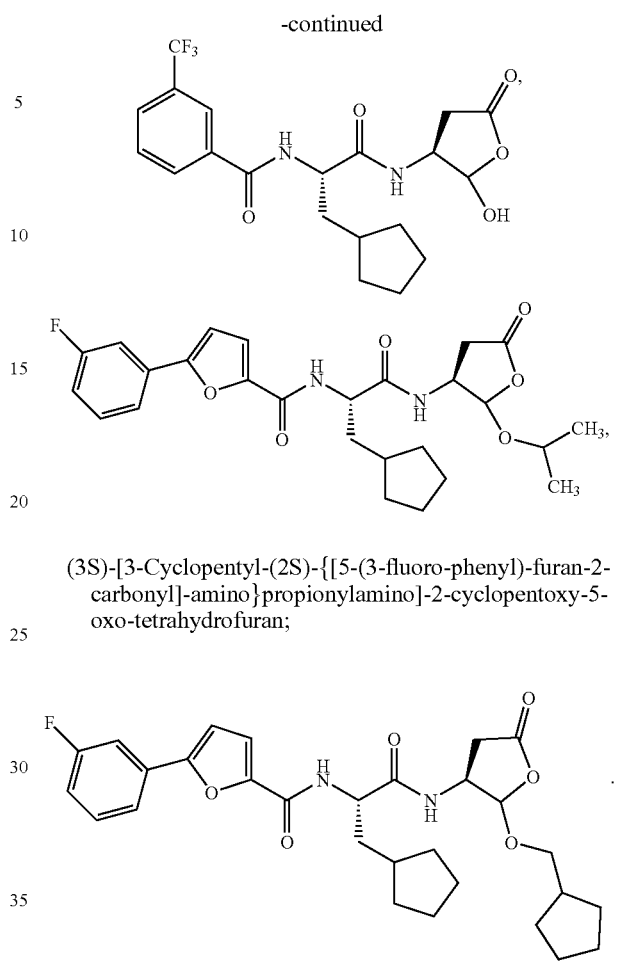
(3S)-[3-Cyclopentyl-(2S)-{[5-(3-fluoro-phenyl)-furan-2-carbonyl]-amino}propionylamino]-2-cyclopentoxy-5-oxo-tetrahydrofuran;
19. A pharmaceutical composition, said composition comprising a compound according to claim 18, and a pharmaceutically acceptable excipient.
\* \* \* \* \*

UNITED STATES PATENT AND TRADEMARK OFFICE
CERTIFICATE OF CORRECTION

PATENT NO. : 7,297,714 B2  Page 1 of 1
APPLICATION NO. : 10/970344
DATED : November 20, 2007
INVENTOR(S) : Liu et al.

It is certified that error appears in the above-identified patent and that said Letters Patent is hereby corrected as shown below:

In column 4, line 51, please delete "well known", and insert --well-known--.
In column 31, line 48, please delete "Karanewsy", and insert --Karanewsky--.
In column 37, line 63, please delete "was.", and insert --was--.
In column 37, line 66, please delete "solyent", and insert --solvent--.
In claim 18, after column 70 line 35, please insert the following:

--

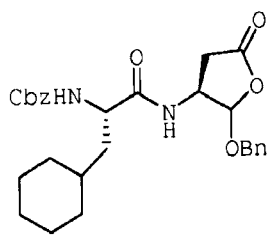 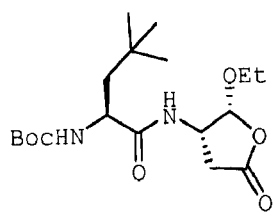 and 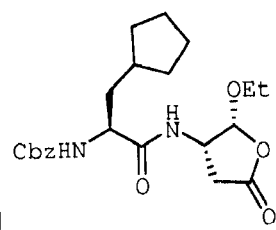

-- .

Signed and Sealed this

Second Day of September, 2008

JON W. DUDAS
*Director of the United States Patent and Trademark Office*